United States Patent [19]

Sjogren

[11] Patent Number: 5,441,953

[45] Date of Patent: Aug. 15, 1995

[54] 4- AMINO DERIVATIVES OF MYCOPHENOLIC ACID

[75] Inventor: Eric B. Sjogren, Mountain View, Calif.

[73] Assignee: Syntex (U.S.A.) Inc., Palo Alto, Calif.

[21] Appl. No.: 311,666

[22] Filed: Sep. 23, 1994

Related U.S. Application Data

[62] Division of Ser. No. 198,817, Feb. 18, 1994, Pat. No. 5,380,879.

[51] Int. Cl.⁶ .................. A61K 31/365; A61K 31/535; C07D 307/88; C07D 413/12
[52] U.S. Cl. .............................. 514/233.5; 514/320; 514/365; 514/385; 514/403; 514/422; 544/153; 546/196; 548/146; 548/311.4; 548/364.4; 549/310
[58] Field of Search ................... 544/153; 546/196; 548/364.4; 549/310; 514/233.5

[56] References Cited

U.S. PATENT DOCUMENTS

| | | |
|---|---|---|
| 3,825,571 | 7/1974 | Mori et al. . |
| 3,853,919 | 12/1974 | Mori et al. . |
| 4,686,234 | 8/1987 | Nelson et al. . |
| 4,725,622 | 2/1988 | Nelson et al. . |
| 4,727,069 | 2/1988 | Nelson et al. . |
| 4,748,173 | 5/1988 | Nelson et al. . |
| 4,753,935 | 6/1988 | Nelson et al. . |
| 4,786,637 | 11/1988 | Allison et al. . |
| 4,808,592 | 2/1989 | Nelson et al. . |
| 4,861,776 | 8/1989 | Nelson et al. . |
| 4,868,153 | 9/1989 | Allison et al. . |
| 4,948,793 | 8/1990 | Allison et al. . |
| 4,952,579 | 8/1990 | Nelson et al. . |
| 4,959,387 | 9/1990 | Nelson et al. . |
| 4,992,467 | 2/1991 | Allison et al. . |
| 5,247,083 | 9/1993 | Knox et al. . |

FOREIGN PATENT DOCUMENTS

| | | |
|---|---|---|
| 48086860 | 11/1973 | Japan . |
| 1290667 | 11/1989 | Japan . |

OTHER PUBLICATIONS

Suzuki, et al., "Antitumor Activity of Derivatives of Mycophenolic Acid", *The Journal of Antibiotics*, Mar. 1976, vol. XXIX, No. 3, pp. 275–285.

Carman, et al., "Derivatives of Mycophenolic Acid", *Aust. J. Chem.*, 1978, 31, pp. 353–364.

Nelson, et al., "Synthesis and Immunosuppressive Activity of Some Side-Chain Variants of Mycophenolic Acid", *J. Med. Chem.*, 1990, 33, pp. 833–838.

Patterson, et al., "The Orthoester Claisen Rearrangement in the Synthesis of Mycophenolic Acid", *J. Chem. Soc., Chem. Commun.*, 1991, No. 21, pp. 1579–1580.

Yat Sun Or, et al., Design and Synthesis of Mycophenolic Acid Analogues as Potential Immunosuppressants (American Chemical Society paper presentation), Washington, D.C., Aug. 21–25, 1994.

*Primary Examiner*—Robert W. Ramsuer
*Attorney, Agent, or Firm*—Brian Lewis

[57] ABSTRACT

The disclosed derivatives of mycophenolic acid are therapeutic agents advantageous in the treatment of disease states indicated for mycophenolic acid and/or mycophenolate mofetil and other immunosuppressant agents.

18 Claims, No Drawings

4- AMINO DERIVATIVES OF MYCOPHENOLIC ACID

This application is a division of application Ser. No. 08/198,817, filed Feb. 18, 1994 now U.S. Pat. No. 5,380,879.

CROSS-REFERENCE TO RELATED APPLICATIONS

This application is related to the following co-pending applications: Ser. Nos. 08/198,749, Attorney Docket No. 27960, entitled "5-Substituted Derivatives of Mycophenolic Acid"; 08/198,732, Attorney Docket No. 27980, entitled "4-Amino Derivatives of 5-Substituted Mycophenolic Acid"; 08/198,725, Attorney Docket No. 27990, entitled "6-Substituted Mycophenolic Acid and Derivatives"; and 08/198,741, Attorney Docket No. 28000, entitled "4-Amino 6-Substituted Mycophenolic Acid and Derivatives"; filed contemporaneously herewith and incorporated herein by reference.

1. Field of the Invention

The present invention relates to mycophenolic acid in which the 4-hydroxy group has been replaced by amino substituents. The invention is also directed to formulations and methods for treatment.

2. Background Information and Related Disclosures

Mycophenolic acid ("MPA") is a weakly active antibiotic found in the fermentation broth of *Penicillium brevicompactum*, having the following structure.

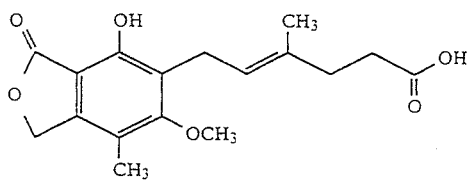

Mycophenolic Acid

MPA and certain related compounds, such as mycophenolate mofetil (the morpholinoethyl ester of MPA), having the following structure:

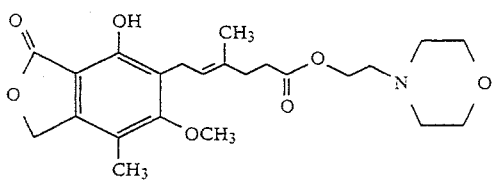

have more recently been described as having particularly advantageous properties as immunosuppressant drugs.

Various derivatives of mycophenolic acid, their synthesis and uses in the treatment of autoimmune disorders, psoriasis, inflammatory diseases, including, in particular, rheumatoid arthritis, tumors, viruses, and for treatment of allograft rejection, are described in U.S. Pat. Nos. 4,686,234; 4,725,622; 4,727,069; 4,748,173; 4,753,935; 4,786,637; 4,808,592; 4,861,776; 4,868,153; 4,948,793; 4,952,579; 4,959,387; 4,992,467; 5,247,083; and U.S. patent application Ser. No. 07/927,260, filed Aug. 7, 1992.

As immunosuppressive agents, the previously described esters and derivatives of mycophenolic acid are useful in treating auto-immune related disorders, glomerulonephritis and hepatitis, and in preventing allograft rejection. As anti-inflammatory agents, they are useful in treating rheumatoid arthritis. As anti-tumor agents, they are useful in treating solid tumors and malignancies of lymphoreticular origins.

See also U.S. Pat. Nos. 3,825,571 and 3,853,919; Japanese Pat. No. J 01290667; *J. Med. Chem.*, 33(2), 833-8 (1990); *Austr. J. Chem.*, 31(2), 353-64, (1978); and *J. Antibiot.*, 29(3), 275-85, 286-91 (1976). The disclosed compounds are described as having anti-tumor, immunosuppressive, anti-viral, anti-arthritic and/or anti-psoriatic activities. The article by J. W. Patterson and G. Huang, Chemical Communications, 1579 (1991) describes synthetic methodology of interest with respect to such compounds.

The above-cited patents, publications, and the references/publications referenced therein, are all incorporated herein by reference.

SUMMARY OF THE INVENTION

One aspect of the invention concerns compounds represented by Formula I:

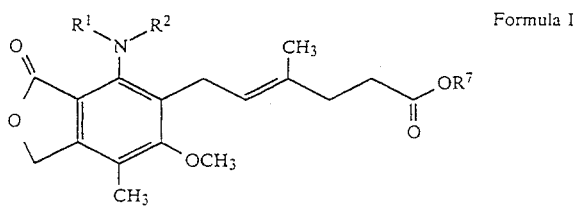

Formula I wherein:

$R^1$ is hydrogen or lower alkyl;

$R^2$ is hydrogen, lower alkyl, —C(O)$R^3$, —C(O)N$R^4R^5$, —CO$_2R^6$, or —SO$_2R^3$ where:

$R^3$ is hydrogen, lower alkyl, halo lower alkyl or optionally substituted phenyl;

$R^4$ is hydrogen, lower alkyl or optionally substituted phenyl;

$R^5$ is hydrogen, lower alkyl or optionally substituted phenyl;

$R^6$ is lower alkyl or optionally substituted phenyl; and $R^7$ is hydrogen, lower alkyl, optionally substituted phenyl, or —(CH$_2$)$_m$—N=Y, wherein:

m is an integer from two to four; and

Y is lower alkylene of four to six carbon atoms or lower alkylene of three to five carbon atoms and one member that is —O—, —S—, or —N($R^8$)— where $R^8$ is hydrogen or lower alkyl;

are useful as therapeutic agents, particularly for immunosuppressive, anti-inflammatory, anti-tumor, anti-viral and anti-psoriatic indications.

In another aspect, the invention relates to a pharmaceutical composition containing a therapeutically effective amount of a compound of Formula I admixed with at least one pharmaceutically acceptable excipient.

In still another aspect, the invention relates to a method of treating immune, inflammatory, tumor, proliferative, viral and psoriatic disorders in a mammal by administering to a mammal in need of such treatment a therapeutically effective amount of a compound of Formula I or a pharmaceutically acceptable salt thereof.

In yet another aspect, the invention relates to the methods of preparation of compounds of Formula I.

DETAILED DESCRIPTION OF THE INVENTION

Definitions and General Parameters

The following definitions are set forth to illustrate and define the meaning and scope of the various terms used to describe the invention herein.

As used herein, the term "alkyl" refers to a fully saturated monovalent radical of one to twelve carbon atoms containing only carbon and hydrogen, and which may be a cyclic, branched or straight chain radical. This term is further exemplified by radicals such as methyl, ethyl, t-butyl, pentyl, cyclopentyl, cyclohexyl, heptyl, cycloheptyl and adamantyl.

The term "lower alkyl" refers to a monovalent alkyl radical of one to six carbon atoms. This term is further exemplified by such radicals as methyl, ethyl, n-propyl, isopropyl, cyclopropyl, n-butyl, t-butyl, i-butyl (or 2-methylpropyl), isoamyl, pentyl, cyclopentyl, i-pentyl, hexyl and cyclohexyl.

The term "halo" refers to fluoro and chloro, unless otherwise specified.

The term "halo lower alkyl" refers to a lower alkyl radical substituted with one or more chlorine or fluorine atoms. This term is further exemplified by such radicals as trichloromethyl, trifluoromethyl, dichloromethyl, fluoromethyl, difluoro-chloro-methyl, 3-chloropropyl and 4-trifluoro-2-chloro-butyl.

The term "halomethyl" refers to a methyl radical substituted with one or more chlorine and/or fluorine atoms. This term is further exemplified by such radicals as trichloromethyl, trifluoromethyl, dichloromethyl, fluoromethyl and difluoro-chloro-methyl.

The term "lower alkylene" refers to a divalent alkyl radical of one to six carbon atoms. This term is further exemplified by such radicals as methylene, ethylene, n-propylene, i-propylene, n-butylene, t-butylene, i-butylene (or 2-methylpropylene), isoamylene, pentylene, and n-hexylene.

The term "alkoxy" means the group —OR wherein R is lower alkyl.

The term "lower alkanol" means an alcohol of the formula ROH where R is a lower alkyl. This term is further exemplified by such alcohols as methanol, ethanol, n-propanol, i-propanol, n-butanol, t-butanol, i-butanol (or 2-methylpropanol), pentanol, n-hexanol.

The moiety "—N=Y" as defined represents a heterocycle radical such as pyrrolidino, piperidino, hexameithyleneimino, imidazolidino, thiazolidino, morpholino, thiomorpholino, piperazino, thiopentamethyleneimino, and the like.

The term "optionally substituted phenyl" refers to phenyl and mono-, di-, or tri-substituted phenyl, wherein the optional substituents are lower alkyl, lower alkoxy, hydroxy, trifluoromethyl, or halo. This term is further exemplified by such radicals as 2-chlorophenyl, 2-trifluoromethylphenyl, 4-methoxyphenyl, 4-chlorophenyl, 3,4-dimethoxyphenyl, 2-chloro-3,4-dimethoxyphenyl, 4-hydroxyphenyl, 4-methylphenyl, 3-t-butylphenyl, and 4-hexylphenyl.

The term "optional" or "optionally" means that the subsequently described event or circumstance may or may not occur, and that the description includes instances in which said event or circumstance occurs and instances in which it does not. For example, "optionally substituted phenyl" means that the phenyl may or may not be substituted and that the description includes both unsubstituted phenyl and phenyl wherein there is substitution: "optionally" followed by "converting the free base to the acid addition salt" means that such conversion may or may not be carried out in order for the process described to fall within the invention, and the invention includes those processes wherein the free base is converted to the acid addition salt and those processes in which it is not.

A "pharmaceutically acceptable salt" may be any salt derived from an inorganic or organic acid or base. Salts may be derived from acids or bases.

The acid addition salts are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid and the like.

The base addition salts are derived from inorganic bases such as sodium hydroxide, potassium hydroxide, lithium hydroxide, ammonia, calcium hydroxide, magnesium hydroxide and the like. Cations derived from organic bases include those formed from primary, secondary and tertiary amines, such as isopropylamine, diethylamine, trimethylamine, triethylamine, pyridine, cyclohexylamine, ethylene diamine, monoethanolamine, diethanolamine, triethanolamine and the like.

As used herein, the term "inert organic solvent" or "inert solvent" means a solvent inert under the conditions of the reaction being described in conjunction therewith (including, for example, benzene, toluene, acetonitrile, tetrahydrofuran, diethyl ether, chloroform, methylene chloride, pyridine, xylene, dimethylformamide, 1,4-dioxane, dichloromethane, and the like).

As used herein, the term "treatment" or "treating" means any treatment of a disease in a mammal, and includes:

(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

As used herein, the term "effective amount" means a dosage sufficient to provide treatment. This will vary depending on the patient and the treatment being effected.

Unless specified to the contrary, the reactions described herein take place at atmospheric pressure over a temperature range from about −20° C. to about 100° C., more preferably from about 10° C. to about 50° C., and most preferably at about room temperature.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be found by reference to the examples hereinbelow. However, other equivalent separation or isolation procedures can, of course, also be used.

Nomenclature

The compounds of Formula I will be named using the numbering system illustrated below:

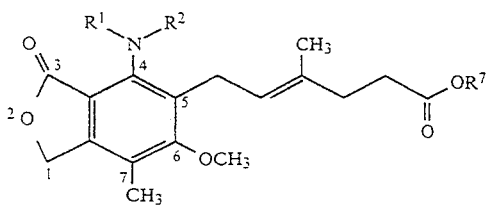

The compounds of the present invention are prepared as the E (or Entgegen) configurational isomer. Following are examples of how some representative compounds of Formula I are named.

The compound of Formula I where $R^1$, $R^2$ and $R^7$ are hydrogen is named "(E)-6-(1,3-dihydro-4-amino-6-methoxy-7-methyl-3-oxoisobenzofuran-5-yl)-4-methyl-4-hexenoic acid".

The compound of Formula I where $R^1$ and $R^2$ are hydrogen, and $R^7$ is methyl is named "methyl (E)-6-(1,3-dihydro-4-amino-6-methoxy-7-methyl-3-oxoisobenzofuran-5-yl)-4-methyl-4-hexenoate".

The compound of Formula I where $R^1$ and $R^2$ are hydrogen, and $R^7$ is morpholinoethyl is named "2-(morpholin-4-yl)ethyl (E)-6-(1,3-dihydro-4-amino-6-methoxy-7-methyl-3-oxoisobenzofuran-5-yl)-4-methyl-4-hexenoate".

The compound of Formula I where $R^1$ is hydrogen, $R^2$ is methyl, and $R^7$ is hydrogen is named "(E)-6-(1,3-dihydro-4-methylamino-6-methoxy-7-methyl-3-oxoisobenzofuran-5-yl)-4-methyl-4-hexenoic acid".

The compound of Formula I where $R^1$ is hydrogen, $R^2$ is —C(O)$R^3$, $R^3$ is —CF$_3$, and $R^7$ is hydrogen is named "(E)-6-[1,3-dihydro-4-(trifluoroacetyl)amino-6-methoxy-7-methyl-3-oxoisobenzofuran-5-yl]-4-methyl-4-hexenoic acid".

The compound of Formula I where $R^1$ is hydrogen, $R^2$ is —C(O)NR$^4$R$^5$ where $R^4$ and $R^5$ are methyl, and $R^7$ is hydrogen is named "(E)-6-(1,3-dihydro-4-[3,3-dimethylureido]-6-methoxy-7-methyl-3-oxoisobenzofuran-5-yl)-4-methyl-4-hexenoic acid".

The compound of Formula I where $R^1$ is hydrogen, $R^2$ is —C(O)NR$^4$R$^5$ where $R^4$ is hydrogen and $R^5$ is 4-methoxyphenyl, and $R^7$ is hydrogen is named "(E)-6-(1,3-dihydro-4-[3-(4-methoxyphenyl)-ureido]-6-methoxy-7-methyl-3-oxoisobenzofuran-5-yl)-4-methyl-4-hexenoic acid".

PREPARATION OF COMPOUNDS OF FORMULA I

The compounds of Formula I are prepared from a common intermediate, the (E)-6-(1,3-dihydro-4-isocyanato-6-methoxy-7-methyl-3-oxoisobenzofuran-5-yl)-4-methyl-4-hexenoate esters of Formula (7), the structure of which is shown below:

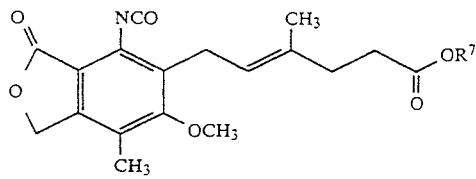

where $R^7$ is lower alkyl.

The compounds of Formula (7) are then converted to the compounds of Formula I by several different synthetic pathways, depending on the desired substitution at the 4-position and the definition of $R^7$.

Many of the esterification routes and/or final esterification steps for the esters of the 4-substituted derivatives of mycophenolic acid are described in U.S. Pat. Nos. 4,686,234; 4,725,622; 4,727,069; 4,748,173; 4,753,935; 4,861,776; and the application entitled "Direct Esterification of Mycophenolic Acid", Ser. No. 07/911635, filed Jul. 10, 1992 now abandoned (by inventors working in the same research organization as that of the present applicants, and subject to an obligation of assignment to the same assignee as in the present application) all previously incorporated herein by reference. By substituting the acids of Formula I for mycophenolic acid or its acid derivatives as described in the above references, the esterification routes and/or final steps described may likewise be used.

Starting Materials

Mycophenolic acid is commercially available, for example from Ajinomoto Company Incorporated of Tokyo, Japan. It can be made, for example, as described in U.S. Pat. No. 4,452,891, incorporated herein by reference.

Preparation of Intermediates of Formula (7)

The preparation of a compound of Formula (7) is shown in Reaction Scheme I below.

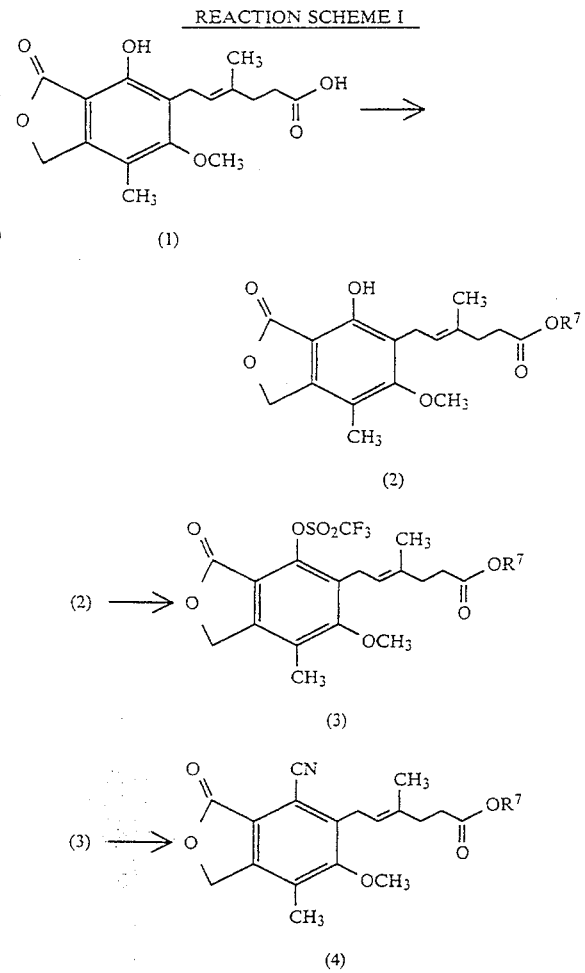

REACTION SCHEME I

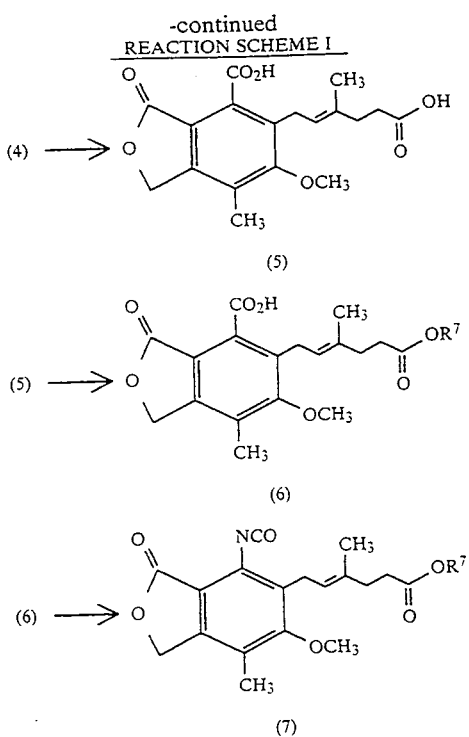

-continued
REACTION SCHEME I where $R^7$ is lower alkyl.

Preparation of Compounds of Formula (2)

Mycophenolic acid, the compound of Formula (1), is commercially available. Mycophenolic acid is reacted with a large excess of an alcohol of the formula $R^7OH$, where $R^7$ is lower alkyl, preferably methanol, with catalytic amounts of an acid catalyst, (such as methane sulfonic acid, sulfuric acid, hydrochloric acid and p-toluene sulfonic acid), preferably p-toluene-sulfonic acid). The reaction is carried out in the temperature range from about 0° C. to 40° C., preferably at about 20° C., for about 1 to 7 days, preferably about 24 hours. The reaction product, a lower alkyl ester of mycophenolic acid, a compound of Formula (2) where $R^7$ is lower alkyl, is isolated and purified by conventional means.

Preparation of Compounds of Formula (3)

A compound of Formula (2), where $R^7$ is lower alkyl, in an inert solvent, preferably chloroform or dichloromethane, is reacted with a slight excess, preferably about 1.1 molar equivalents, of a sulfonic anhydride, (such as a halo lower alkyl sulfonic anhydride, halomethyl sulfonic anhydride, or halosulfonic anhydride, or preferably trifluoromethane sulfonic anhydride or fluorosulfonic anhydride) or a sulfonyl halide, (such as trifluoromethyl sulfonyl bromide, preferably trifluoromethyl sulfonyl chloride), in the presence of about 1 to 3 molar equivalents, preferably about 2 molar equivalents, of a tertiary organic base, preferably pyridine. The reaction is carried out in the temperature range from about −20° C. to 20° C., preferably at about 0° C., for about 15 to 45 minutes, preferably about 30 minutes. The trifluoromethyl sulfonyl reaction product, a compound of Formula (3) where $R^7$ is lower alkyl, is isolated and purified by conventional means.

Preparation of Compounds of Formula (4)

A compound of Formula (3), where $R^7$ is lower alkyl, is reacted with about 1 to 3 molar equivalents, preferably about 1.85 molar equivalents, of potassium cyanide, in the presence of a catalytic amount of a triarylphosphine palladium complex, preferably tetrakis(triphenylphosphine) palladium, in an organic solvent, preferably 1,4-dioxane. The reaction is carried out in the temperature range from about 70° C. to 130° C., preferably at about the reflux temperature of 1,4-dioxane, for about 10 to 30 hours, preferably about 18 hours. The cyano reaction product, a compound of Formula (4) where $R^7$ is lower alkyl, is isolated and purified by conventional means, preferably with extraction by an organic solvent and column chromatography.

Preparation of Compounds of Formula (5)

A compound of Formula (4), where $R^7$ is lower alkyl, is hydrolyzed by reacting it with about 1 to 10 molar equivalents, preferably about 4 molar equivalents, of an inorganic base (e.g., sodium hydroxide, lithium hydroxide, or potassium hydroxide, preferably sodium hydroxide,) in a large excess of a protic solvent, preferably about a 3:2 water:methanol solution. The reaction is carried out in the temperature range from about 40° C. to 130° C., preferably at about reflux, for about 1 to 3 hours, preferably about 2 hours. The reaction solution is distilled to remove approximately 30% of the volume of solvent added, and an additional amount of about 1 to 1.6 molar equivalents, preferably about 1.3 molar equivalents, of an inorganic base (e.g., sodium hydroxide, lithium hydroxide, or potassium hydroxide, preferably sodium hydroxide,) is added, and the reaction is continued in the temperature range from about 40° C. to 130° C., preferably at about reflux temperature, for about 1 to 3 days, preferably about 2 days. The reaction product, E-6-(1,3-dihydro-4-carboxy-6-methoxy-7-methyl-3-oxoisobenzofuran-5-yl)-4-methyl-4-hexenoic acid, the compound of Formula (5), is isolated and purified by conventional means.

Alternatively, the compound of Formula (5) may be prepared by reacting a corresponding compound of Formula (3) with a catalytic amount of 1,1′-Bis (diphenylphosphine) ferrocene palladium dichloride in a large excess of an alkanol (preferably methanol) in an organic solvent (preferably trimethyl formamide) with a slight excess, preferably 1.01 molar equivalents, of an organic base (preferably triethylamine), under a carbon monoxide atmosphere of increased pressure of about 400–1000 PSI, preferably at about 600 PSI. The reaction product, which is a diester of a compound of Formula (5), is then hydrolyzed by reacting it with about 1 to 10 molar equivalents, preferably about 4 molar equivalents, of an inorganic base, preferably aqueous lithium hydroxide, in a large excess of a protic solvent, preferably 4:1 methanol/water solution. The solution is heated to a temperature range from about 30° C. to 80° C., preferably from about 50° C. to 60° C., for about 1 to 10 hours, preferably for about 2 to 6 hours. The reaction product, E-6-(1,3-dihydro-4-carboxy-6-methoxy-7-methyl-3-oxo-5-isbenzofuranyl)-4-methyl-4-hexenoic acid, the compound of Formula (5), is isolated and purified by conventional means.

Preparation of Compounds of Formula (6)

E-6-(1,3-dihydro-4-carboxy-6-methoxy-7-methyl-3-oxo-5-isbenzofuranyl)-4-methyl-4-hexenoic acid, the compound of Formula (5), is reacted in a large excess of a lower alkanol of the formula $R^7OH$, preferably methanol, with catalytic amounts of an acid catalyst, preferably p-toluene-sulfonic acid. The reaction is carried out in the temperature range from about 0° C. to 40° C., preferably at about 20° C., for about 4 hours to 3 days, preferably about 24 hours. The reaction product, a corresponding lower alkyl ester compound of Formula (6)

where $R^7$ is lower alkyl, is isolated and purified by conventional means.

Preparation of Compounds of Formula (7)

A compound of Formula (6), where $R^7$ is lower alkyl, is reacted with about 1 to 3 molar equivalents, preferably about 2 molar equivalents, of an organic base, preferably triethylamine, in a large excess of an organic solvent, preferably dimethylformamide, and about 1 to 2 molar equivalents, preferably about 1.3 molar equivalents, of an alkyl or phenyl haloformate or of a dialkyl or diphenyl halophosphate, preferably diphenyl chlorophosphate, in the temperature range from about −20° C. to 20° C., preferably at about 0° C. The reaction mixture is allowed to warm to the temperature range from about 0° C. to 40° C., preferably at about 20° C., and maintained there for about 0.5 to 2 hours, preferably about 1 hour. The reaction mixture is recooled to the temperature range from about −20° C. to 20° C., preferably at about 0° C., a large excess of sodium azide added, and the temperature preferably maintained at about 0° C. for about 10 to 30 hours, preferably about 18 hours. The 4-isocyanato reaction product, a compound of Formula (7) where $R^7$ is lower alkyl, is isolated and purified by conventional means.

Alternatively, a compound of Formula (6) is reacted with about 1 to 3 molar equivalents, preferably about 2 molar equivalents, of an organic base, preferably triethylamine, in a large excess of an organic solvent, preferably dimethylformamide, and with a slight excess, preferably 1.2 molar equivalents, of a diphenyl or dialkyl phosphoroazide, preferably diphenyl phosphoroazide, in the temperature range from about 0° C. to 40° C., preferably at about 20° C., for about 12 to 36 hours, preferably for about 24 hours. The isocyanato reaction product, a compound of Formula (7) where $R^7$ is lower alkyl, is isolated and purified by conventional means.

Preparation of Compounds of Formula I where $R^1$, $R^2$, and $R^7$ are all Hydrogen The compounds of Formula I where $R^1$, $R^2$, and $R^7$ are all hydrogen (designated as compounds of Formula IA) are prepared from the compounds of Formula (7) as shown in Reaction Scheme II below.

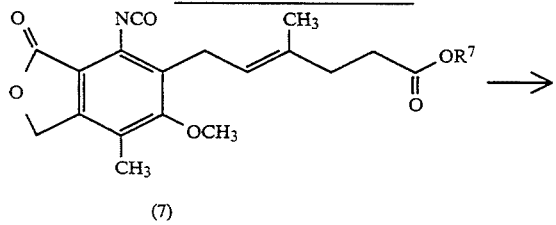

where $R^7$ is lower alkyl.

Preparation of Formula IA

A compound of Formula (7), where $R^7$ is lower alkyl, is reacted with about 1 to 20 molar equivalents, preferably 10 molar equivalents, of an inorganic base, preferably lithium hydroxide monohydrate, in a protic solvent, preferably 3:10 water:1,4-dioxane. The reaction is carried out in the temperature range from about 0° C. to 40° C., preferably at about 20° C., for about 1 to 3 hours, preferably about 2 hours. The reaction product, (E)-6-(1,3-dihydro-4-amino-6-methoxy-7-methyl-3-oxoisobenzofuran-5-yl)-4-methyl-4-hexenoic acid, the compound of Formula IA, is isolated and purified by conventional means, preferably column chromatography.

Preparation of Compounds of Formula IB

The compounds of Formula I where $R^1$ is hydrogen and $R^2$ is $-C(O)NR^4R^5$ (designated as compounds of Formula IB) are prepared from the compounds of Formula (7) as shown in Reaction Scheme III below.

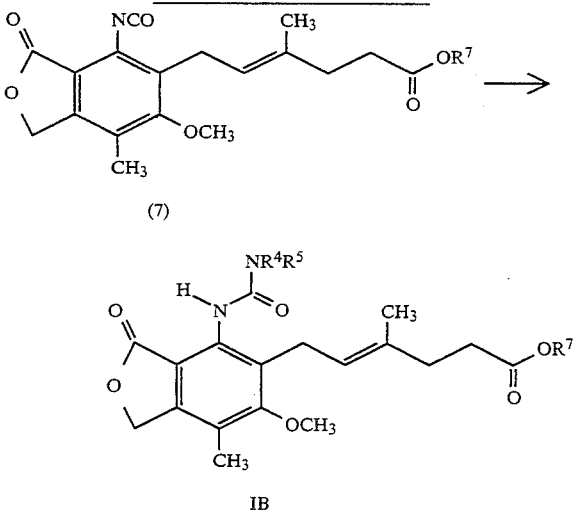

Preparation of Formula IB

A compound of Formula (7) where $R^7$ is lower alkyl is reacted with a large excess of an amine of the formula $HNR^4R^5$, where $R^4$ and $R^5$ are as defined in the Summary of Invention, for example, methylamine, dimethylamine, methylphenylamine, ammonia, and the like, in an inert organic solvent, preferably tetrahydrofuran. The reaction is carried out in the temperature range from about 0° C. to 40° C., preferably at about 20° C., for about 30 minutes to 2 hours, preferably about 1 hour. The reaction product, a 4-ureido ester of Formula IB where $R^7$ is lower alkyl, is isolated and purified by conventional means.

Preparation of Formula IB where $R^7$ is hydrogen

An ester of Formula IB where $R^7$ is lower alkyl is hydrolyzed by reacting with about 1 to 10 molar equivalents, preferably about 4 molar equivalents of an inorganic base, preferably aqueous lithium hydroxide, in a large excess of an organic solvent, preferably 4:1 methanol/water. The solution is heated to a temperature range from about 30° C. to 80° C., preferably from about 50° C. to 60° C., for about 1 to 10 hours, preferably for about 2 to 6 hours. The reaction product, a 4-ureido acid compound of Formula IB where $R^7$ is hydrogen, is isolated and purified by conventional means. Formula IB where $R^7$ is hydrogen, is isolated and purified by conventional Preparation of Compounds of Formula I where $R^1$ is Hydrogen and $R^2$ is $-C(O)R^3$ The compounds of Formula I where $R^1$ is hydrogen and $R^2$ is —C(O)$R^3$ (designated as compounds of Formula IC), are prepared from the compounds of Formula IA as shown in Reaction Scheme IV below.

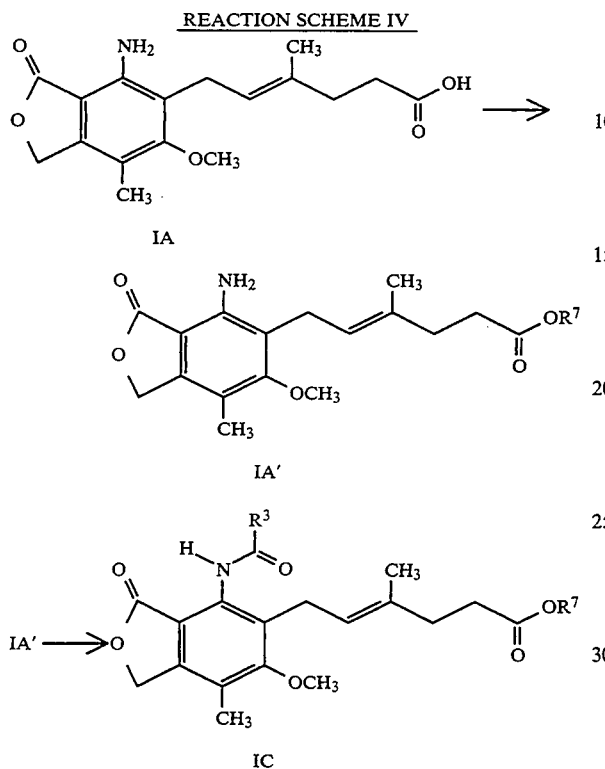

REACTION SCHEME IV where $R^7$ is lower alkyl.

Preparation of Compounds of Formula IA', a Compound of Formula I wherein $R^1$ and $R^2$ are hydrogen, and $R^7$ is lower alkyl (E)-6-(1,3-dihydro-4-amino-6-methoxy-7-methyl-3-oxoisobenzofuran-5-yl)-4-methyl-4-hexenoic acid, the compound of Formula IA, is esterified with a lower alkanol of the formula $R^7$OH, as described in the preparation of a compound of Formula (2) to give the reaction product, a lower alkyl ester of (E)-6-(1,3-dihydro-4-amino-6-methoxy-7-methyl-3-oxoisobenzofuran-5-yl)-4-methyl-4-hexenoic acid, a compound of Formula IA'.

Preparation of Compounds of Formula IC where $R^7$ is Lower Alkyl

A compound of Formula IA' is reacted in a large excess of an inert organic solvent, preferably dichloromethane, with about 1 to 6 molar equivalents, preferably about 2.5 molar equivalents, of an anhydride of the formula ($R^3$C(O))$_2$O, or an acyl chloride of the formula $R^3$C(O)Cl, where $R^3$ is as defined in the Summary of the Invention. The reaction is carried out in the temperature range from about 0° C. to 40° C., preferably at about 20° C., for about 30 minutes to 2 hours, preferably about 1 hour. The reaction product, an amido ester of Formula IC where $R^7$ is lower alkyl, is isolated and purified by conventional means, preferably by recrystallization.

Preparation of Formula IC where $R^7$ is Hydrogen

A compound of Formula IC where $R^7$ is lower alkyl is hydrolyzed as described in the preparation of a compound of Formula IB where $R^7$ is hydrogen to give a 4-amido compound of Formula IC where $R^7$ is hydrogen.

Preparation of Compounds of Formula I where $R^1$ is Lower Alkyl and $R^2$ is —C(O)$R^3$ The compounds of Formula I where $R^1$ is lower alkyl and $R^2$ is —C(O)$R^3$ (designated as compounds of Formula ID) are prepared from the compounds of Formula IC where $R^7$ is lower alkyl as shown in Reaction Scheme V below.

REACTION SCHEME V

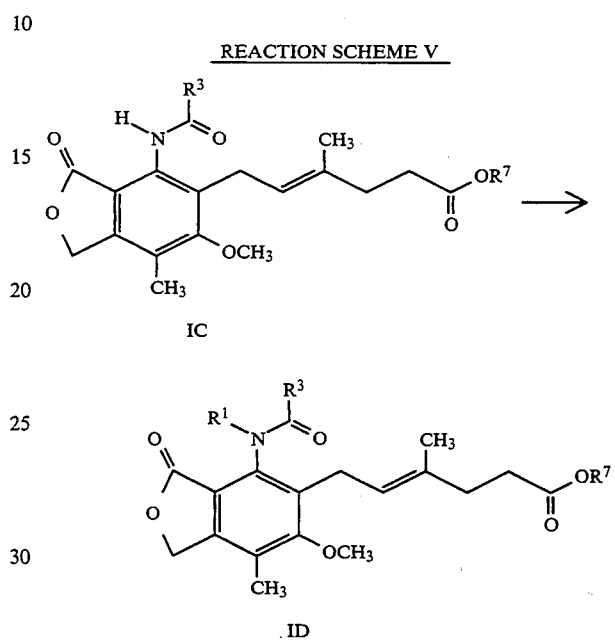

where $R^7$ is lower alkyl.

Preparation of Formula ID wherein $R^1$ and $R^7$ are Lower Alkyl

A compound of Formula IC where $R^7$ is lower alkyl is reacted in the presence of about 1 to 10 molar equivalents, preferably about 4.5 molar equivalents, of a mild base, preferably potassium carbonate, and with about 1 to 10 molar equivalents, preferably about 4 molar equivalents, of a lower alkyl bromide or iodide, preferably an iodide, in an inert organic solvent, preferably dimethylformamide. The reaction is carried out in the temperature range from about 0° C. to 40° C., preferably at about 20° C., for about 12 to 48 hours, preferably about 24 hours. The organic layer is dried, and then concentrated to an oil, to give an amide ester of Formula ID where $R^1$ and $R^7$ are both lower alkyl.

Preparation of Formula ID wherein $R^1$ is Lower Alkyl and $R^7$ is Hydrogen

A compound of Formula ID where $R^7$ is lower alkyl is hydrolyzed as described in the preparation of a compound of Formula IB to give a carboxylic acid of Formula ID where $R^7$ is hydrogen.

Preparation of Compounds of Formula I where $R^1$ is Lower Alkyl, and $R^2$ and $R^7$ are Hydrogens The compounds of Formula I where $R^1$ is lower alkyl, and $R^2$ and $R^7$ are hydrogen (designated as compounds of Formula IE), are prepared from the compounds of Formula ID where $R^7$ is hydrogen as shown in Reaction Scheme VI below.

REACTION SCHEME VI

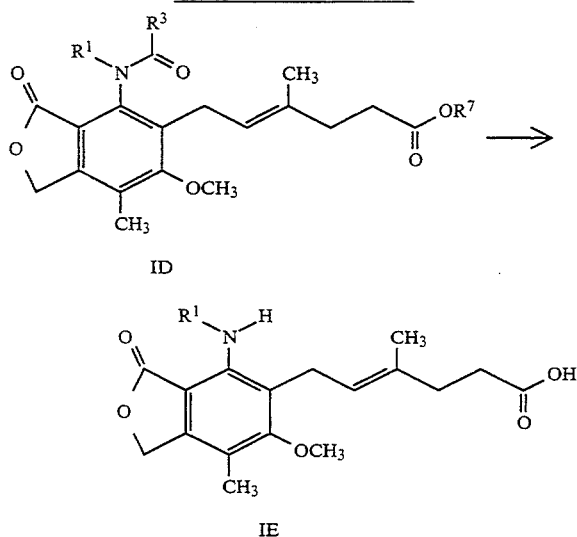

Preparation of Formula IE where $R^1$ is Lower Alkyl

An amido ester of Formula ID is hydrolyzed by reacting with about 1 to 10 molar equivalents, preferably about 4 molar equivalents of an inorganic base (for example sodium hydroxide, preferably lithium hydroxide), in a large excess of an organic solvent, preferably 4:1 methanol/water. The solution is heated to a temperature range from about 50° C. to 100° C., preferably from about 60° C. to 80° C., for about 4 to 24 hours, preferably for about 12 hours. The reaction product, a 4-alkylamino acid compound of Formula IE, is isolated and purified by conventional means.

Preparation of Compounds of Formula I where $R^7$ is Lower Alkyl, Optionally Substituted Phenyl, or $-(CH_2)_m-N=Y$ The compounds of Formula I where $R^7$ is lower alkyl, optionally substituted phenyl, or $-(CH_2)_m-N=Y$ (i.e., ester derivatives) may be prepared from the corresponding compounds of Formula I where $R^7$ is hydrogen, including compounds of Formulae IA, IB, IC, ID, and IE, by conventional means, for example as described in the preparation of a compound of Formula (2).

Preferred Preparation of Esters of Formula I where $R^7$ is $-(CH_2)_m-N=Y$

In a preferred procedure, a compound of Formula I where $R^7$ is hydrogen is esterified with an heterocyclic aminoalkyl alcohol of the formula $R^7OH$, where $R^7$ is $-(CH_2)_m-N=Y$, in which m and Y are as defined in the Summary of the Invention, by the direct esterification procedure described in the pending application entitled "Direct Esterification of Mycophenolic Acid", Ser. No. 07/911635, filed Jul. 10, 1992.

In the direct esterification route, an acid compound of Formula I where $R^7$ is hydrogen is esterified by refluxing in an inert organic solvent capable of azeotropic removal of water (such as toluene, xylene, or a mixture thereof) in the presence of a slight excess (between 1.01 to 1.20 molar equivalents, and preferably, 1.05 to 1.06 molar equivalents) of a heterocyclic aminoalkyl alcohol of the formula $HO(CH_2)_m-N=Y$. Water generated by the reaction is removed azeotropically.

For example, with toluene as the solvent: 1) the reaction takes place with (a) a reaction time of 20 to 120 hours, preferably 50 to 100 hours and most preferably 100 hours and (b) an initial pot temperature range of 114° to 120° C. increasing to a final pot temperature range of 118° to 130° C., preferably an initial pot temperature range of 115° to 118° C. increasing to a final pot temperature range of 118° to 125° C., each depending on solute concentration and atmospheric pressure, and most preferably an initial pot temperature of 116° C. increasing to a final pot temperature of 121° C. with a ratio of the acid compound of Formula I (where $R^7$ is hydrogen) to toluene of 1 gm:2 ml at one atmosphere of pressure. The reaction product, a compound of Formula I where $R^7$ is $-(CH_2)_m-N=Y$, is isolated and purified by conventional means.

Salts of Compounds of Formula I

Some of the compounds of Formula I may be converted to corresponding base addition salts by virtue of the presence of a carboxylic acid group. The conversion is accomplished by treatment with a stoichiometric amount of an appropriate base, such as potassium carbonate, sodium bicarbonate, ammonia, ethylenediamine, monoethanolamine, diethanolamine, triethanolamine and the like. Typically, the free acid is dissolved in a polar organic solvent such as ethanol, methanol or ethyl acetate, and the base added in water, ethanol, methanol or isopropanol. The temperature is maintained at about 0° C. to 50° C. The resulting salt precipitates spontaneously or may be brought out of solution with a less polar solvent.

The base addition salts of the compounds of Formula I may be decomposed to the corresponding free acids by treating with at least a stoichiometric amount of a suitable acid, such as hydrochloric acid or sulfuric acid, typically in the presence of aqueous solvent, and at a temperature of between about 0° C. and 50° C. The free acid form is isolated by conventional means, such as extraction with an organic solvent.

By virtue of the presence of an amine group in the 4-position, some of the compounds of Formula I may be converted to the acid addition salts by the substitution of an organic or inorganic acid for the base in the above procedure. The acid salts can be decomposed to the corresponding free bases by similar treatment with an appropriate base.

Preferred Processes

In summary, compounds of Formula I are prepared according to the following last steps:

1. A process for preparing compounds of Formula I, wherein:

$R^1$ is hydrogen or lower alkyl;

$R^2$ is hydrogen, lower alkyl, $-C(O)R^3$, $-C(O)NR^4R^5$, $-CO_2R^6$, or $-SO_2R^3$ where:

$R^3$ is hydrogen, lower alkyl, halo lower alkyl or optionally substituted phenyl;

$R^4$ is hydrogen, lower alkyl or optionally substituted phenyl;

$R^5$ is hydrogen, lower alkyl or optionally substituted phenyl;

$R^6$ is lower alkyl or optionally substituted phenyl; and $R^7$ is hydrogen;

comprises:

reacting a compound of the formula:

Formula I where $R^7$ is lower alkyl, optionally substituted phenyl, or —$(CH_2)_m$—N=Y, with an inorganic base.

2. Alternatively, a process for preparing compounds of Formula I, wherein:
$R^1$ is hydrogen or lower alkyl;
$R^2$ is hydrogen, lower alkyl, —C(O)$R^3$, —C(O)NR$^4$R$^5$, —CO$_2$R$^6$, or —SO$_2$R$^3$ where:
$R^3$ is hydrogen, lower alkyl, halo lower alkyl or optionally substituted phenyl;
$R^4$ is hydrogen, lower alkyl or optionally substituted phenyl;
$R^5$ is hydrogen, lower alkyl or optionally substituted phenyl;
$R^6$ is lower alkyl or optionally substituted phenyl; and
$R^7$ is lower alkyl, optionally substituted phenyl, or —$(CH_2)_m$—N=Y, wherein:
m is an integer from two to four; and
Y is lower alkylene of four to six carbon atoms or lower alkylene of three to five carbon atoms and one member that is —O—, —S—, or —N($R^8$)— where $R^8$ is hydrogen or lower alkyl;
comprises:
reacting a compound of the formula:

Formula I where $R^7$ is hydrogen with a compound of the formula $R^7$OH where $R^7$ is as defined above.

3. Alternatively, a process for preparing compounds of Formula I, wherein:
$R^1$ is hydrogen;
$R^2$ is —C(O)NR$^4$R$^5$, where $R^4$ and $R^5$ are independently hydrogen, lower alkyl or optionally substituted phenyl; and
$R^7$ is lower alkyl;
comprises:
reacting a compound of the formula:

(7)

where $R^7$ is lower alkyl, with a compound of the formula HNR$^4$R$^5$, where $R^4$ and $R^5$ are as defined above.

4. Alternatively, a process for preparing compounds of Formula I, wherein:
$R^1$ is hydrogen;
$R^2$ is —C(O)$R^3$, where $R^3$ is lower alkyl, halo lower alkyl or optionally substituted phenyl; and
$R^7$ is lower alkyl, optionally substituted phenyl, or —$(CH_2)_m$—N=Y,;
comprises:
reacting a compound of the formula:

with a compound of the formula $(R^3C(O))_2O$ or $R^3C(O)$ Cl.

5. Alternatively, a process for preparing compounds of Formula I, wherein:
$R^1$ is lower alkyl;
$R^2$ is —C(O)$R^3$, where $R^3$ is lower alkyl, halo lower alkyl or optionally substituted phenyl; and
$R^7$ is lower alkyl;
comprises:
reacting a compound of the formula:

where $R^7$ is lower alkyl, with a compound of the formula $R^1X$, where $R^1$ is lower alkyl and X is iodine or bromine.

Preferred Compounds

Among the family of compounds of the present invention, one preferred category includes the compounds where $R^1$ is hydrogen. Within this category a preferred group includes the compounds where $R^2$ is hydrogen or —C(O)$R^3$.

One preferred subgroup within this group includes compounds in which $R^2$ is hydrogen. One preferred class within this subgroup includes compounds in which $R^7$ is hydrogen, lower alkyl, or morpholinoethyl.

Another preferred subgroup of this group includes compounds in which $R^2$ is —C(O)$R^3$ where $R^3$ is halomethyl, especially where $R^3$ is —CF$_3$. One preferred class within this subgroup includes compounds in which $R^7$ is hydrogen, lower alkyl, or morpholinoethyl.

Yet another preferred subgroup of this group includes compounds in which $R^2$ is lower alkyl, especially where $R^2$ is methyl. One preferred class within this subgroup includes compounds in which $R^7$ is hydrogen, lower alkyl, or morpholinoethyl.

Another preferred subgroup of this group includes compounds in which $R^2$ is —C(O)NR$^4$R$^5$. One preferred class within this group includes compounds in which $R^4$ and $R^5$ are independently hydrogen or lower alkyl, especially where they are both methyl. One preferred subclass within this class includes compounds in which $R^7$ is hydrogen, lower alkyl, or morpholinoethyl.

At present the most preferred compounds are:
(E)-6-(1,3-dihydro-4-amino-6-methoxy-7-methyl-3-oxoisobenzofuran-5-yl)-4-methyl-4-hexenoic acid; and
E-6-(1,3-dihydro-4-(trifluoroacetyl)amino-6-methoxy-7-methyl-3-oxoisobenzofuran-5-yl)-4-hexenoic acid.

Utility, Testing and Administration

General Utility

The compounds of the present invention, the pharmaceutically acceptable salts thereof and pharmaceutical compositions therewith (collectively the "compounds" for purposes of the following description) are useful as immunosuppressive agents, anti-inflammatory agents, anti-tumor agents, anti-proliferative agents, anti-viral agents and anti-psoriatic agents in mammals, whether domestic (cattle, pigs, sheep, goats, horses), pets (cats, dogs), or preferably humans. The compounds are inhibitors of inosine monophosphate dehydrogenase (IMPDH) and thus inhibit de novo purine synthesis; they have anti-proliferative effects (e.g., against smooth muscle cells and both B and T lymphocytes) and inhibit antibody formation and the glycosylation of cell adhesion molecules in lymphocytes and endothelial cells.

As immunosuppressive agents, the compounds are useful in treating auto-immune related disorders, for example: Type I Diabetes Mellitus; Inflammatory Bowel Disease (e.g., Crohn's Disease and Ulcerative Colitis); Systemic Lupus Erythematosus; Chronic Active Hepatitis; Multiple Sclerosis; Grave's Disease; Hashimoto's Thyroiditis; Behcet's Syndrome; Myasthenia Gravis; Sjogren's Syndrome; Pernicious Anemia; Idiopathic Adrenal Insufficiency; and Polyglandular Autoimmune Syndromes Type I and II.

The compounds are also useful as therapeutic immunosuppressive agents in the treatment of Asthma, Immunohemolytic Anemia, Glomerulonephritis, and Hepatitis. Preventative uses of the compounds as immunosuppressive agents include the treatment of allograft rejection, for example, in cardiac, lung, pancreatic, renal, liver, skin and corneal allografts, and prevention of Graft vs. Host Disease.

The compounds are useful for inhibiting proliferative responses to vascular injury, for example, stenosis following an insult to a blood vessel wall in post-angioplasty restenosis, and post-cardiac by-pass surgery restenosis.

The compounds are useful as anti-inflammatory agents, for example, in treating Rheumatoid Arthritis, Juvenile Rheumatoid Arthritis and Uveitis.

As anti-tumor agents, the compounds are useful in treating solid tumors and malignancies of lymphoreticular origin. For example, the compounds' utility for treatment of solid tumors includes: cancers of the head and neck, including squamous cell carcinoma; lung cancer, including small cell and non-small cell lung carcinoma; mediastinal tumors; esophageal cancer, including squamous cell carcinoma and adenocarcinoma; pancreatic cancer; cancer of the hepatobiliary system, including hepatocellular carcinoma, cholangiocarcinoma, gall bladder carcinoma and biliary tract carcinoma; small intestinal carcinoma, including adenocarcinoma, sarcoma, lymphoma and carcinoids; colorectal cancer, including colon carcinoma and rectal carcinoma; metastatic carcinoma; cancers of the genitourinary system, including ovarian cancer, uterine sarcoma, and renal cell, ureteral, bladder, prostate, urethral, penile, testicular, vulvar, vaginal, cervical, endometrial, and fallopian tube carcinoma; breast cancer; endocrine system cancer; soft tissue sarcomas; malignant mesotheliomas; skin cancer, including squamous cell carcinoma, basal cell carcinoma and melanoma; cancer of the central nervous system; malignant bone tumors; and plasma cell neoplasms.

As anti-tumor agents for the treatment of malignancies of lymphoreticular origin, the compounds are useful in treating, for example: Lymphomas and Leukemias, including B, T and promonocyte cell line malignancies, Mycoses Fungoides, Non-Hodgkins Lymphoma, Malignancies of Burkitt Lymphoma Cells and other EBV-transformed B-lymphocytes, Lymphomas resulting from Epstein-Barr viral infections in allograft recipients, Chronic Lymphocytic Leukemia, Acute Lymphocytic Leukemia and Hairy Cell Leukemia.

As anti-viral agents, the compounds are useful in treating, for example: retroviruses, including Human T-leukemia Viruses, Types I and II (HTLV-1 and HTLV-2), Human Immuno Deficiency Viruses, Types I and II (HIV-1, HIV-2) and, Human Nasopharyngeal Carcinoma Virus (NPCV) and in treating Herpes Viruses, including ESV infected B-lymphocytes, CMV infection, Herpes Virus Type 6, Herpes Simplex, Types 1 and 2, (HSV-1, HSV-2) and Herpes Zoster.

As anti-psoriatic agents, the compounds are useful in treating, for example, psoriasis and psoriatic arthritis.

Testing

Activity testing is conducted as described in the following references, and by modifications thereof.

General anti-inflammatory, anti-viral, anti-tumor, anti-psoriatic and/or immunosuppressive activity is associated with the inhibition of Inosine 5'-Monophosphate Dehydrogenase ("IMPDH"). In vitro assays measuring the inhibition of IMPDH, for example, by determining the level of NADH formation according to the method of Anderson, J. H. and Sartorelli, A. C., *J. Biol. Chem.*, 243:4762–4768 (1968) are predictive of such activity.

Initial animal screening tests to determine anti-inflammatory activity potential include the adjuvant arthritis assay, e.g., according to the method of Pearson, *Proc. Soc. Exp. Biol. Med.*, 91:95–101 (1956). Also, in vitro tests, for example those using synovial explants from patients with rheumatoid arthritis, Dayer, et al., *J. Exp. Med.*, 145:1399–1404(1977), are useful in determining whether compounds exhibit anti-inflammatory activity.

Autoimmune activity is determined, for example, utilizing experimental allergic encephalomyelitis, by a modification of a procedure initially described by Grieg, et. al., *J. Pharmacol. Exp. Ther.*, 173:85 (1970).

Human clinical trials for efficacy in the treatment of asthma are conducted, e.g., as described by Erzurum, Leff, Cochran, et al. "Lack of benefit of methotrexate in severe, steroid-dependent asthma. A double-blind, placebo controlled study." *Ann. Int. Med.*, 114:353–360 (1991).

Activity to prevent the rejection of organ or tissue allografts in experimental animals is determined, for example, as described by Hao, et al., *J. Immunol.*, 139:4022–4026 (1987). In addition, U.S. Pat. No. 4,707,443 and EP 226062, incorporated herein by reference, also describe assays for activity in prevention of allograft rejection by detection of IL-2R levels. Human clinical trials to establish efficacy in preventing rejection of solid organ transplants (such as renal) are conducted, e.g., as described by Lindholm, Albrechtsen, Tufveson, et al., "A randomized trial of cyclosporin and prednisolone versus cyclosporin, azathioprine and prednisolone in primary cadaveric renal transplantation," *Transplantation*, 54:624–631 (1992). Human clinical trials for graft vs. host disease are conducted, e.g., as described by Storb, Deeg, Whitehead, et al., "Methotrexate and cyclosporin compared with cyclosporin alone for prophylaxis of acute graft versus host disease after marrow transplantation for leukemia." *New England J. Med.*, 314:729–735 (1986).

Immunosuppressive activity is determined by both in vivo and in vitro procedures. In vivo activity is determined, e.g., utilizing a modification of the Jerne hemolytic plaque assay, [Jerne, et al., "The agar plaque technique for recognizing antibody producing cells," *Cell-bound Antibodies*, Amos, B. and Kaprowski, H. editors (Wistar Institute Press, Philadelphia) 1963, p. 109]. In vitro activity is determined, e.g., by an adaptation of the procedure described by Greaves, et al., "Activation of human T and B lymphocytes by polyclonal mitogens," *Nature*, 248:698–701 (1974).

Anti-viral activity is determined, for example, by the procedure described by Smee, et al. ["Anti-Herpesvirus Activity of the Acyclic Nucleoside 9-(1,3-Dihydroxy-2-Propoxymethyl)Guanine," *Antimicrobial Agents and Chemotherapy*, 23(5):676–682 (1983)], or as described by Planterose ["Antiviral and cytotoxic effects of mycophenolic acid," *Journal of General Virology*, 4:629 (1969)].

Anti-viral activity can likewise be determined by measurement of reverse transcriptase activity, for example, according to the method described by Chen et al., *Biochem. Pharm.*, 36:4361 (1987).

Human clinical trials for anti-HIV efficacy (together with clinical treatment scenarios) are described and cited, for example, by Sande, et al., "Antiretroviral Therapy for Adult HIV-Infected Patients," *JAMA*, 270(21):2583–2589 (1993). A large scale clinical trial can be conducted, e.g., as described by Volberding, P.A., et al. "Zidovudine in asymptomatic human immunodeficiency virus infection: a controlled trial in persons with fewer than 500 CD4 positive cells per cubic millimeter," *New England J. Med.*, 322(14):941–949 (1990). A smaller scale (Phase I) clinical trial can be conducted, e.g., as described by Browne, et al., "2′,3′-Didehydro-3′-deoxythymidine (d4T) in Patients with AIDS or AIDS-Related Complex: A Phase I Trial, " *J. Infectious Diseases*, 167:21–29 (1993).

Tests for systemic activity in psoriasis can be carried out, for example, as described by Spatz, et al., "Mycophenolic acid in psoriasis," *British Journal of Dermatology*, 98:429 (1978).

Tests for anti-tumor activity can be performed, for example, as described by Carter, et al. ["Mycophenolic acid: an anticancer compound with unusual properties," *Nature*, 223:848 (1969)].

In vitro activity for treating stenosis is demonstrated, for example, by inhibiting the proliferation of smooth muscle cells, as established by the following human arterial smooth muscle cell proliferation assay. Human smooth muscle cells are grown in culture. A test group is treated with the test compound added at selected concentrations in fresh media. Both groups receive 2 μCi tritiated thymidine ($^3$HTdR), a radioisotope label. After 24 hours, the cells are harvested and the amount of label incorporated into DNA is counted by scintillation; this is compared for the test and control groups, the amount being proportional to cell proliferation. Inhibition of smooth muscle proliferation is established when the test group has a lower radioisotope count than the control group. The concentrations of test compound required to inhibit proliferation by 50% (the $IC_{50}$), and to inhibit proliferation by more than 95% are determined.

In vivo activity for treating stenosis is demonstrated, for example, in rat and pig models for arterial stenosis. In the rat model, a test group is treated with the test compound, starting 6 days before and continuing for 14 days after injury to the left carotid artery; the test group is compared to a control group receiving vehicle without the test compound. Injury is achieved by a gentle perfusion of air through a 10 mm long section of the left artery. The right artery is left intact. Arterial cross-sections (10 μm) are taken from both the left and right arteries of each subject, and the area of the vessel wall (endothelium, intima, media) is measured, The amount of vascular proliferation is calculated by subtracting the mean area of the intact, right carotid artery from the mean area of the injured, left carotid artery. Reduction in vascular proliferation is established when the test group shows less proliferation than the control group.

Human clinical trials for restenosis after coronary angioplasty are conducted, e.g., as described by Serruys, Rutsch, Heyndrickx, et al., "Prevention of restenosis after percutaneous transluminal coronary antioplasty with thromboxane $A_2$-receptor blockade: a randomozed, double-blind, placebo-controlled trial." *Circulation*, 84:1568–80 (1991).

Administration

The compounds of Formula I are administered at a therapeutically effective dosage, e.g., a dosage sufficient to provide treatment for the disease states previously described. Administration of the compounds of the invention or the pharmaceutically acceptable salts thereof can be via any of the accepted modes of administration for agents that serve similar utilities. The compounds can be used both prophylactically (e.g., to prevent allograft rejection) and therapeutically.

While human dosage levels have yet to be optimized for the compounds of the invention, generally, a daily dose is from about 0.01 to 100.0 mg/kg of body weight, preferably about 0.1 to 64.3 mg/kg of body weight, and most preferably about 0.3 to 43.0 mg/kg of body weight. Thus, for administration to a 70 kg person, the dosage range would be about 0.7 mg to 7 g per day, preferably about 7.0 mg to 4.5 g per day, and most preferably about 21 mg to 3.0 g per day. The amount of active compound administered will, of course, be dependent on the subject and disease state being treated, the severity of the affliction, the manner and schedule of administration (e.g., oral administration one day prior to cancer chemotherapy and intravenous administration during cancer chemotherapy) and the judgment of the prescribing physician.

In employing the compounds of this invention for treatment of the above conditions, any pharmaceutically acceptable mode of administration can be used. The compounds of Formula I can be administered either alone or in combination with other pharmaceutically acceptable excipients, including solid, semi-solid, liquid or aerosol dosage forms, such as, for example, tablets, capsules, powders, liquids, injectables, suspensions, suppositories, aerosols or the like. The compounds of Formula I can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier or excipient and a compound of Formula I or a pharmaceutically acceptable salt thereof. In addition, these compositions may include other medicinal agents, pharmaceutical agents, carriers, adjuvants, etc., such as multidrug resistance modifying agents, steroids, immunosuppressants such as cyclosporine A, azathioprene, rapamycin, FK-506, brequinar, leflunomide and vincrystine.

Generally, depending on the intended mode of administration, the pharmaceutically acceptable composition will contain about 0.1% to 90%, preferably about 0.5% to 50%, by weight of a compound or salt of Formula I, the remainder being suitable pharmaceutical excipients, carriers, etc.

One preferred manner of administration for the conditions detailed above is oral, using a convenient daily dosage regimen which can be adjusted according to the degree of affliction. For such oral administration, a pharmaceutically acceptable composition is formed by the incorporation of any of the normally employed excipients, such as, for example, mannitol, lactose, starch, povidone, magnesium stearate, sodium saccharine, talcum, cellulose, croscarmellose sodium, glucose, gelatin, sucrose, magnesium carbonate, and the like. Such compositions take the form of solutions, suspensions, tablets, dispersible tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like; a lubricant such as magnesium stearate or the like; a disintegrant such as croscarmellose sodium or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, suspending agents, emulsifying agents, or solubilizing agents, pH buffering agents and the like, for example, sodium acetate, sodium citrate, cyclodextrine derivatives, polyoxyethylene, sorbitan monolaurate or stearate, etc. Actual methods of preparing such dosage forms are known, or will be apparent, to those skilled in this art; for example, see *Remington's Pharmaceutical Sciences*, Mack Publishing Company, Easton, Penn., 15th Edition, 1975. The composition or formulation to be administered will, in any event, contain a quantity of the active compound in an amount effective to alleviate the symptoms of the subject being treated.

Dosage forms or compositions containing active ingredient in the range of 0.005% to 95% with the balance made up from pharmaceutically acceptable carrier may be prepared.

For oral administration, a pharmaceutically acceptable composition is formed by the incorporation of any of the normally employed excipients, such as, for example pharmaceutical grades of mannitol, lactose, starch, magnesium stearate, talcum, povidone, cellulose derivatives, croscarmellose sodium, glucose, sucrose, magnesium carbonate, sodium saccharin, talcum and the like. Such compositions take the form of solutions, suspensions, tablets, capsules, powders, sustained release formulations and the like. Such compositions may contain 0.01%–95% active ingredient, preferably 0.1–50%.

For a solid dosage form containing liquid, the solution or suspension, in for example propylene carbonate, vegetable oils or triglycerides, is preferably encapsulated in a gelatin capsule. Such ester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, polyoxyethylene, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2–2% of the active agent in solution.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

EXAMPLES

The following examples are given to enable those skilled in the art to more clearly understand and to practice the present invention. They should not be considered as limiting the scope of the invention, but merely as being illustrative and representative thereof.

EXAMPLE 1

Preparation of Compounds of Formula (2)

1A. Preparation of (2) where $R^7$ is Methyl

A solution of 15.1 g (47.1 mmol) of (E)-6-(1,3-dihydro-4-hydroxy-6-methoxy-7-methyl-3-oxoisobenzofuran-5-yl)-4-methyl-4-hexenoic acid (mycophenolic acid) and 0.7 g (3.7 mmol) of p-toluenesulfonic acid in 400 ml of methanol was allowed to stand at room temperature for 3 days. The mixture was concentrated under reduced pressure to approximately 75 ml and then partitioned between aqueous sodium bicarbonate and ethyl acetate. The organic phase was further washed with brine and then dried over sodium sulfate. Concentration of the organic phase under reduced pressure gave 15.4 g (46.0 mmol, 98%) of methyl (E)-6-(1,3-dihydro-4-hydroxy-6-methoxy-7-methyl-3-oxoisobenzofuran-5-yl)-4-methyl-4-hexenoate as a white solid, mp 104°–105° C.

EXAMPLE 2

Preparation of Compounds of Formula (3)

2A. Formula (3) where $R^7$ is Methyl

To a 0° C. solution of 4.59 g (13.7 mmol) of methyl (E)-6-(1,3-dihydro-4-hydroxy-6-methoxy-7-methyl-3-oxoisobenzofuran-5-yl)-4-methyl-4-hexenoate and 2.22 ml (27.4 mmol) of pyridine in 100 ml of methylene chloride was added 2.55 ml (15.1 mmol) of trifluoromethane sulfonic anhydride dropwise. After 30 minutes, the reaction mixture was poured into 1N aqueous sodium hydrogen sulfate. This mixture was extracted with dichloromethane, and the organic phase was further washed with water and brine. The organic phase was dried over magnesium sulfate and concentrated under reduced pressure. Trituration of the residue with hexane gave 5.7 g (12.2 mmol) of methyl (E)-6-(1,3-dihydro-4-trifluoromethylsulfonyloxy-6-methoxy-7-methyl-3-oxoisobenzofuran-5-yl)-4-methyl-4-hexenoate as a white solid, mp 53°–55° C.

EXAMPLE 3

Preparation of Compounds of Formula (4)

3A. Formula (4) where $R^7$ is Methyl

A nitrogen-flushed mixture of 5.8 g (12.4 mmol) of methyl (E)-6-(1,3-dihydro-4-trifluoromethylsulfonyloxy-6-methoxy-7-methyl-3-oxoisobenzofuran-5-yl)-4-methyl-4-hexenoate, 1.5 g (23.0 mmol) of potassium cyanide, and 1.11 g (0.96 mmol) of tetrakis(triphenylphosphine) palladium in 100 ml of 1,4-dioxane was heated at reflux for 18 hours. Upon cooling, the mixture was partitioned between water and ethyl acetate. The organic phase was washed with water six times, with brine once, and then dried over magnesium sulfate. The solvent was evaporated under reduced pressure and the resulting solid was stirred with hexane for 18 hours and then filtered off. This solid was further purified by silica gel chromatography using 5:4 hexane:ethyl acetate to give 4.0 g (11.7 mmol) of methyl (E)-6-(1,3-dihydro-4-cyano-6-methoxy-7-methyl-3-oxoisobenzofuran-5-yl)-4-methyl-4-hexenoate, mp 87°–88° C.

EXAMPLE 4

Preparation of a Compound of Formula (5)

A mixture of 4.0 g (11.7 mmol) of methyl (E)-6-(1,3-dihydro-4-cyano-6-methoxy-7-methyl-3-oxoisobenzofuran-5-yl)-4-methyl-4-hexenoate and 1.86 g (46.5 mmol) of sodium hydroxide in 100 ml of 3:2 water:methanol was heated at reflux for 2 hours. The resulting homogenous solution was distilled until 30 ml of distillate was recovered. An additional 0.6 g (15 mmol) of sodium hydroxide was added to the reaction solution and it was refluxed for 2 days. Upon cooling the solution was partitioned between 1N aqueous HCl and ethyl acetate. The organic phase was washed twice with water, once with brine, and then dried over magnesium sulfate. The solvent was evaporated under reduced pressure to give a solid. This solid was stirred with hexane and then filtered off to give 3.88 g (11.1 mmol) of (E)-6-(1,3-dihydro-4-carboxy-6-methoxy-7-methyl-3-oxoisobenzofuran-5-yl)-4-methyl-4-hexenoic acid as a white solid, mp 172°–174° C.

EXAMPLE 5

Preparation of Compounds of Formula (6)

5A. Formula (6) where $R^7$ is Methyl

A solution of 3.88 g (11.1 mmol) of (E)-6-(1,3-dihydro-4-carboxy-6-methoxy-7-methyl-3-oxoisobenzofuran-5-yl)-4-methyl-4-hexenoic acid and 0.2 g (1.0 mmol) of p-toluene sulfonic acid in methanol (60 ml) was stirred at room temperature for 8 hours. The solvent was evaporated under reduced pressure. The residue was dissolved in ethyl acetate, and this solution was washed twice with water, once with brine, and dried over magnesium sulfate. The solvent was evaporated under reduced pressure to give a solid which was recrystallized from ethyl acetate to give 3.37 g (9.3 mmol) of methyl (E)-6-(1,3-dihydro-4-carboxy-6-methoxy-7-methyl-3-oxoisobenzofuran-5-yl)-4-methyl-4-hexenoate as a white solid, mp 169°–170° C.

EXAMPLE 6

Preparation of Compounds of Formula (7)

6A. Formula (7) where $R^7$ is Methyl

To a stirred, 0° C. solution of 6.0 g (16.6 mmol) of methyl (E)-6-(1,3-dihydro-4-carboxy-6-methoxy-7-methyl-3-oxoisobenzofuran-5-yl)-4-methyl-4-hexenoate in 150 ml of dimethylformamide was added 4.62 ml (33.1 mmol) of triethylamine followed by drop-wise addition of 4.5 ml (21.8 mmol) of diphenylchlorophosphate. The mixture was allowed to stir at room temperature for 1 hour and then recooled to 0° C., and treated with 10.8 g (166 mmol) of sodium azide. This mixture was stirred for 24 hours at 0° C. and then partitioned between aqueous sodium hydrogen sulfate and ethyl acetate. The organic phase was washed four times with water, dried over magnesium sulfate, and concentrated under reduced pressure. The residue was triturated with hexane to give 5.8 g of methyl (E)-6-(1,3-dihydro-4-isocyanato-6-methoxy-7-methyl-3-oxoisobenzofuran-5-yl)-4-methyl-4-hexenoate. A small sample was further purified by rapid silica gel chromatography with an eluant of 1:1 hexane:ethyl acetate followed by recrystallization from hexane-ethyl acetate to give purified methyl (E)-6-(1,3-dihydro-4-isocyanato-6-methoxy-7-methyl-3-oxoisobenzofuran-5-yl)-4-methyl-4-hexenoate, mp 95°–101° C.

EXAMPLE 7

Preparation of Compounds of Formula I

7A. Formula IA where $R^1$, $R^2$ and $R^7$ are Hydrogen 2.0 g (5.5 mmol) of methyl (E)-6-(1,3-dihydro-4-carboxy-6-methoxy-7-methyl-3-oxoisobenzofuran-5-yl)-4-methyl-4-hexenoate, the compound of Formula (6), was treated as in the procedure in Example 6A above, to give methyl E-6-(1,3-dihydro-4-isocyanato-6-methoxy-7-methyl-3-oxoisobenzofuran-5-yl)-4-methyl-4-hexenoate, the methyl ester of Formula (7). Instead of purifying the resulting residue as described in Example 6A, above, it was redissolved in 50 ml of 1,4-dioxane and treated with 16 ml of water and 2.0 g (47.7 mmol) of lithium hydroxide monohydrate. The mixture was stirred at room temperature for 2 hours and then partitioned between aqueous 1N sodium hydrogen sulfate and ethyl acetate. The organic phase was washed twice with water, once with brine, and was dried over magnesium sulfate. The solvent was evaporated under reduced pressure and the residue was purified by chromatography on silica gel, using 50:40:1 hexane:ethyl acetate:acetic acid as eluant to give 1.28 g (4.0 mmol) of (E)-6-(1,3-dihydro-4-amino-6-methoxy-7-methyl-3-oxoisobenzofuran-5-yl)-4-methyl-4-hexenoic acid as a white solid, mp 130°–131° C.

7B. Alternate Synthesis of Formula IA where $R^1$, $R^2$ and $R^7$ are Hydrogen

Similarly, following the procedures of Example 7A above, but replacing the methyl ester of (E)-6-(1,3-dihydro-4-carboxy-6-methoxy-7-methyl-3-oxoisobenzofuran-5-yl)-4-methyl-4-hexenoate with other lower alkyl (e.g., ethyl, t-butyl, pentyl, and cyclopentyl) esters of (E)-6-(1,3-dihydro-4-carboxy-6-methoxy-7-methyl-3-oxoisobenzofuran-5-yl)-4-methyl-4-hexenoate, which may all be prepared by the methods described in Examples 1 through 6 above, (E)-6-(1,3-dihydro-4-amino-6-methoxy-7-methyl-3-oxoisobenzofuran-5-yl)-4-methyl-4-hexenoic acid is obtained.

EXAMPLE 8

Preparation of Compounds of Formula I

8A. Formula IA where $R^1$ and $R^2$ are hydrogen, and $R^7$ is methyl

To a solution of 2.5 g (7.8 mmol) of (E)-6-(1,3-dihydro-4-amino-6-methoxy-7-methyl-3-oxoisobenzofuran-5-yl)-4-methyl-4-hexenoic acid in 50 ml (1.234 mol) of methanol was added 0.125 g (0.66 mmol) of p-toluene sulfonic acid monohydrate. The solution was stirred at room temperature for 2 days and then concentrated to a small volume. The residue was partitioned between water and ethyl acetate. The organic layer was dried over magnesium sulfate and concentrated to a solid. Recrystallization of this solid from hexane-ethyl acetate gave 2.48 g of methyl (E)-6-(1,3-dihydro-4-amino-6-methoxy-7-methyl-3-oxoisobenzofuran-5-yl)-4-methyl-4-hexenoate, mp 91°–93° C.

8B. Formula IA where $R^1$ and $R^2$ are hydrogen, varying $R^7$

Similarly, following the procedures of Example 8A above, but replacing methanol with the following lower alkanols and optionally substituted phenols (other compounds of the formula $R^7OH$) (which may be commercially obtained or prepared by methods known to those skilled in the art):

ethanol, n-propanol, isopropanol, t-butanol, isoamyl alcohol, phenol, 2-chlorophenol, 2-trifluoromethylphenol, and 2-chloro-3,4-dimethoxyphenol;

there are obtained the following respective compounds:

ethyl (E)-6-(1,3-dihydro-4-amino-6-methoxy-7-methyl-3-oxoisobenzofuran-5-yl)-4-methyl-4-hexenoate;

n-propyl (E)-6-(1,3-dihydro-4-amino-6-methoxy-7-methyl-3-oxoisobenzofuran-5-yl)-4-methyl-4-hexenoate;

isopropyl (E)-6-(1,3-dihydro-4-amino-6-methoxy-7-methyl-3-oxoisobenzofuran-5-yl)-4-methyl-4-hexenoate;

t-butyl (E)-6-(1,3-dihydro-4-amino-6-methoxy-7-methyl-3-oxoisobenzofuran-5-yl)-4-methyl-4-hexenoate;

isoamyl (E)-6-(1,3-dihydro-4-amino-6-methoxy-7-methyl-3-oxoisobenzofuran-5-yl)-4-methyl -4-hexenoate;

phenyl (E)-6-(1,3-dihydro-4-amino-6-methoxy-7-methyl-3-oxoisobenzofuran-5-yl)-4-methyl-4-hexenoate;

2-chlorophenyl (E)-6-(1,3-dihydro-4-amino-6methoxy-7-methyl-3-oxoisobenzofuran-5-yl)-4-methyl- 2-trifluoromethylphenyl (E)-6-(1,3-dihydro-4-amino-6-methoxy-7-methyl-3-oxoisobenzofuran-5-yl)-4-methyl-4-hexenoate; and 2-chloro-3,4-dimethoxyphenyl (E)-6-(1,3-dihydro-4-amino-6-methoxy-7-methyl-3-oxoisobenzofuran-5-yl)-4-methyl-4-hexenoate.

EXAMPLE 9

Preparation of Compounds of Formula I

9A. Formula IA where $R^1$ and $R^2$ is hydrogen, and $R^7$ is Morpholinoethyl 7 g (0.02 moles) of (E)-6-(1,3-dihydro-4-amino-6-methoxy-7-methyl-3-oxoisobenzofuran-5-yl)-4-methyl-4-hexenoic acid and toluene (25 ml) are warmed gently to form a solution. A slight excess (1.05 molar equivalents) of 2-morpholinoethanol (3 g, 0.021 moles) and toluene (25 ml) are added. The reaction mixture is stirred for half an hour and then heated to reflux at an initial pot temperature of 117° C. (which increases a few degrees during reflux) under a Dean-Stark trap for 80 hours. The reaction mixture is cooled, washed with water (2×15 ml), 10% aqueous sodium bicarbonate (2×15 ml) and finally with water (15 ml). The toluene layer is stripped to a volume of about 20 ml in vacuo, n-hexane (30 ml) is added and the resulting slurry is aged at room temperature for 2 hours. The product is filtered, washed with n-hexane (ca. 10 ml) and dried in vacuo at 60° C. to yield 2-(morpholin-4-yl)ethyl (E)-6-(1,3-dihydro-4-amino-6-methoxy-7-methyl-3-oxoisobenzofuran-5-yl)-4-methyl-4-hexenoate.

9B. Formula IA where $R^1$ and $R^2$ are hydrogen, varying $R^7$

Similarly, following the procedures of Example 9A above, but replacing morpholinoethanol with the following heterocyclic aminoalkyl alcohols (other compounds of the formula $R^7OH$) (which may be commercially obtained or prepared by methods known to those skilled in the art):

2-(pyrrolidin-1-yl)ethanol,
2-(piperidin-1-yl)ethanol,
2-(thiazolidin-3-yl)ethanol,
3-(morpholin-4-yl)propanol,
4-(morpholin-4-yl)butanol, 2-(imidazolidin-1-yl)ethanol, and
2-(2-methyl-1,2-pyrazolidin-1-yl)ethanol;
there are obtained the following respective compounds:

2-(pyrrolidin-1-yl)ethyl (E)-6-(1,3-dihydro-4-amino-6-methoxy-7-methyl-3-oxoisobenzofuran-5-yl)-4-methyl-4-hexenoate;

2-(piperidin-1-yl)ethyl (E)-6-(1,3-dihydro-4-amino-6-methoxy-7-methyl-3-oxoisobenzofuran-5-yl)-4-methyl-4-hexenoate;

2-(thiazolidin-3-yl)ethyl (E)-6-(1,3-dihydro-4-amino-6-methoxy-7-methyl-3-oxoisobenzofuran-5-yl)-4-methyl-4-hexenoate;

3-(morpholin-4-yl)propyl (E)-6-(1,3-dihydro-4-amino-6-methoxy-7-methyl-3-oxoisobenzofuran-5-yl)-4-methyl-4-hexenoate;

4-(morpholin-4-yl)butyl (E)-6-(1,3-dihydro-4-amino-6-methoxy-7-methyl-3-oxoisobenzofuran-5-yl)-4-methyl-4-hexenoate;

2-(imidazolidin-1-yl)ethyl (E)-6-(1,3-dihydro-4-amino-6-methoxy-7-methyl-3-oxoisobenzofuran-5-yl)-4-methyl-4-hexenoate; and 2-(2-methyl-1,2-pyrazolidin-1-yl)ethyl (E)-6-(1,3-dihydro-4-amino-6-methoxy-7-methyl-3-oxoisobenzofuran-5-yl)-4-methyl-4-hexenoate.

EXAMPLE 10

Preparation of Compounds of Formula (I)

10A. Formula IB where $R^1$ is Hydrogen, $R^2$ is —C(O)NR$^4$R$^5$, where $R^4$, $R^5$ and $R^7$ are all Methyl A solution of 0.65 g (1.8 mmol) of methyl (E)-6-(1,3-dihydro-4-isocyanato-6-methoxy-7-methyl-3-oxoisobenzofuran-5-yl)-4-methyl-4-hexenoate in 10 ml of tetrahydrofuran was treated with 5 ml of a solution of 40% dimethylamine in water. After 1 hour the reaction was partitioned between water and ethyl acetate. The organic phase was washed with water three times, dried over magnesium sulfate, and concentrated under reduced pressure to give 0.4 g of methyl (E)-6-[1,3-dihydro-4-(3,3-dimethylureido)-6-methoxy-7-methyl-3-oxoisobenzofuran-5-yl]-4-methyl-4-hexenoate, mp 116°–118° C.

10B. Formula IB where $R^1$ is Hydrogen, $R^2$ is —C(O)NR$^4$R$^5$, and $R^7$ is Methyl, varying $R^4$ and $R^5$ Similarly, following the procedures of Example 10A above, but replacing dimethylamine with the following compounds of the formula HNR$^4$R$^5$ where $R^4$ and $R^5$ are as defined in the Summary of the Invention (which may be commercially obtained or prepared by methods known to those skilled in the art):

methylamine, ammonia, diethylamine, ethylamine, ethylmethylamine, diphenylamine, phenylamine, methylphenylamine, butylpropylamine, and 2-chlorophenylamine;

there are obtained the following respective compounds:

methyl (E)-6-(1,3-dihydro-4-(3-methyl)ureido-6-methoxy-7-methyl-3-oxoisobenzofuran-5-yl)-4-methyl-4-hexenoate;

methyl (E)-6-(1,3-dihydro-4-ureido-6-methoxy-7-methyl-3-oxoisobenzofuran-5-yl)-4-methyl-4-hexenoate;

methyl (E)-6-(1,3-dihydro-4-(3,3-diethyl)ureido-6-methoxy-7-methyl-3-oxoisobenzofuran-5-yl)-4-methyl-4-hexenoate;

methyl (E)-6-(1,3-dihydro-4-(3 3-ethyl)ureido-6-methoxy-7-methyl-3-oxoisobenzofuran-5-yl)-4-methyl-4-hexenoate;

methyl (E)-6-(1,3-dihydro-4-(3-methyl-3-ethyl)ureido-6-methoxy-7-methyl-3-oxoisobenzofuran-5-yl)-4-methyl-4-hexenoate;

methyl (E)-6-(1,3-dihydro-4-(3,3-diphenyl)ureido-6-methoxy-7-methyl-3-oxoisobenzofuran-5-yl)-4-methyl-4-hexenoate;

methyl (E)-6-(1,3-dihydro-4-(3-phenyl)ureido-6-methoxy-7-methyl-3-oxoisobenzofuran-5-yl)-4-methyl-4-hexenoate, methyl (E)-6-(1,3-dihydro-4-(3-methyl-3-phenyl)ureido-6-methoxy-7-methyl-3-oxoisobenzofuran-5-yl)-4-methyl-4-hexenoate;

methyl (E)-6-(1,3-dihydro-4-(3-butyl-3-propyl)ureido-6-methoxy-7-methyl-3-oxoisobenzofuran-5-yl)-4-methyl-4-hexenoate; and methyl (E)-6-(1,3-dihydro-4-(3-(2-chlorophenyl)ureido)-6-methoxy-7-methyl-3-oxoisobenzofuran-5-yl)-4-methyl-4-hexenoate.

EXAMPLE 11

Preparation of Compounds of Formula (I)

11A. Formula IB where $R^1$ is hydrogen, $R^2$ is —C(O)NR$^4$R$^5$, where $R^4$ and $R^5$ are methyl, and $R^7$ is hydrogen To a solution of 0.3 g (0.74 mmol) of methyl (E)-6-[1,3-dihydro-4-(3,3-dimethylureido)-6-methoxy-7-methyl-3-oxoisobenzofuran-5-yl]-4-methyl-4-hexenoate in 7.4 ml 4:1 methanol:water was added 0.13 g (2.96 mmol) of lithium hydroxide monohydrate. The solution was heated at 50°–60° C. for 4 hours. Upon cooling, the reaction was partitioned between aqueous sodium hydrogen sulfate and ethyl acetate. The organic layer was washed with brine, dried over magnesium sulfate, and concentrated to (E)-6-[1,3-dihydro-4-(3,3-dimethylureido)-6-methoxy-7-methyl-3-oxoisobenzofuran-5-yl]-4-methyl-4-hexenoic acid. Recrystallization from hexane-ethyl acetate gave 0.27 g (0.7 mmol) of (E)-6-[1,3-dihydro-4-(3,3-dimethylureido)-6-methoxy-7-methyl-3-oxoisobenzofuran-5-yl]-4-methyl-4-hexenoic acid, mp 170°–190° C.

11B. Formula IB where $R^1$ and $R^7$ are Hydrogen and $R^2$ is —C(O)NR$^4$R$^5$, varying $R^4$ and $R^5$ Similarly, following the procedure of Example 11A above, but replacing methyl (E)-6-[1,3-dihydro-4-(3,3-dimethylureido)-6-methoxy-7-methyl-3-oxoisobenzofuran-5-yl]-4-methyl-4-hexenoate with:

methyl (E)-6-(1,3-dihydro-4-(3-methyl)ureido-6-methoxy-7-methyl-3-oxoisobenzofuran-5-yl)-4-methyl-4-hexenoate;

methyl (E)-6-(1,3-dihydro-4-ureido-6-methoxy-7-methyl-3-oxoisobenzofuran-5-yl)-4-methyl-4-hexenoate;

methyl (E)-6-(1,3-dihydro-4-(3,3-diethyl)ureido-6-methoxy-7-methyl-3-oxoisobenzofuran-5-yl)-4-methyl-4-hexenoate;

methyl (E)-6-(1,3-dihydro-4-(3-ethyl)ureido-6-methoxy-7-methyl-3-oxoisobenzofuran-5-yl)-4-methyl-4-hexenoate;

methyl (E)-6-(1,3-dihydro-4-(3-methyl-3-ethyl)ureido-6-methoxy-7-methyl-3-oxoisobenzofuran-5-yl)-4-methyl-4-hexenoate;

methyl (E)-6-(1,3-dihydro-4-(3,3-diphenyl)ureido-6-methoxy-7-methyl-3-oxoisobenzofuran-5-yl)-4-methyl-4-hexenoate;

methyl (E)-6-(1,3-dihydro-4-(3-phenyl)ureido-6-methoxy-7-methyl-3-oxoisobensofuran-5-yl)-4-methyl-4-hexenoate;

methyl (E)-6-(1,3-dihydro-4-(3-methyl-3-phenyl-)ureido-6-methoxy-7-methyl-3-oxoisobenzofuran-5-yl)-4-methyl-4-hexenoate;

methyl (E)-6-(1,3-dihydro-4-(3-butyl-3-propyl-)ureido-6-methoxy-7-methyl-3-oxoisobenzofuran-5-yl)-4-methyl-4-hexenoate;

methyl (E)-6-(1,3-dihydro-4-[3-(2-chlorophenyl-)ureido]-6-methoxy-7-methyl-3-oxoisobenzofuran-5-yl)-4-methyl-4-hexenoate;

there are obtained the following respective compounds:

(E)-6-[1,3-dihydro-4-(3-methyl)ureido-6-methoxy-7-methyl-3-oxoisobenzofuran-5-yl]-4-methyl-4-hexenoic acid;

(E)-6-(1,3-dihydro-4-ureido-6-methoxy-7-3-oxoisobenzofuran-5-yl)-4-methyl-4-hexenoic acid;

(E)-6-[1,3-dihydro-4-(3,3-diethyl)ureido-6-methoxy-7-methyl-3-oxoisobenzofuran-5-yl]-4-methyl-4-hexenoic acid;

(E)-6-[1,3-dihydro-4-(3-ethyl)ureido-6-methoxy-7-methyl-3-oxoisobenzofuran-5-yl]-4-methyl-4-hexenoic acid;

(E)-6-[1,3-dihydro-4-(3-methyl-3-ethyl)ureido-6-methoxy-7-methyl-3-oxoisobenzofuran-5-yl]-4-methyl-4-hexenoic acid;

(E)-6-[1,3-dihydro-4-(3,3-diphenyl)ureido-6-methoxy-7-methyl-3-oxoisobenzofuran-5-yl]-4-methyl-4-hexenoic acid;

(E)-6-[1,3-dihydro-4-(3-phenyl)ureido-6-methoxy-7-methyl-3-oxoisobenzofuran-5-yl]-4-methyl-4-hexenoic acid; and (E)-6-[1,3-dihydro-4-(3-methyl-3-phenyl)ureido-6-methoxy-7-methyl-3-oxoisobenzofuran-5-yl]-4-methyl-4-hexenoic acid.

EXAMPLE 12

Preparation of Compounds of Formula (I)

12A. Formula IB where $R^1$ is Hydrogen, $R^2$ is —C(O)$NR^4R^5$, and $R^7$ is Methyl, varying $R^4$ and $R^5$ By following the procedure of Example 8A above, but replacing E-6-(1,3-dihydro-4-amino-6-methoxy-7-methyl-3-oxoisobenzofuran-5-yl)-4-methyl-4-hexenoic acid with:

E-6-[1,3-dihydro-4-(3,3-dimethylureido)-6-methoxy-7-methyl-3-oxoisobenzofuran-5-yl]-4-methyl-4-hexenoic acid;

(E)-6-[1,3-dihydro-4-(3-methyl)ureido-6-methoxy-7-methyl-3-oxoisobenzofuran-5-yl]-4-methyl-4-hexenoic acid;

(E)-6-(1,3-dihydro-4-ureido-6-methoxy-7-methyl-3-oxoisobenzofuran-5-yl)-4-methyl-4-hexenoic acid;

(E)-6-[1,3-dihydro-4-(3,3-diethyl)ureido-6-methoxy-7-methyl-3-oxoisobenzofuran-5-yl]-4-methyl-4-hexenoic acid;

(E)-6-[1,3-dihydro-4-(3-ethyl)ureido-6-methoxy-7-methyl-3-oxoisobenzofuran-5-yl]-4-methyl-4-hexenoic acid;

(E)-6-[1,3-dihydro-4-(3-methyl-3-ethyl)ureido-6-methoxy-7-methyl-3-oxoisobenzofuran-5-yl]-4-methyl-4-hexenoic acid;

(E)-6-[1,3-dihydro-4-(3,3-diphenyl)ureido-6-methoxy-7-methyl-3-oxoisobenzofuran-5-yl]-4-methyl-4-hexenoic acid;

(E)-6-[1,3-dihydro-4-(3-phenyl)ureido-6-methoxy-7-methyl-3-oxoisobenzofuran-5-yl]-4-methyl-4-hexenoic acid; and (E)-6-[1,3-dihydro-4-(3-methyl-3-phenyl)ureido-6-methoxy-7-methyl-3-oxoisobenzofuran-5-yl]-4-methyl-4-hexenoic acid;

there are obtained the following respective compounds:

methyl E-6-[1,3-dihydro-4-(3,3-dimethylureido)-6-methoxy-7-methyl-3-oxoisobenzofuran-5-yl]-4-methyl-4-hexenoate;

methyl (E)-6-[1,3-dihydro-4-(3-methyl)ureido-6-methoxy-7-methyl-3-oxoisobenzofuran-5-yl]-4-methyl-4-hexenoate;

methyl (E)-6-(1,3-dihydro-4-ureido-6-methoxy-7-methyl-3-oxoisobenzofuran-5-yl)-4-methyl-4-hexenoate;

methyl (E)-6-[1,3-dihydro-4-(3,3-diethyl)ureido-6-methoxy-7-methyl-3-oxoisobenzofuran-5-yl]-4-methyl-4-hexenoate;

methyl (E)-6-[1,3-dihydro-4-(3-ethyl)ureido-6-methoxy-7-methyl-3-oxoisobenzofuran-5-yl]-4-methyl-4-hexenoate;

methyl (E)-6-[1,3-dihydro-4-(3-methyl-3-ethyl)ureido-6-methoxy-7-methyl-3-oxoisobenzofuran-5-yl]-4-methyl-4-hexenoate;

methyl (E)-6-[1,3-dihydro-4-(3,3-diphenyl)ureido-6-methoxy-7-methyl-3-oxoisobenzofuran-5-yl]-4-methyl-4-hexenoate;

methyl (E)-6-[1,3-dihydro-4-(3-phenyl)ureido-6-methoxy-7-methyl-3-oxoisobenzofuran-5-yl]-4-methyl-4-hexenoate; and methyl (E)-6-[1,3-dihydro-4-(3-methyl-3-phenyl)ureido-6-methoxy-7-methyl-3-oxoisobenzofuran-5-yl]-4-methyl-4-hexenoate.

12B. Formula IB where $R^1$ is hydrogen, $R^2$ is —C(O)$NR^4R^5$, varying $R^4$, $R^5$ and $R^7$ Similarly, following the procedure of Example 12A above, but replacing methanol with the following lower alkanols or optionally substituted phenols (other compounds of the formula $R^7OH$) (which may be commercially obtained or prepared by methods known to those skilled in the art):

ethanol, n-propanol, isopropanol, t-butanol, isoamyl alcohol, phenol, 2-chlorophenol, 2-trifluoromethylphenol, and 2-chloro-3,4-dimethoxyphenol;

there are obtained the following respective compounds:

ethyl (E)-6-[1,3-dihydro-4-(3,3-dimethylureido)-6-methoxy-7-methyl-3-oxoisobenzofuran-5-yl]-4-methyl-4-hexenoate;

n-propyl (E)-6-[1,3-dihydro-4-(3,3-dimethylureido)-6-methoxy-7-methyl-3-oxoisobenzofuran-5-yl]-4-methyl-4-hexenoate;

isopropyl (E)-6-[1,3-dihydro-4-(3,3-dimethylureido)-6-methoxy-7-methyl-3-oxoisobenzofuran-5-yl]-4-methyl-4-hexenoate;

t-butyl (E)-6-[1,3-dihydro-4-(3,3-dimethylureido)-6-methoxy-7-methyl-3-oxoisobenzofuran-5-yl]-4-methyl-4-hexenoate;

isoamyl (E)-6-[1,3-dihydro-4-(3,3-dimethylureido)-6-methoxy-7-methyl-3-oxoisobenzofuran-5-yl]-4-methyl-4-hexenoate;

phenyl (E)-6-[1,3-dihydro-4-(3,3-dimethylureido)-6-methoxy-7-methyl-3-oxoisobenzofuran-5-yl]-4-methyl-4-hexenoate;

2-chlorophenyl (E)-6-[1,3-dihydro-4-(3,3-dimethylureido)-6-methoxy-7-methyl-3-oxoisobenzofuran-5-yl]-4-methyl-4-hexenoate;

2-trifluoromethylphenyl (E)-6-[1,3-dihydro-4-(3,3-dimethylureido)-6-methoxy-7-methyl-3-oxoisobenzofuran-5-yl]-4-methyl-4-hexenoate;

2-chloro-3,4-dimethoxyphenyl (E)-6-[1,3-dihydro-4-(3,3-dimethylureido)-6-methoxy-7-methyl-3-oxoisobenzofuran-5-yl]-4-methyl-4-hexenoate;
ethyl (E)-6-[1,3-dihydro-4-(3-methyl)ureido-6-methoxy-7-methyl-3-oxoisobenzofuran-5-yl]-4-methyl-4-hexenoate;
n-propyl (E)-6-[1,3-dihydro-4-(3-methyl)ureido-6-methoxy-7-methyl-3-oxoisobenzofuran-5-yl]-4-methyl-4-hexenoate;
isopropyl (E)-6-[1,3-dihydro-4-(3-methyl)ureido-6-methoxy-7-methyl-3-oxoisobenzofuran-5-yl]-4-methyl-4-hexenoate;
t-butyl (E)-6-[1,3-dihydro-4-(3-methyl)ureido-6-methoxy-7-methyl-3-oxoisobenzofuran-5-yl]-4-methyl-4-hexenoate;
isoamyl (E)-6-[1,3-dihydro-4-(3-methyl)ureido-6-methoxy-7-methyl-3-oxoisobenzofuran-5-yl]-4-methyl-4-hexenoate;
phenyl (E)-6-[1,3-dihydro-4-(3-methyl)ureido-6-methoxy-7-methyl-3-oxoisobenzofuran-5-yl]-4-methyl-4-hexenoate;
2-chlorophenyl (E)-6-[1,3-dihydro-4-(3-methyl)ureido-6-methoxy-7-methyl-3-oxoisobenzofuran-5-yl]-4-methyl-4-hexenoate;
2-trifluoromethylphenyl (E)-6-[1,3-dihydro-4-(3-methyl)ureido-6-methoxy-7-methyl-3-oxoisobenzofuran-5-yl]-4-methyl-4-hexenoate;
2-chloro-3,4-dimethoxyphenyl (E)-6-[1,3-dihydro-4-(3-methyl)ureido-6-methoxy-7-methyl-3-oxoisobenzofuran-5-yl]-4-methyl-4-hexenoate;
ethyl (E)-6-(1,3-dihydro-4-ureido-6-methoxy-7-methyl-3-oxoisobenzofuran-5-yl)-4-methyl-4-hexenoate;
n-propyl (E)-6-(1,3-dihydro-4-ureido-6-methoxy-7-methyl-3-oxoisobenzofuran-5-yl)-4-methyl-4-hexenoate;
isopropyl (E)-6-(1,3-dihydro-4-ureido-6-methoxy-7-methyl-3-oxoisobenzofuran-5-yl)-4-methyl-4-hexenoate;
t-butyl (E)-6-(1,3-dihydro-4-ureido-6-methoxy-7-methyl-3-oxoisobenzofuran-5-yl)-4-methyl-4-hexenoate;
isoamyl (E)-6-(1,3-dihydro-4-ureido-6-methoxy-7-methyl-3-oxoisobenzofuran-5-yl)-4-methyl-4-hexenoate;
phenyl (E)-6-(1,3-dihydro-4-ureido-6-methoxy-7-methyl-3-oxoisobenzofuran-5-yl)-4-methyl-4-hexenoate;
2-chlorophenyl (E)-6-(1,3-dihydro-4-ureido-6-methoxy-7-methyl-3-oxoisobenzofuran-5-yl)-4-methyl-4-hexenoate;
2-trifluoromethylphenyl (E)-6-(1,3-dihydro-4-ureido-6-methoxy-7-methyl-3-oxoisobenzofuran-5-yl)-4-methyl-4-hexenoate;
2-chloro-3,4-dimethoxyphenyl (E)-6-(1,3-dihydro-4-ureido-6-methoxy-7-methyl-3-oxoisobenzofuran-5-yl)-4-methyl-4-hexenoate;
ethyl (E)-6-[1,3-dihydro-4-(3,3-diethyl)ureido-6-methoxy-7-methyl-3-oxoisobenzofuran-5-yl]-4-methyl-4-hexenoate;
n-propyl (E)-6-[1,3-dihydro-4-(3,3-diethyl)ureido-6-methoxy-7-methyl-3-oxoisobenzofuran-5-yl]-4-methyl-4-hexenoate;
isopropyl (E)-6-[1,3-dihydro-4-(3,3-diethyl)ureido-6-methoxy-7-methyl-3-oxoisobenzofuran-5-yl]-4-methyl-4-hexenoate;
t-butyl (E)-6-[1,3-dihydro-4-(3,3-diethyl)ureido-6-methoxy-7-methyl-3-oxoisobenzofuran-5-yl]-4-methyl-4-hexenoate;
isoamyl (E)-6-[1,3-dihydro-4-(3,3-diethyl)ureido-6-methoxy-7-methyl-3-oxoisobenzofuran-5-yl]-4-methyl-4-hexenoate;
phenyl (E)-6-[1,3-dihydro-4-(3,3-diethyl)ureido-6-methoxy-7-methyl-3-oxoisobenzofuran-5-yl]-4-methyl-4-hexenoate;
2-chlorophenyl (E)-6-[1,3-dihydro-4-(3,3-diethyl)ureido-6-methoxy-7-methyl-3-oxoisobenzofuran-5-yl]-4-methyl-4-hexenoate;
2-trifluoromethylphenyl (E)-6-[1,3-dihydro-4-(3,3-diethyl)ureido-6-methoxy-7-methyl-3-oxoisobenzofuran-5-yl]-4-methyl-4-hexenoate;
2-chloro-3,4-dimethoxyphenyl (E)-6-[1,3-dihydro-4-(3,3-diethyl)ureido-6-methoxy-7-methyl-3-oxoisobenzofuran-5-yl]-4-methyl-4-hexenoate;
ethyl (E)-6-[1,3-dihydro-4-(3-ethyl)ureido-6-methoxy-7-methyl-3-oxoisobenzofuran-5-yl]-4-methyl-4-hexenoate;
n-propyl (E)-6-[1,3-dihydro-4-(3-ethyl)ureido-6-methoxy-7-methyl-3-oxoisobenzofuran-5-yl]-4-methyl-4-hexenoate;
isopropyl (E)-6-[1,3-dihydro-4-(3-ethyl)ureido-6-methoxy-7-methyl-3-oxoisobenzofuran-5-yl]-4-methyl-4-hexenoate;
t-butyl (E)-6-[1,3-dihydro-4-(3-ethyl)ureido-6-methoxy-7-methyl-3-oxoisobenzofuran-5-yl]-4-methyl-4-hexenoate;
isoamyl (E)-6-[1,3-dihydro-4-(3-ethyl)ureido-6-methoxy-7-methyl-3-oxoisobenzofuran-5-yl]-4-methyl-4-hexenoate;
phenyl (E)-6-[1,3-dihydro-4-(3-ethyl)ureido-6-methoxy-7-methyl-3-oxoisobenzofuran-5-yl]-4-methyl-4-hexenoate;
2-chlorophenyl (E)-6-[1,3-dihydro-4-(3ethyl)ureido-6-methoxy-7-methyl-3-oxoisobenzofuran-5-yl]-4-methyl-4-hexenoate;
2-trifluoromethylphenyl (E)-6-[1,3-dihydro-4-(3-ethyl)ureido-6-methoxy-7-methyl-3-oxoisobenzofuran-5-yl]-4-methyl-4-hexenoate;
2-chloro-3,4-dimethoxyphenyl (E)-6-[1,3-dihydro-4-(3-ethyl)ureido-6-methoxy-7-methyl-3-oxoisobenzofuran-5-yl]-4-methyl-4-hexenoate;
ethyl (E)-6-[1,3-dihydro-4-(3-methyl-3-ethyl)ureido-6-methoxy-7-methyl-3-oxoisobenzofuran-5-yl]-4-methyl-4-hexenoate;
n-propyl (E)-6-[1,3-dihydro-4-(3-methyl-3-ethyl)ureido-6-methoxy-7-methyl-3-oxoisobenzofuran-5-yl]-4-methyl-4-hexenoate;
isopropyl (E)-6-[1,3-dihydro-4-(3-methyl-3-ethyl)ureido-6-methoxy-7-methyl-3-oxoisobenzofuran-5-yl]-4-methyl-4-hexenoate;
t-butyl (E)-6-[1,3-dihydro-4-(3-methyl-methyl-3-ethyl)ureido-6-methoxy-7-methyl-3-oxoisobenzofuran-5-yl]-4-methyl-4-hexenoate;
isoamyl (E)-6-[1,3-dihydro-4-(3-methyl-3-ethyl)ureido-6-methoxy-7-methyl-3-oxoisobenzofuran-5-yl]-4-methyl-4-hexenoate;
phenyl (E)-6-[1,3-dihydro-4-(3-methyl-3-ethyl)ureido-6-methoxy-7-methyl-3-oxoisobenzofuran-5-yl]-4-methyl-4-hexenoate;
2-chlorophenyl (E)-6-[1,3-dihydro-4-(3-methyl-3-ethyl)ureido-6-methoxy-7-methyl-3-oxoisobenzofuran-5-yl]-4-methyl-4-hexenoate;
2-trifluoromethylphenyl (E)-6-[1,3-dihydro-4-(3-methyl-3-ethyl)ureido-6-methoxy-7-methyl-3-oxoisobenzofuran-5-yl]-4-methyl-4-hexenoate;

2-chloro-3,4-dimethoxyphenyl(E)-6-[1,3-dihydro-4-(3-methyl-3-ethyl)ureido-6-methoxy-7-methyl-3-oxoisobenzofuran-5-yl]-4-methyl-4-hexenoate;

ethyl (E)-6-[1,3-dihydro-4-(3,3-diphenyl)ureido-6-methoxy-7-methyl-3-oxoisobenzofuran-5-yl]-4-methyl-4-hexenoate;

n-propyl (E)-6-[1,3-dihydro-4-(3,3-diphenyl)ureido-6-methoxy-7-methyl-3-oxoisobenzofuran-5-yl]-4-methyl-4-hexenoate;

isopropyl (E)-6-[1,3-dihydro-4-(3,3-diphenyl)ureido-6-methoxy-7-methyl-3-oxoisobenzofuran-5-yl]-4-methyl-4-hexenoate;

t-butyl (E)-6-[1,3-dihydro-4-(3,3-diphenyl)ureido-6-methoxy-7-methyl-3-oxoisobenzofuran-5-yl]-4-methyl-4-hexenoate;

isoamyl (E)-6-[1,3-dihydro-4-(3,3-diphenyl)ureido-6-methoxy-7-methyl-3-oxoisobenzofuran-5-yl]-4-methyl-4-hexenoate;

phenyl (E)-6-[1,3-dihydro-4-(3,3-diphenyl)ureido-6-methoxy-7-methyl-3-oxoisobenzofuran-5-yl]-4-methyl-4-hexenoate;

2-chlorophenyl (E)-6-[1,3-dihydro-4-(3,3-diphenyl)ureido-6-methoxy-7-methyl-3-oxoisobenzofuran-5-yl]-4-methyl-4-hexenoate;

2-trifluoromethylphenyl (E)-6-[1,3-dihydro-4-(3,3-diphenyl)ureido-6-methoxy-7-methyl-3-oxoisobenzofuran-5-yl]-4-methyl-4-hexenoate;

2-chloro-3,4-dimethoxyphenyl (E)-6-[1,3-dihydro-4-(3,3-diphenyl)ureido-6-methoxy-7-methyl-3-oxoisobenzofuran-5-yl]-4-methyl-4-hexenoate;

ethyl (E)-6-[1,3-dihydro-4-(3-phenyl)ureido-6-methoxy-7-methyl-3-oxoisobenzofuran-5-yl]-4-methyl-4-hexenoate;

n-propyl (E)-6-[1,3-dihydro-4-(3-phenyl)ureido-6-methoxy-7-methyl-3-oxoisobenzofuran-5-yl]-4-methyl-4-hexenoate;

isopropyl (E)-6-[1,3-dihydro-4-(3-phenyl)ureido-6-methoxy-7-methyl-3-oxoisobenzofuran-5-yl]-4-methyl-4-hexenoate;

t-butyl (E)-6-[1,3-dihydro-4-(3-phenyl)ureido-6-methoxy-7-methyl-3-oxoisobenzofuran-5-yl]-4-methyl-4-hexenoate;

isoamyl (E)-6-[1,3-dihydro-4-(3-phenyl)ureido-6-methoxy-7-methyl-3-oxoisobenzofuran-5-yl]-4-methyl-4-hexenoate;

phenyl (E)-6-[1,3-dihydro-4-(3-phenyl)ureido-6-methoxy-7-methyl-3-oxoisobenzofuran-5-yl]-4-methyl-4-hexenoate;

2-chlorophenyl (E)-6-[1,3-dihydro-4-(3-phenyl)ureido-6-methoxy-7-methyl-3-oxoisobenzofuran-5-yl]-4-methyl-4-hexenoate;

2-trifluoromethylphenyl (E)-6-[1,3-dihydro-4-(3-phenyl)ureido-6-methoxy-7-methyl-3-oxoisobenzofuran-5-yl]-4-methyl-4-hexenoate;

2-chloro-3,4-dimethoxyphenyl (E)-6-[1,3-dihydro-4-(3-phenyl)ureido-6-methoxy-7-methyl-3-oxoisobenzofuran-5-yl]-4-methyl-4-hexenoate;

ethyl (E)-6-[1,3-dihydro-4-(3-phenyl)ureido-6-methoxy-7-methyl-3-oxoisobenzofuran-5-yl]-4-methyl-4-hexenoate;

n-propyl (E)-6-[1,3-dihydro-4-(3-methyl-3-phenyl)ureido-6-methoxy-7-methyl-3-oxoisobenzofuran-5-yl]-4-methyl-4-hexenoate;

isopropyl (E)-6-[1,3-dihydro-4-(3-methyl-3-phenyl)ureido-6-methoxy-7-methyl-3-oxoisobenzofuran-5-yl]-4-methyl-4-hexenoate;

t-butyl (E)-6-[1,3-dihydro-4-(3-methyl-3-phenyl)ureido-6-methoxy-7-methyl-3-oxoisobenzofuran-5-yl]-4-methyl-4-hexenoate;

isoamyl (E)-6-[1,3-dihydro-4-(3-methyl-3-phenyl)ureido-6-methoxy-7-methyl-3-oxoisobenzofuran-5-yl]-4-methyl-4-hexenoate;

phenyl (E)-6-[1,3-dihydro-4-(3-methyl-3-phenyl)ureido-6-methoxy-7-methyl-3-oxoisobenzofuran-5-yl]-4-methyl-4-hexenoate;

2-chlorophenyl (E)-6-[1,3-dihydro-4-(3-methyl-3-phenyl)ureido-6-methoxy-7-methyl-3-oxoisobenzofuran-5-yl]-4-methyl-4-hexenoate;

2-trifluoromethylphenyl (E)-6-[1,3-dihydro-4-(3-methyl-3-phenyl)ureido-6-methoxy-7-methyl-3-oxoisobenzofuran-5-yl]-4-methyl-4-hexenoate;

2-chloro-3,4-dimethoxyphenyl (E)-6-[1,3-dihydro-4-(3-methyl-3-phenyl)ureido-6-methoxy-7-methyl-3-oxoisobenzofuran-5-yl]-4-methyl-4-hexenoate;

ethyl (E)-6-[1,3-dihydro-4-(3-butyl-3-propyl)ureido-6-methoxy-7-methyl-3-oxoisobenzofuran-5-yl]-4-methyl-4-hexenoate;

n-propyl (E)-6-[1,3-dihydro-4-(3-butyl-3-propyl)ureido-6-methoxy-7-methyl-3-oxoisobenzofuran-5-yl]-4-methyl-4-hexenoate;

isopropyl (E)-6-[1,3-dihydro-4-(3-butyl-3-propyl)ureido-6-methoxy-7-methyl-3-oxoisobenzofuran-5-yl]-4-methyl-4-hexenoate;

t-butyl (E)-6-[1,3-dihydro-4-(3-butyl-3-propyl)ureido-6-methoxy-7-methyl-3-oxoisobenzofuran-5-yl]-4-methyl-4-hexenoate;

isoamyl (E)-6-[1,3-dihydro-4-(3-butyl-3-propyl)ureido-6-methoxy-7-methyl-3-oxoisobenzofuran-5-yl]-4-methyl-4-hexenoate;

phenyl (E)-6-[1,3-dihydro-4-(3-butyl-3-propyl)ureido-6-methoxy-7-methyl-3-oxoisobenzofuran-5-yl]-4-methyl-4-hexenoate;

2-chlorophenyl (E)-6-[1,3-dihydro-4-(3-butyl-3-propyl)ureido-6-methoxy-7-methyl-3-oxoisobenzofuran-5-yl]-4-methyl-4-hexenoate;

2-trifluoromethylphenyl (E)-6-[1,3-dihydro-4-(3-butyl-3-propyl)ureido-6-methoxy-7-methyl-3-oxoisobenzofuran-5-yl]-4-methyl-4-hexenoate;

2-chloro-3,4-dimethoxyphenyl (E)-6-[1,3-dihydro-4-(3-propyl)ureido-6-methoxy-7-methyl-3-oxoisobenzofuran-5-yl]-4-methyl-4-hexenoate;

ethyl (E)-6-[1,3-dihydro-4-(3-(2-chlorophenyl)ureido)-6-methoxy-7-methyl-3-oxoisobenzofuran-5-yl]-4-methyl-4-hexenoate;

n-propyl (E)-6-[1,3-dihydro-4-(3-(2-chlorophenyl)ureido)-6-methoxy-7-methyl-3-oxoisobenzofuran-5-yl]-4-methyl-4-hexenoate;

isopropyl (E)-6-[1,3-dihydro-4-(3-(2-chlorophenyl)ureido)-6-methoxy-7-methyl-3-oxoisobenzofuran-5-yl]-4-methyl-4-hexenoate;

t-butyl (E)-6-[1,3-dihydro-4-(3-(2-chlorophenyl)ureido)-6-methoxy-7-methyl-3-oxoisobenzofuran-5-yl]-4-methyl-4-hexenoate;

isoamyl (E)-6-[1,3-dihydro-4-(3-(2-chlorophenyl)ureido)-6-methoxy-7-methyl-3-oxoisobenzofuran-5-yl]-4-methyl-4-hexenoate;

phenyl (E)-6-[1,3-dihydro-4-(3-(2-chlorophenyl)ureido)-6-methoxy-7-methyl-3-oxoisobenzofuran-5-yl]-4-methyl-4-hexenoate;

2-chlorophenyl (E)-6-[1,3-dihydro-4-(3-(2-chlorophenyl)ureido)-6-methoxy-7-methyl-3-oxoisobenzofuran-5-yl]-4-methyl-4-hexenoate;

2-trifluoromethylphenyl (E)-6-[1,3-dihydro-4-(3-(2-chlorophenyl)ureido)-6-methoxy-7-methyl-3-oxoisobenzofuran-5-yl]-4-methyl-4-hexenoate; and 2-chloro-3,4-dimethoxyphenyl (E)-6-[1,3-dihydro-4-(3-(2-chlorophenyl)ureido)-6-methoxy-7-methyl-3-oxoisobenzofuran-5-yl]-4-methyl-4-hexenoate.

EXAMPLE 13

Preparation of Compounds of Formula (I)

13A. Formula IB where $R^1$ is Hydrogen, $R^2$ is —C(O)NR$^4$R$^5$, and $R^7$ is Morpholinoethyl, varying $R^4$ and $R^5$ Similarly, by following the procedure of Example 9A above, but replacing E-6-(1,3-dihydro-4-amino-6-methoxy-7-methyl-3-oxoisobenzofuran-5-yl)-4-methyl-4-hexenoic acid with:

E-6-[1,3-dihydro-4-(3,3-dimethylureido)-6-methoxy-7-methyl-3-oxoisobenzofuran-5-yl]-4-methyl-4-hexenoic acid;

(E)-6-[1,3-dihydro-4-(3-methyl)ureido-6-methoxy-7-methyl-3-oxoisobenzofuran-5-yl]-4-methyl-4-hexenoic acid;

(E)-6-(1,3-dihydro-4-ureido-6-methoxy-7-methyl-3-oxoisobenzofuran-5-yl)-4-methyl-4-hexenoic acid;

(E)-6-[1,3-dihydro-4-(3,3-diethyl)ureido-6-methoxy-7-methyl-3-oxoisobenzofuran-5-yl]-4-methyl-4-hexenoic acid;

(E)-6-[1,3-dihydro-4-(3-ethyl)ureido-6-methoxy-7-methyl-3-oxoisobenzofuran-5-yl]-4-methyl-4-hexenoic acid;

(E)-6-[1,3-dihydro-4-(3-methyl-3-ethyl)ureido-6-methoxy-7-methyl-3-oxoisobenzofuran-5-yl]-4-methyl-4-hexenoic acid;

(E)-6-[1,3-dihydro-4-(3,3-diphenyl)ureido-6-methoxy-7-methyl-3-oxoisobenzofuran-5-yl]-4-methyl-4-hexenoic acid;

(E)-6-[1,3-dihydro-4-(3-phenyl)ureido-6-methoxy-7-methyl-3-oxoisobenzofuran-5-yl]-4-methyl-4-hexenoic acid; and (E)-6-[1,3-dihydro-4-(3-methyl-3-phenyl)ureido-6-methoxy-7-methyl-3-oxoisobenzofuran-5-yl]-4-methyl-4-hexenoic acid; there are obtained the following respective compounds:

2-(morpholin-4-yl)ethyl E-6-[1,3-dihydro-4-(3,3-dimethylureido)-6-methoxy-7-methyl-3-oxoisobenzofuran-5-yl]-4-methyl-4-hexenoate;

2-(morpholin-4-yl)ethyl (E)-6-[1,3-dihydro-4-(3-methyl)ureido-6-methoxy-7-methyl-3-oxoisobenzofuran-5-yl]-4-methyl-4-hexenoate;

2-(morpholin-4-yl)ethyl (E)-6-(1,3-dihydro-4-ureido-6-methoxy-7-methyl-3-oxoisobenzofuran-5-yl)-4-methyl-4-hexenoate;

2-(morpholin-4-yl)ethyl (E)-6-[1,3-dihydro-4-(3,3-diethyl)ureido-6-methoxy-7-methyl-3-oxoisobenzofuran-5-yl]-4-methyl-4-hexenoate;

2-(morpholin-4-yl)ethyl (E)-6-[1,3-dihydro-4-(3-ethyl)ureido-6-methoxy-7-methyl-3-oxoisobenzofuran-5-yl]-4-methyl-4-hexenoate;

2-(morpholin-4-yl)ethyl (E)-6-[1,3-dihydro-4-(3-methyl-3-ethyl)ureido-6-methoxy-7-methyl-3-oxoisobenzofuran-5-yl]-4-methyl-4-hexenoate;

2-(morpholin-4-yl)ethyl (E)-6-[1,3-dihydro-4-(3,3-diphenyl)ureido-6-methoxy-7-methyl-3-oxoisobenzofuran-5-yl]-4-methyl-4-hexenoate;

2-(morpholin-4-yl)ethyl (E)-6-[1,3-dihydro-4-(3-phenyl)ureido-6-methoxy-7-methyl-3-oxoisobenzofuran-5-yl]-4-methyl-4-hexenoate; and 2-(morpholin-4-yl)ethyl (E)-6-[1,3-dihydro-4-(3-methyl-3-phenyl)ureido-6-methoxy-7-methyl-3-oxoisobenzofuran-5-yl]-4-methyl-4-hexenoate.

13B. Formula IB where $R^1$ is Hydrogen, $R^2$ is —C(O)NR$^4$R$^5$, varying $R^4$, $R^5$ and $R^7$ Similarly, following the procedure of Example 13A above, but replacing morpholinoethanol with the following heterocyclic aminoalkyl alcohols (other compounds of the formula R$^7$OH) (which may be commercially obtained or prepared by methods known to those skilled in the art):

2-(pyrrolidin-1-yl)ethanol;
2-(piperidin-1-yl)ethanol;
2-(thiazolidin-3-yl)ethanol;
3-(morpholin-4-yl)propanol;
4-(morpholin-4-yl)butanol;
2-(imidazolidin-1-yl)ethanol; and
2-(2-methyl-1,2-pyrazolidin-1-yl)ethanol;

there are obtained the following respective compounds:

2-(pyrrolidin-1-yl)ethyl (E)-6-[1,3-dihydro-4-(3,3-dimethylureido)-6-methoxy-7-methyl-3-oxoisobenzofuran-5-yl]-4-methyl-4-hexenoate;

2-(piperidin-1-yl)ethyl (E)-6-[1,3-dihydro-4-(3,3-dimethylureido)-6-methoxy-7-methyl-3-oxoisobenzofuran-5-yl]-4-methyl-4-hexenoate;

2-(thiazolidin-3-yl)ethyl (E)-6-[1,3-dihydro-4-(3,3-dimethylureido)-6-methoxy-7-methyl-3-oxoisobenzofuran-5-yl]-4-methyl-4-hexenoate;

3-(morpholin-4-yl)propyl (E)-6-[1,3-dihydro-4-(3,3-dimethylureido)-6-methoxy-7-methyl-3-oxoisobenzofuran-5-yl]-4-methyl-4-hexenoate;

4-(morpholin-4-yl)butyl (E)-6-[1,3-dihydro-4-(3,3-dimethylureido)-6-methoxy-7-methyl-3-oxoisobenzofuran-5-yl]-4-methyl-4-hexenoate;

2-(imidazolidin-1-yl)ethyl (E)-6-[1,3-dihydro-4-(3,3-dimethylureido)-6-methoxy-7-methyl-3-oxoisobenzofuran-5-yl]-4-methyl-4-hexenoate;

2-(2-methyl-1,2-pyrazolidin-1-yl)ethyl (E)-6-[1,3-dihydro-4-(3,3-dimethylureido)-6-methoxy-7-methyl-3-oxoisobenzofuran-5-yl]-4-methyl-4-hexenoate;

2-(pyrrolidin-1-yl)ethyl (E)-6-[1,3-dihydro-4-(3-methyl)ureido-6-methoxy-7-methyl-3-oxoisobenzofuran-5-yl]-4-methyl-4-hexenoate;

2-(piperidin-1-yl)ethyl (E)-6-[1,3-dihydro-4-(3-methyl)ureido-6-methoxy-7-methyl-3-oxoisobenzofuran-5-yl]-4-methyl-4-hexenoate;

2-(thiazolidin-3-yl)ethyl (E)-6-[1,3-dihydro-4-(3-methyl)ureido-6-methoxy-7-methyl-3-oxoisobenzofuran-5-yl]-4-methyl-4-hexenoate;

3-(morpholin-4-yl)propyl (E)-6-[1,3-dihydro-4-(3-methyl)ureido-6-methoxy-7-methyl-3-oxoisobenzofuran-5-yl]-4-methyl-4-hexenoate;

4-(morpholin-4-yl)butyl (E)-6-[1,3-dihydro-4-(3-methyl)ureido-6-methoxy-7-methyl-3-oxoisobenzofuran-5-yl]-4-methyl-4-hexenoate;

2-(imidazolidin-1-yl)ethyl (E)-6-[1,3-dihydro-4-(3-methyl)ureido-6-methoxy-7-methyl-3-oxoisobenzofuran-5-yl]-4-methyl-4-hexenoate;

2-(2-methyl-1,2-pyrazolidin-1-yl)ethyl (E)-6-[1,3-dihydro-4-(3-methyl)ureido-6-methoxy-7-methyl-3-oxoisobenzofuran-5-yl]-4-methyl-4-hexenoate;

2-(pyrrolidin-1-yl)ethyl (E)-6-(1,3-dihydro-4-ureido-6-methoxy-7-methyl-3-oxoisobenzofuran-5-yl)-4-methyl-4-hexenoate;

2-(piperidin-1-yl)ethyl (E)-6-(1,3-dihydro-4-ureido-6-methoxy-7-methyl-3-oxoisobenzofuran-5-yl)-4-methyl-4-hexenoate;

2-(thiazolidin-3-yl)ethyl (E)-6-(1,3-dihydro-4-ureido-6-methoxy-7-methyl-3-oxoisobenzofuran-5-yl)-4-methyl-4-hexenoate;

3-(morpholin-4-yl)propyl (E)-6-(1,3-dihydro-4-ureido-6-methoxy-7-methyl-3-oxoisobenzofuran-5-yl)-4-methyl-4-hexenoate;

4-(morpholin-4-yl)butyl (E)-6-(1,3-dihydro-6-methoxy-7-methyl-3-oxoisobenzofuran-5-yl)-4-methyl-4-hexenoate;

2-(imidazolidin-1-yl)ethyl (E)-6-(1,3-dihydro-4-ureido-6-methoxy-7-methyl-3-oxoisobenzofuran-5-yl)-4-methyl-4-hexenoate;

2-(2-methyl-1,2-pyrazolidin-1-yl)ethyl (E)-6-(1,3-dihydro-4-ureido-6-methoxy-7-methyl-3-oxoisobenzofuran-5-yl)-4-methyl-4-hexenoate;

2-(pyrrolidin-1-yl)ethyl (E)-6-[1,3-dihydro-4-(3,3-diethyl)ureido-6-methoxy-7-methyl-3-oxoisobenzofuran-5-yl]-4-methyl-4-hexenoate;

2-(piperidin-1-yl)ethyl (E)-6-[1,3-dihydro-4-(3,3-diethyl)ureido-6-methoxy-7-methyl-3-oxoisobenzofuran-5-yl]-4-methyl-4-hexenoate;

2-(thiazolidin-3-yl)ethyl (E)-6-[1,3-dihydro-4-(3,3-diethyl)ureido-6-methoxy-7-methyl-3-oxoisobenzofuran-5-yl]-4-methyl-4-hexenoate;

3-(morpholin-4-yl)propyl (E)-6-[1,3-dihydro-4-(3,3-diethyl)ureido-6-methoxy-7-methyl-3-oxoisobenzofuran-5-yl]-4-methyl-4-hexenoate;

4-(morpholin-4-yl)butyl (E)-6-[1,3-dihydro-4-(3,3-diethyl)ureido-6-methoxy-7-methyl-3-oxoisobenzofuran-5-yl]-4-methyl-4-hexenoate;

2-(imidazolidin-1-yl)ethyl (E)-6-[1,3-dihydro-4-(3,3-diethyl)ureido-6-methoxy-7-methyl-3-oxoisobenzofuran-5-yl]-4-methyl-4-hexenoate;

2-(2-methyl-1,2-pyrazolidin-1-yl)ethyl (E)-6-[1,3-dihydro-4-(3,3-diethyl)ureido-6-methoxy-7-methyl-3-oxoisobenzofuran-5-yl]-4-methyl-4-hexenoate;

2-(pyrrolidin-1-yl)ethyl (E)-6-[1,3-dihydro-4-(3-ethyl)ureido-6-methoxy-7-methyl-3-oxoisobenzofuran-5-yl]-4-methyl-4-hexenoate;

2-(piperidin-1-yl)ethyl (E)-6-[1,3-dihydro-4-(3-ethyl)ureido-6-methoxy-7-methyl-3-oxoisobenzofuran-5-yl]-4-methyl-4-hexenoate;

2-(thiazolidin-3-yl)ethyl (E)-6-[1,3-dihydro-4-(3-ethyl)ureido-6-methoxy-7-methyl-3-oxoisobenzofuran-5-yl]-4-methyl-4-hexenoate;

3-(morpholin-4-yl)propyl (E)-6-[1,3-dihydro-4-(3-ethyl)ureido-6-methoxy-7-methyl-3-oxoisobenzofuran-5-yl]-4-methyl-4-hexenoate;

4-(morpholin-4-yl)butyl (E)-6-[1,3-dihydro-4-(3-ethyl)ureido-6-methoxy-7-methyl-3-oxoisobenzofuran-5-yl]-4-methyl-4-hexenoate;

2-(imidazolidin-1-yl)ethyl (E)-6-[1,3-dihydro-4-(3-ethyl)ureido-6-methoxy-7-methyl-3-oxoisobenzofuran-5-yl]-4-methyl-4-hexenoate;

2-(2-methyl-1,2-pyrazolidin-1-yl)ethyl (E)-6-[1,3-dihydro-4-(3-ethyl)ureido-6-methoxy-7-methyl-3-oxoisobenzofuran-5-yl]-4-methyl-4-hexenoate;

2-(pyrrolidin-1-yl)ethyl (E)-6-[1,3-dihydro-4-(3-methyl-3-ethyl)ureido-6-methoxy-7-methyl-3-oxoisobenzofuran-5-yl)]-4-methyl-4-hexenoate;

2-(piperidin-1-yl)ethyl (E)-6-[1,3-dihydro-4-(3-methyl-3-ethyl)ureido-6-methoxy-7-methyl-3-oxoisobenzofuran-5-yl]-4-methyl-4-hexenoate;

2-(thiazolidin-3-yl)ethyl (E)-6-[1,3-dihydro-4-(3-methyl-3-ethyl)ureido-6-methoxy-7-methyl-3-oxoisobenzofuran-5-yl]-4-methyl-4-hexenoate;

3-(morpholin-4-yl)propyl (E)-6-[1,3-dihydro-4-(3-methyl-3-ethyl)ureido-6-methoxy-7-methyl-3-oxoisobenzofuran-5-yl]-4-methyl-4-hexenoate;

4-(morpholin-4-yl)butyl (E)-6-[1,3-dihydro-4-(3-methyl-3-ethyl)ureido-6-methoxy-7-methyl-3-oxoisobenzofuran-5-yl]-4-methyl-4-hexenoate;

2-(imidazolidin-1-yl)ethyl (E)-6-[1,3-dihydro-4-(3-methyl-3-ethyl)ureido-6-methoxy-7-methyl-3-oxoisobenzofuran-5-yl]-4-methyl-4-hexenoate;

2-(2-methyl-1,2-pyrazolidin-1-yl)ethyl (E)-6-[1,3-dihydro-4-(3-methyl-3-ethyl)ureido-6-methoxy-7-methyl-3-oxoisobenzofuran-5-yl]-4-methyl-4-hexenoate;

2-(pyrrolidin-1-yl)ethyl (E)-6-[1,3-dihydro-4-(3,3-diphenyl)ureido-6-methoxy-7-methyl-3-oxoisobenzofuran-5-yl]-4-methyl-4-hexenoate;

2-(piperidin-1-yl)ethyl (E)-6-[1,3-dihydro-4-(3,3-diphenyl)ureido-6-methoxy-7-methyl-3-oxoisobenzofuran-5-yl]-4-methyl-4-hexenoate;

2-(thiazolidin-3-yl)ethyl (E)-6-[1,3-dihydro-4-(3,3-diphenyl)ureido-6-methoxy-7-methyl-3-oxoisobenzofuran-5-yl]-4-methyl-4-hexenoate;

3-(morpholin-4-yl)propyl (E)-6-[1,3-dihydro-4-(3,3-diphenyl)ureido-6-methoxy-7-methyl-3-oxoisobenzofuran-5-yl]-4-methyl-4-hexenoate;

4-(morpholin-4-yl)butyl (E)-6-[1,3-dihydro-4-(3,3-diphenyl)ureido-6-methoxy-7-methyl-3-oxoisobenzofuran-5-yl]-4-methyl-4-hexenoate;

2-(imidazolidin-1-yl)ethyl (E)-6-[1,3-dihydro-4-(3,3-diphenyl)ureido-6-methoxy-7-methyl-3-oxoisobenzofuran-5-yl]-4-methyl-4-hexenoate;

2-(2-methyl-1,2-pyrazolidin-1-yl)ethyl (E)-6-[1,3-dihydro-4-(3,3-diphenyl)ureido-6-methoxy-7-methyl-3-oxoisobenzofuran-5-yl]-4-methyl-4-hexenoate;

2-(pyrrolidin-1-yl)ethyl (E)-6-[1,3-dihydro-4-(3-phenyl)ureido-6-methoxy-7-methyl-3-oxoisobenzofuran-5-yl]-4-methyl-4-hexenoate;

2-(piperidin-1-yl)ethyl (E)-6-[1,3-dihydro-4-(3-phenyl)ureido-6-methoxy-7-methyl-3-oxoisobenzofuran-5-yl]-4-methyl-4-hexenoate;

2-(thiazolidin-3-yl)ethyl (E)-6-[1,3-dihydro-4-(3-phenyl)ureido-6-methoxy-7-methyl-3-oxoisobenzofuran-5-yl]-4-methyl-4-hexenoate;

3-(morpholin-4-yl)propyl (E)-6-[1,3-dihydro-4-(3-phenyl)ureido-6-methoxy-7-methyl-3-oxoisobenzofuran-5-yl]-4-methyl-4-hexenoate;

4-(morpholin-4-yl)butyl (E)-6-[1,3-dihydro-4-(3-phenyl)ureido-6-methoxy-7-methyl-3-oxoisobenzofuran-5-yl]-4-methyl-4-hexenoate;

2-(imidazolidin-1-yl)ethyl (E)-6-[1,3-dihydro-4-(3-phenyl)ureido-6-methoxy-7-methyl-3-oxoisobenzofuran-5-yl]-4-methyl-4-hexenoate;

2-(2-methyl-1,2-pyrazolidin-1-yl)ethyl (E)-6-[1,3-dihydro-4-(3-phenyl)ureido-6-methoxy-7-methyl-3-oxoisobenzofuran-5-yl]-4-methyl-4-hexenoate;

2-(pyrrolidin-1-yl)ethyl (E)-6-[1,3-dihydro-4-(3-methyl-3-phenyl)ureido-6-methoxy-7-methyl-3-oxoisobenzofuran-5-yl]-4-methyl-4-hexenoate;

2-(piperidin-1-yl)ethyl (E)-6-[1,3-dihydro-4-(3-methyl-3-phenyl)ureido-6-methoxy-7-methyl-3-oxoisobenzofuran-5-yl]-4-methyl-4-hexenoate;

2-(thiazolidin-3-yl)ethyl (E)-6-[1,3-dihydro-4-(3-methyl-3-phenyl)ureido-6-methoxy-7-methyl-3-oxoisobenzofuran-5-yl]-4-methyl-4-hexenoate;

3-(morpholin-4-yl)propyl (E)-6-[1,3-dihydro-4-(3-methyl-3-phenyl)ureido-6-methoxy-7-methyl-3-oxoisobenzofuran-5-yl]-4-methyl-4-hexenoate;

4-(morpholin-4-yl)butyl (E)-6-[1,3-dihydro-4-(3-methyl-3-phenyl)ureido-6-methoxy-7-methyl-3-oxoisobenzofuran-5-yl]-4-methyl-4-hexenoate;
2-(imidazolidin-1-yl)ethyl (E)-6-[1,3-dihydro-4-(3-methyl-3-phenyl)ureido-6-methoxy-7-methyl-3-oxoisobenzofuran-5-yl]-4-methyl-4-hexenoate;
2-(2-methyl-1,2-pyrazolidin-1-yl)ethyl (E)-6-[1,3-dihydro-4-(3-methyl-3-phenyl)ureido-6-methoxy-7-methyl-3-oxoisobenzofuran-5-yl]-4-methyl-4-hexenoate;
2-(pyrrolidin-1-yl)ethyl (E)-6-[1,3-dihydro-4-(3-butyl-3-propyl)ureido-6-methoxy-7-methyl-3-oxoisobenzofuran-5-yl]-4-methyl-4-hexenoate;
2-(piperidin-1-yl)ethyl (E)-6-[1,3-dihydro-4-(3-butyl-3-propyl)ureido-6-methoxy-7-methyl-3-oxoisobenzofuran-5-yl]-4-methyl-4-hexenoate;
2-(thiazolidin-3-yl)ethyl (E)-6-[1,3-dihydro-4-(3-butyl-3-propyl)ureido-6-methoxy-7-methyl-3-oxoisobenzofuran-5-yl]-4-methyl-4-hexenoate;
3-(morpholin-4-yl)propyl (E)-6-[1,3-dihydro-4-(3-butyl-3-propyl)ureido-6-methoxy-7-methyl-3-oxoisobenzofuran-5-yl]-4-methyl-4-hexenoate;
4-(morpholin-4-yl)butyl (E)-6-[1,3-dihydro-4-(3-butyl-3-propyl)ureido-6-methoxy-7-methyl-3-oxoisobenzofuran-5-yl]-4-methyl-4-hexenoate;
2-(imidazolidin-1-yl)ethyl (E)-6-[1,3-dihydro-4-(3-butyl-3-propyl)ureido-6-methoxy-7-methyl-3-oxoisobenzofuran-5-yl]-4-methyl-4-hexenoate;
2-(2-methyl-1,2-pyrazolidin-1-yl)ethyl (E)-6-[1,3-dihydro-4-(3-butyl-3-propyl)ureido-6-methoxy-7-methyl-3-oxoisobenzofuran-5-yl]-4-methyl-4-hexenoate;
2-(pyrrolidin-1-yl)ethyl (E)-6-[1,3-dihydro-4-(3-(2-chlorophenyl)ureido)-6-methoxy-7-methyl-3-oxoisobenzofuran-5-yl]-4-methyl-4-hexenoate;
2-(piperidin-1-yl)ethyl (E)-6-[1,3-dihydro-4-(3-(2-chlorophenyl)ureido)-6-methoxy-7-methyl-3-oxoisobenzofuran-5-yl]-4-methyl-4-hexenoate;
2-(thiazolidin-3-yl)ethyl (E)-6-[1,3-dihydro-4-(3-(2-chlorophenyl)ureido)-6-methoxy-7-methyl-3-oxoisobenzofuran-5-yl]-4-methyl-4-hexenoate;
3-(morpholin-4-yl)propyl (E)-6-[1,3-dihydro-4-(3-(2-chlorophenyl)ureido)-6-methoxy-7-methyl-3-oxoisobenzofuran-5-yl]-4-methyl-4-hexenoate;
4-(morpholin-4-yl)butyl (E)-6-[1,3-dihydro-4-(3-(2-chlorophenyl)ureido)-6-methoxy-7-methyl-3-oxoisobenzofuran-5-yl]-4-methyl-4-hexenoate;
2-(imidazolidin-1-yl)ethyl (E)-6-[1,3-dihydro-4-(3-(2-chlorophenyl)ureido)-6-methoxy-7-methyl-3-oxoisobenzofuran-5-yl]-4-methyl-4-hexenoate; and
2-(2-methyl-1,2-pyrazolidin-1-yl)ethyl (E)-6-[1,3-dihydro-4-(3-(2-chlorophenyl)ureido)-6-methoxy-7-methyl-3-oxoisobenzofuran-5-yl]-4-methyl-4-hexenoate.

EXAMPLE 14

Preparation of Compounds of Formula (I)

14A. Formula IC where $R^1$ is Hydrogen, $R^2$ is —C(O)$R^3$, where $R^3$ is —CF$_3$, and $R^7$ is Methyl To a solution of 0.5 g (1.5 mmol) of methyl (E)-6-(1,3-dihydro-4-amino-6-methoxy-7-methyl-3-oxoisobenzofuran-5-yl)-4-methyl-4-hexenoate in 5 ml of dichloromethane was added 0.5 ml (3.5 mmol) of trifluoroacetic anhydride. After 1 hour the reaction was partitioned between water and dichloromethane. The organic layer was washed twice with water, dried over magnesium sulfate, and concentrated to a solid. Recrystallization of this solid from hexane-ethyl acetate gave 0.520 g of methyl (E)-6-[1,3-dihydro-4-(trifluoroacetyl)amino-6-methoxy-7-methyl-3-oxoisobenzofuran-5-yl]-4-methyl-4-hexenoate as a white solid, mp 107°–109° C.

14B. Formula IC where $R^1$ is Hydrogen, $R^2$ is —C(O)$R^3$, where $R^3$ is Methyl, and $R^7$ is Methyl Similarly, following the procedures of Example 14A above, but replacing trifluoroacetic anhydride with acetyl chloride, the following compound was obtained:
methyl (E)-6-[1,3-dihydro-4-acetamido-6-methoxy-7-methyl-3-oxoisobenzofuran-5-yl]-4-methyl-4-hexenoate, mp 177°–179° C.

14C. Formula IC where $R^1$ is Hydrogen, $R^2$ is —C(O)$R^3$, where $R^3$ is Hydrogen, and $R^7$ is Methyl A solution of methyl (E)-6-(1,3-dihydro-4-amino-6-methoxy-7-methyl-3-oxoisobenzofuran-5-yl)-4-methyl-4-hexenoate (0.32 g, 1 mmol) in 3 ml formic acid was cooled to 0° C. and treated with 0.45 g of carbonyldiimidazole. After 1 hour water was added and the precipitate collected by filtration. This material was recrystallized from isopropanol to give 0.24 g of methyl (E)-6-[1,3-dihydro-4-formamido-6-methoxy-7-methyl-3-oxoisobenzofuran-5-yl]-4-methyl-4-hexenoate, as a white solid, mp 187°–189° C.

14D. Formula IC where $R^1$ is Hydrogen, $R^2$ is —C(O)$R^3$, and $R^7$ is Methyl, varying $R^3$ Similarly, following the procedures of Example 14A above, but replacing trifluoroacetic anhydride with other compounds of the formula ($R^3$C(O))$_2$O or of the formula $R^3$C(O)Cl, where $R^3$ is as defined in the Summary of the Invention, (which may be commercially obtained or prepared by methods known to those skilled in the art):
there are obtained the following compounds:
methyl (E)-6-[1,3-dihydro-4-(difluoroacetyl)amino-6-methoxy-7-methyl-3-oxoisobenzofuran-5-yl]-4-methyl-4-hexenoate;
methyl (E)-6-[1,3-dihydro-4-(fluoroacetyl)amino-6-methoxy-7-methyl-3-oxoisobenzofuran-5-yl]-4-methyl-4-hexenoate;
methyl (E)-6-[1,3-dihydro-4-(trichloroacetyl)amino-6-methoxy-7-methyl-3-oxoisobenzofuran-5-yl]-4-methyl-4-hexenoate and
methyl (E)-6-[1,3-dihydro-4-(fluorodichloroacetyl)amino-6-methoxy-7-methyl-3-oxoisobenzofuran-5-yl]-4-methyl-4-hexenoate.

EXAMPLE 15

Preparation of Compounds of Formula (I)

15A. Formula IC where $R^1$ is Hydrogen, $R^2$ is —C(O)$R^3$, where $R^3$ is —CF$_3$, and $R^7$ is Hydrogen Similarly, by following the procedure of Example 11A above, but substituting methyl (E)-6-[1,3-dihydro-4-(trifluoroacetyl)-amino-6-methoxy-7-methyl-3-oxoisobenzofuran-5-yl]-4-methyl-4-hexenoate and methyl (E)-6-[1,3-dihydro-4-acetamido-6-methoxy-7-methyl-3-oxoisobenzofuran-5-yl]-4-methyl-4-hexenoate for methyl (E)-6-[1,3-dihydro-4-(3,3-dimethylureido)-6-methoxy-7-methyl-3-oxoisobenzofuran-5-yl]-4-methyl-4-hexenoate, the following compounds were obtained:
(E)-6-[1,3-dihydro-4-(trifluoroacetyl)amino-6-methoxy-7-methyl-3-oxoisobenzofuran-5-yl]-4-methyl-4-hexenoic acid, mp 140°–141° C.; and
(E)-6-[1,3-dihydro-4-acetamido-6-methoxy-7-methyl-3-oxoisobenzofuran-5-yl]-4-methyl-4-hexenoic acid, mp 206°–210° C.

15B. Formula IC where $R^1$ is Hydrogen, $R^2$ is —C(O)$R^3$, and $R^7$ is Hydrogen, varying $R^3$ Similarly, following the procedure of Example 15A above, but replacing methyl (E)-6-[1,3-dihydro-4-(trifluoroacetyl)amino-6-methoxy-7-methyl-3-oxoisobenzofuran-5-yl]-4-methyl-4-hexenoate with:

methyl (E)-6-[1,3-dihydro-4-(difluoroacetyl)amino-6-methoxy-7-methyl-3-oxoisobenzofuran-5-yl]-4-methyl-4-hexenoate;

methyl (E)-6-[1,3-dihydro-4-(fluoroacetyl)amino-6-methoxy-7-methyl-3-oxoisobenzofuran-5-yl]-4-methyl-4-hexenoate;

methyl (E)-6-[1,3-dihydro-4-(trichloroacetyl)amino-6-methoxy-7-methyl-3-oxoisobenzofuran-5-yl]-4-methyl-4-hexenoate; and methyl (E)-6-[1,3-dihydro-4-(fluorodichloroacetyl)amino-6-methoxy-7-methyl-3-oxoisobenzofuran-5-yl]-4-methyl-4-hexenoate;

there are obtained the following compounds:

(E)-6-[1,3-dihydro-4-(difluoroacetyl)amino-6-methoxy-7-methyl-3-oxoisobenzofuran-5-yl]-4-methyl-4-hexenoic acid;

(E)-6-[1,3-dihydro-4-(fluoroacetyl)amino-6-methoxy-7-methoxy-3-oxoisobenzofuran-5-yl]- 4-methyl-4-hexenoic acid;

(E)-6-[1,3-dihydro-4-(trichloroacetyl)amino-6-methoxy-7-methyl-3-oxoisobenzofuran-5-yl]-4-methyl-4-hexenoic acid; and (E)-6-[1,3-dihydro-4-(fluorodichloroacetyl)amino-6-methoxy-7-methyl-3-oxoisobenzofuran-5-yl]-4-methyl-4-hexenoic acid.

EXAMPLE 16

Preparation of Compounds of Formula (I)

16A. Formula IC where $R^1$ is Hydrogen, $R^2$ is —C(O)$R^3$, where $R^3$ is —CF$_3$, and $R^7$ is Methyl Similarly, by following the procedure of Example 8A above, but replacing E-6-(1,3-dihydro-4-amino-6-methoxy-7-methyl-3-oxoisobenzofuran-5-yl)-4-methyl-4-hexenoic acid with:

methyl (E)-6-[1,3-dihydro-4-(trifluoroacetyl)amino-6-methoxy-7-methyl-3-oxoisobenzofuran-5-yl]-4-methyl-4-hexenoate;

methyl (E)-6-[1,3-dihydro-4-(difluoroacetyl)amino-6-methoxy-7-methyl-3-oxoisobenzofuran-5-yl]-4-methyl-4-hexenoate;

methyl (E)-6-[1,3-dihydro-4-(fluoroacetyl)amino-6-methoxy-7-methyl-3-oxoisobenzofuran-5-yl]-4-methyl-4-hexenoate;

methyl (E)-6-[1,3-dihydro-4-(trichloroacetyl)amino-6-methoxy-7-methyl-3-oxoisobenzofuran-5-yl]-4-methyl-4-hexenoate; and methyl (E)-6-[1,3-dihydro-4-(fluorodichloroacetyl)amino-6-methoxy-7-methyl-3-oxoisobenzofuran-5-yl]-4-methyl-4-hexenoate;

there are obtained the following respective compounds:

methyl E-6-[1,3-dihydro-4-(trifluoroacetyl)amino-6-methoxy-7-methyl-3-oxoisobenzofuran-5-yl]-4-methyl-4-hexenoate, methyl (E)-6-[1,3-dihydro-4-(difluoroacetyl)amino-6-methoxy-7-methyl-3-oxoisobenzofuran-5-yl]-4-methyl-4-hexenoate;

methyl (E)-6-[1,3-dihydro-4-(fluoroacetyl)amino-6-methoxy-7-methyl-3-oxoisobenzofuran-5-yl]-4-methyl-4-hexenoate;

methyl (E)-6-[1,3-dihydro-4-(trichloroacetyl)amino-6-methoxy-7-methyl-3-oxoisobenzofuran-5-yl]-4-methyl-4-hexenoate; and methyl (E)-6-[1,3-dihydro-4-(fluorodichloroacetyl)amino-6-methoxy-7-methyl-3-oxoisobenzofuran-5-yl]-4-methyl-4-hexenoate.

16B. Formula IC where $R^1$ is Hydrogen, $R^2$ is —C(O)$R^3$, varying $R^3$ and $R^7$ Similarly, following the procedure of Example 16A above, but replacing methanol with the following lower alkanols and optionally substituted phenols (other compounds of the formula $R^7$OH) (which may be commercially obtained or prepared by methods known to those skilled in the art):

ethanol, n-propanol, isopropanol, t-butanol, isoamyl alcohol, phenol, 2-chlorophenol, 2-trifluoromethylphenol, and 2-chloro-3,4-dimethoxyphenol;

there are obtained the following respective compounds:

ethyl (E)-6-[1,3-dihydro-4-(trifluoroacetyl)amino-6-methoxy-7-methyl-3-oxoisobenzofuran-5-yl]-4-methyl-4-hexenoate;

n-propyl (E)-6-[1,3-dihydro-4-(trifluoroacetyl)amino-6-methoxy-7-methyl-3-oxoisobenzofuran-5-yl]-4-methyl-4-hexenoate;

isopropyl (E)-6-[1,3-dihydro-4-(trifluoroacetyl)amino-6-methoxy-7-methyl-3-oxoisobenzofuran-5-yl]-4-methyl-4-hexenoate;

t-butyl (E)-6-[1,3-dihydro-4-(trifluoroacetyl)amino-6-methoxy-7-methyl-3-oxoisobenzofuran-5-yl]-4-methyl-4-hexenoate;

isoamyl (E)-6-[1,3-dihydro-4-(trifluoroacetyl)amino-6-methoxy-7-methyl-3-oxoisobenzofuran-5-yl]-4-methyl-4-hexenoate;

phenyl (E)-6-[1,3-dihydro-4-(trifluoroacetyl)amino-6-methoxy-7-methyl-3-oxoisobenzofuran-5-yl]-4-methyl-4-hexenoate;

2-chlorophenyl (E)-6-[1,3-dihydro-4-(trifluoroacetyl)amino-6-methoxy-7-methyl-3-oxoisobenzofuran-5-yl]-4-methyl-4-hexenoate;

2-trifluoromethylphenyl (E)-6-[1,3-dihydro-4-(trifluoroacetyl)amino-6-methoxy-7-methyl-3-oxoisobenzofuran-5-yl]-4-methyl-4-hexenoate;

2-chloro-3,4-dimethoxyphenyl (E)-6-[1,3-dihydro-4-(trifluoroacetyl)amino-6-methoxy-7-methyl-3-oxoisobenzofuran-5-yl]-4-methyl-4-hexenoate;

ethyl (E)-6-[1,3-dihydro-4-(difluoroacetyl)amino-6-methoxy-7-methyl-3-oxoisobenzofuran-5-yl]-4-methyl-4-hexenoate;

n-propyl (E)-6-[1,3-dihydro-4-(difluoroacetyl)amino-6-methoxy-7-methyl-3-oxoisobenzofuran-5-yl]-4-methyl-4-hexenoate;

isopropyl (E)-6-[1,3-dihydro-4-(difluoroacetyl)amino-6-methoxy-7-methyl-3-oxoisobenzofuran-5-yl]-4-methyl-4-hexenoate;

t-butyl (E)-6-[1,3-dihydro-4-(difluoroacetyl)amino-6-methoxy-7-methyl-3-oxoisobenzofuran-5-yl]-4-methyl-4-hexenoate;

isoamyl (E)-6-[1,3-dihydro-4-(difluoroacetyl)amino-6-methoxy-7-methyl-3-oxoisobenzofuran-5-yl]-4-methyl-4-hexenoate;

phenyl (E)-6-[1,3-dihydro-4-(difluoroacetyl)amino-6-methoxy-7-methyl-3-oxoisobenzofuran-5-yl]-4-methyl-4-hexenoate;

2-chlorophenyl (E)-6-[1,3-dihydro-4-(difluoroacetyl)amino-6-methoxy-7-methyl-3-oxoisobenzofuran-5-yl]-4-methyl-4-hexenoate;

2-trifluoromethylphenyl (E)-6-[1,3-dihydro-4-(difluoroacetyl)amino-6-methoxy-7-methyl-3-oxoisobenzofuran-5-yl]-4-methyl-4-hexenoate;

2-chloro-3,4-dimethoxyphenyl (E)-6-[1,3-dihydro-4-(difluoroacetyl)amino-6-methoxy-7-methyl-3-oxoisobenzofuran-5-yl]-4-methyl-4-hexenoate;

ethyl (E)-6-[1,3-dihydro-4-(fluoroacetyl)amino-6-methoxy-7-methyl-3-oxoisobenzofuran-5-yl]-4-methyl-4-hexenoate;

n-propyl (E)-6-[1,3-dihydro-4-(fluoroacetyl)amino-6-methoxy-7-methyl-3-oxoisobenzofuran-5-yl]-4-methyl-4-hexenoate;

isopropyl (E)-6-[1,3-dihydro-4-(fluoroacetyl)amino-6-methoxy-7-methyl-3-oxoisobenzofuran-5-yl]-4-methyl-4-hexenoate;

t-butyl (E)-6-[1,3-dihydro-4-(fluoroacetyl)amino-6-methoxy-7-methyl-3-oxoisobenzofuran-5-yl]-4-methyl-4-hexenoate;

isoamyl (E)-6-[1,3-dihydro-4-(fluoroacetyl)amino-6-methoxy-7-methyl-3-oxoisobenzofuran-5-yl]-4-methyl-4-hexenoate;

phenyl (E)-6-[1,3-dihydro-4-(fluoroacetyl)amino-6-methoxy-7-methyl-3-oxoisobenzofuran-5-yl]-4-methyl-4-hexenoate;

2-chlorophenyl (E)-6-[1,3-dihydro-4-(fluoroacetyl)amino-6-methoxy-7-methyl-3-oxoisobenzofuran-5-yl]-4-methyl-4-hexenoate;

2-trifluoromethylphenyl (E)-6-[1,3-dihydro-4-(fluoroacetyl)amino-6-methoxy-7-methyl-3-oxoisobenzofuran-5-yl]-4-methyl-4-hexenoate;

2-chloro-3,4-dimethoxyphenyl (E)-6-[1,3-dihydro-4-(fluoroacetyl)amino-6-methoxy-7-methyl-3-oxoisobenzofuran-5-yl]-4-methyl-4-hexenoate;

ethyl (E)-6-[1,3-dihydro-4-(trichloroacetyl)amino-6-methoxy-7-methyl-3-oxoisobenzofuran-5-yl]-4-methyl-4-hexenoate;

n-propyl (E)-6-[1,3-dihydro-4-(trichloroacetyl)amino-6-methoxy-7-methyl-3-oxoisobenzofuran-5-yl]-4-methyl-4-hexenoate;

isopropyl (E)-6-[1,3-dihydro-4-trichloroacetyl)amino-6-methoxy-7-methyl-3-oxoisobenzofuran-5-yl]-4-methyl-4-hexenoate;

t-butyl (E)-6-[1,3-dihydro-4-(trichloroacetyl)amino-6-methoxy-7-methyl-3-oxoisobenzofuran-5-yl]-4-methyl-4-hexenoate;

isoamyl (E)-6-[1,3-dihydro-4-(trichloroacetyl)amino-6-methoxy-7-methyl-3-oxoisobenzofuran-5-yl]-4-methyl-4-hexenoate;

phenyl (E)-6-[1,3-dihydro-4-(trichloroacetyl)amino-6-methoxy-7-methyl-3-oxoisobenzofuran-5-yl]-4-methyl-4-hexenoate;

2-chlorophenyl (E)-6-[1,3-dihydro-4-(trichloroacetyl)amino-6-methoxy-7-methyl-3-oxoisobenzofuran-5-yl]-4-methyl-4-hexenoate;

2-trifluoromethylphenyl (E)-6-[1,3-dihydro-4-(trichloroacetyl)amino-6-methoxy-7-methyl-3-oxoisobenzofuran-5-yl]-4-methyl-4-hexenoate;

2-chloro-3,4-dimethoxyphenyl (E)-6-[1,3-dihydro-4-(trichloroacetyl)amino-6-methoxy-7-methyl-3-oxoisobenzofuran-5-yl]-4-methyl-4-hexenoate;

ethyl (E)-6-[1,3-dihydro-4-(fluorodichloroacetyl)amino-6-methoxy-7-methyl-3-oxoisobenzofuran-5-yl]-4-methyl-4-hexenoate;

n-propyl (E)-6-[1,3-dihydro-4-(fluorodichloroacetyl)amino-6-methoxy-7-methyl-3-oxoisobenzofuran-5-yl]-4-methyl-4-hexenoate;

isopropyl (E)-6-[1,3-dihydro-4-(fluorodichloroacetyl)amino-6-methoxy-7-methyl-3-oxoisobenzofuran-5-yl]-4-methyl-4-hexenoate;

t-butyl (E)-6-[1,3-dihydro-4-(fluorodichloroacetyl)amino-6-methoxy-7-methyl-3-oxoisobenzofuran-5-yl]-4-methyl-4-hexenoate;

isoamyl (E)-6-[1,3-dihydro-4-(fluorodichloroacetyl)amino-6-methoxy-7-methyl-3-oxoisobenzofuran-5-yl]-4-methyl-4-hexenoate;

phenyl (E)-6-[1,3-dihydro-4-(fluorodichloroacetyl)amino-6-methoxy-7-methyl-3-oxoisobenzofuran-5-yl]-4-methyl-4-hexenoate;

2-chlorophenyl (E)-6-[1,3-dihydro-4-(fluorodichloroacetyl)amino-6-methoxy-7-methyl-3-oxoisobenzofuran-5-yl]-4-methyl-4-hexenoate;

2-trifluoromethylphenyl (E)-6-[1,3-dihydro-4-(fluorodichloroacetyl)amino-6-methoxy-7-methyl-3-oxoisobenzofuran-5-yl]-4-methyl-4-hexenoate; and 2-chloro-3,4-dimethoxyphenyl (E)-6-[1,3-dihydro-4-(fluorodichloroacetyl)amino-6-methoxy-7-methyl-3-oxoisobenzofuran-5-yl]-4-methyl-4-hexenoate.

EXAMPLE 17

Preparation of Compounds of Formula (I)

17A. Formula IC where $R^1$ is Hydrogen, $R^2$ is —C(O)$R^3$, where $R^3$ is —CF$_3$, and $R^7$ is Morpholinoethyl Similarly, by following the procedure of Example 9A above, but replacing E-6-(1,3-dihydro-4-amino-6-methoxy-7-methyl-3-oxoisobenzofuran-5-yl)-4-methyl-4-hexenoic acid with:

(E)-6-[1,3-dihydro-4-(trifluoroacetyl)amino-6-methoxy-7-methyl-3-oxoisobenzofuran-5-yl]-4-methyl-4-hexenoic acid;

(E)-6-[1,3-dihydro-4-(difluoroacetyl)amino-6-methoxy-7-methyl-3-oxoisobenzofuran-5-yl]-4-methyl-4-hexenoic acid;

(E)-6-[1,3-dihydro-4-(fluoroacetyl)amino-6-methoxy-7-methyl-3-oxoisobenzofuran-5-yl]-4-methyl-4-hexenoic acid;

(E)-6-[1,3-dihydro-4-(trichloroacetyl)amino-6-methoxy-7-methyl-3-oxoisobenzofuran-5-yl]-4-methyl-4-hexenoic acid; and (E)-6-[1,3-dihydro-4-(fluorodichloroacetyl)amino-6-methoxy-7-methyl-3-oxoisobenzofuran-5-yl]-4-methyl-4-hexenoic acid;

there are obtained the following respective compounds:

2-(morpholin-4-yl)ethyl (E)-6-[1,3-dihydro-4-(trifluoroacetyl)amino-6-methoxy-7-methyl-3-oxoisobenzofuran-5-yl]-4-methyl-4-hexenoate;

2-(morpholin-4-yl)ethyl (E)-6-[1,3-dihydro-4-(difluoroacetyl)amino-6-methoxy-7-methyl-3-oxoisobenzofuran-5-yl]-4-methyl-4-hexenoate;

2-(morpholin-4-yl)ethyl (E)-6-[1,3-dihydro-4-(fluoroacetyl)amino-6-methoxy-7-methyl-3-oxoisobenzofuran-5-yl]-4-methyl-4-hexenoate;

2-(morpholin-4-yl)ethyl (E)-6-[1,3-dihydro-4-(trichloroacetyl)amino-6-methoxy-7-methyl-3-oxoisobenzofuran-5-yl]-4-methyl-4-hexenoate; and 2-(morpholin-4-yl)ethyl (E)-6-[1,3-dihydro-4-(fluorodichloroacetyl)amino-6-methoxy-7-methyl-3-oxoisobenzofuran-5-yl]-4-methyl-4-hexenoate.

17B. Formula IC where $R^1$ is Hydrogen, $R^2$ is —C(O)$R^3$, varying $R^3$ and $R^7$ Similarly, following the procedure of Example 17A above, but replacing morpholinoethanol with the following heterocyclic aminoalkyl alcohols (compounds of the formula $R^7$OH) (which may be commercially obtained or prepared by methods known to those skilled in the art):

2-(pyrrolidin-1-yl)ethanol, 2-(piperidin-1-yl)ethanol, 2-(thiazolidin-3-yl)ethanol, 3-(morpholin-4-yl)propanol, 4-(morpholin-4-yl)butanol, 2-(imidazolidin-1-yl)ethanol, and 2-(2-methyl-1,2-pyrazolidin-1-yl)ethanol;
there are obtained the following respective compounds:

2-(pyrrolidin-1-yl)ethyl (E)-6-[1,3-dihydro-4-(trifluoroacetyl)amino-6-methoxy-7-methyl-3-oxoisobenzofuran-5-yl]-4-methyl-4-hexenoate;

2-(piperidin-1-yl)ethyl (E)-6-[1,3-dihydro-4-(trifluoroacetyl)amino-6-methoxy-7-methyl-3-oxoisobenzofuran-5-yl]-4-methyl-4-hexenoate;

2-(thiazolidin-3-yl)ethyl (E)-6-[1,3-dihydro-4-(trifluoroacetyl)amino-6-methoxy-7-methyl-3-oxoisobenzofuran-5-yl]-4-methyl-4-hexenoate;

3-(morpholin-4-yl)propyl (E)-6-[1,3-dihydro-4-(trifluoroacetyl)amino-6-methoxy-7-methyl-3-oxoisobenzofuran-5-yl]-4methyl-4-hexenoate;

4-(morpholin-4-yl)butyl (E)-6-[1,3-dihydro-4-(trifluoroacetyl)amino-6-methoxy-7-methyl-3-oxoisobenzofuran-5-yl]-4-methyl-4-hexenoate;

2-(imidazolidin-1-yl)ethyl (E)-6-[1,3-dihydro-4-(trifluoroacetyl)amino-6-methoxy-7-methyl-3-oxoisobenzofuran-5-yl]-4-methyl-4-hexenoate;

2-(2-methyl-1,2-pyrazolidin-1-yl)ethyl (E)-6-[1,3-dihydro-4-(trifluoroacetyl)amino-6-methoxy-7-methyl-3-oxoisobenzofuran-5-yl]-4-methyl-4-hexenoate;

2-(pyrrolidin-1-yl)ethyl (E)-6-[1,3-dihydro-4-(difluoroacetyl)amino-6-methoxy-7-methyl-3-oxoisobenzofuran-5-yl]-4-methyl-4-hexenoate;

2-(piperidin-1-yl)ethyl (E)-6-[1,3-dihydro-4-(difluoroacetyl)amino-6-methoxy-7-methyl-3-oxoisobenzofuran-5-yl]-4-methyl-4-hexenoate;

2-(thiazolidin-3-yl)ethyl (E)-6-[1,3-dihydro-4-(difluoroacetyl)amino-6-methoxy-7-methyl-3-oxoisobenzofuran-5-yl]-4-methyl-4-hexenoate;

3-(morpholin-4-yl)propyl (E)-6-[1,3-dihydro-4-(difluoroacetyl)amino-6-methoxy-7-methyl-3-oxoisobenzofuran-5-yl]-4-methyl-4-hexenoate;

4-(morpholin-4-yl)butyl (E)-6-[1,3-dihydro-4-(difluoroacetyl)amino-6-methoxy-7-methyl-3-oxoisobenzofuran-5-yl]-4-methyl-4-hexenoate;

2-(imidazolidin-1-yl)ethyl (E)-6-[1,3-dihydro-4-(difluoroacetyl)amino-6-methoxy-7-methyl-3-oxoisobenzofuran-5-yl]-4-methyl-4-hexenoate;

2-(2-methyl-1,2-pyrazolidin-1-yl)ethyl (E)-6-[1,3-dihydro-4-(difluoroacetyl)amino-6-methoxy-7-methyl-3-oxoisobenzofuran-5-yl]-4-methyl-4-hexenoate;

2-(pyrrolidin-1-yl)ethyl (E)-6-[1,3-dihydro-4-(fluoroacetyl)amino-6-methoxy-7-methyl-3-oxoisobenzofuran-5-yl]-4-methyl-4-hexenoate;

2-(piperidin-1-yl)ethyl (E)-6-[1,3-dihydro-4-(fluoroacetyl)amino-6-methoxy-7-methyl-3-oxoisobenzofuran-5-yl]-4-methyl-4-hexenoate;

2-(thiazolidin-3-yl)ethyl (E)-6-[1,3-dihydro-4-(fluoroacetyl)amino-6-methoxy-7-methyl-3-oxoisobenzofuran-5-yl]-4-methyl-4-hexenoate;

3-(morpholin-4-yl)propyl (E)-6-[1,3-dihydro-4-(fluoroacetyl)amino-6-methoxy-7-methyl-3-oxoisobenzofuran-5-yl]-4-methyl-4-hexenoate;

4-(morpholin-4-yl)butyl (E)-6-[1,3-dihydro-4-(fluoroacetyl)amino-6-methoxy-7-methyl-3-oxoisobenzofuran-5-yl]-4-methyl-4-hexenoate;

2-(imidazolidin-1-yl)ethyl (E)-6-[1,3-dihydro-4-(fluoroacetyl)amino-6-methoxy-7-methyl-3-oxoisobenzofuran-5-yl]-4-methyl-4-hexenoate;

2-(2-methyl-1,2-pyrazolidin-1-yl)ethyl (E)-6-[1,3-dihydro-4-(fluoroacetyl)amino-6-methoxy-7-methyl-3-oxoisobenzofuran-5-yl]-4-methyl-4-hexenoate;

2-(pyrrolidin-1-yl)ethyl (E)-6-[1,3-dihydro-4-(trichloroacetyl)amino-6-methoxy-7-methyl-3-oxoisobenzofuran-5-yl]4-methyl-4-hexenoate;

2-(piperidin-1-yl)ethyl (E)-6-[1,3-dihydro-4-(trichloroacetyl)amino-6-methoxy-7-methyl-3-oxoisobenzofuran-5-yl]-4-methyl-4-hexenoate;

2-(thiazolidin-3-yl)ethyl (E)-6-[1,3-dihydro-4-(trichloroacetyl)amino-6-methoxy-7-methyl-3-oxoisobenzofuran-5-yl]-4-methyl-4-hexenoate;

3-(morpholin-4-yl)propyl (E)-6-[1,3-dihydro-4-(trichloroacetyl)amino-6-methoxy-7-methyl-3-oxoisobenzofuran-5-yl]-4-methyl-4-hexenoate;

4-(morpholin-4-yl)butyl (E)-6-[1,3-dihydro-4-(trichloroacetyl)amino-6-methoxy-7-methyl-3-oxoisobenzofuran-5-yl]-4-methyl-4-hexenoate;

2-(imidazolidin-1-yl)ethyl (E)-6-[1,3-dihydro-4-(trichloroacetyl)amino-6-methoxy-7-methyl-3-oxoisobenzofuran-5-yl]-4-methyl-4-hexenoate;

2-(2-methyl-1,2-pyrazolidin-1-yl)ethyl (E)-6-[1,3-dihydro-4-(trichloroacetyl)amino-6-methoxy-7-methyl-3-oxoisobenzofuran-5-yl]-4-methyl-4-hexenoate;

2-(pyrrolidin-1-yl)ethyl (E)-6-[1,3-dihydro-4-(fluorodichloroacetyl)amino-6-methoxy-7-methyl-3-oxoisobenzofuran-5-yl]-4-methyl-4-hexenoate;

2-(piperidin-1-yl)ethyl (E)-6-[1,3-dihydro-4-(fluorodichloroacetyl)amino-6-methoxy-7-methyl-3-oxoisobenzofuran-5-yl]-4-methyl-4-hexenoate;

2-(thiazolidin-3-yl)ethyl (E)-6-[1,3-dihydro-4-(fluorodichloroacetyl)amino-6-methoxy-7-methyl-3-oxoisobenzofuran-5-yl]-4-methyl-4-hexenoate;

3-(morpholin-4-yl)propyl (E)-6-[1,3-dihydro-4-(fluorodichloroacetyl)amino-6-methoxy-7-methyl-3-oxoisobenzofuran-5-yl]-4-methyl-4-hexenoate;

4-(morpholin-4-yl)butyl (E)-6-[1,3-dihydro-4-(fluorodichloroacetyl)amino-6-methoxy-7-methyl-3-oxoisobenzofuran-5-yl]-4-methyl-4-hexenoate;

2-(imidazolidin-1-yl)ethyl (E)-6-[1,3-dihydro-4-(fluorodichloroacetyl)amino-6-methoxy-7-methyl-3-oxoisobenzofuran-5-yl]-4-methyl-4-hexenoate; and 2-(2-methyl-1,2-pyrazolidin-1-yl)ethyl (E)-6-[1,3-dihydro-4-(fluorodichloroacetyl)amino-6-methoxy-7-methyl-3-oxoisobenzofuran-5-yl]-4-methyl-4-hexenoate.

EXAMPLE 18

Preparation of Compounds of Formula (I)

18A. Formula ID wherein $R^1$ is Methyl, $R^2$ is —C(O)$R^3$, where $R^3$ is —CF3, and $R^7$ is Methyl To a solution of 0.35 g (0.82 mmol) of methyl (E)-6-[1,3-dihydro-4-(trifluoroacetyl)amino-6-methoxy-7-methyl-3-oxoisobenzofuran-5-yl]-4-methyl-4-hexenoate in 4 ml of dimethylformamide was added 0.47 g (3.40 mmol) of potassium carbonate and 0.23 ml (3.69 mmol) of iodomethane. The mixture was stirred for 24 hours and then partitioned between ethyl acetate and water. The organic layer was washed with water, dried over magnesium sulfate, and concentrated under reduced pressure to give methyl (E)-6-[1,3-dihydro-4-(N-(trifluoroacetyl)-N-methyl)amino-6-methoxy-7-methyl-3-oxoisobenzofuran-5-yl]-4-methyl-4-hexenoate, an oil, NMR: δ5.22–5.17 (multiplet ("m"), 2H); 5.10–5.04

(broad triplet, 1H); 3.81 (singlet ("s"), 3H); 3.62 (s, 3H); 3.42–3.27 (m, 5H); 2.45–2.25 (m, 5H); 1.75 (s, 3H).

18B. Formula I wherein $R^1$ is Lower Alkyl, $R^2$ is —C(O)$R^3$, where $R^3$ is —CF3, and $R^7$ is Methyl Similarly, following the procedures of Example 18A above, but replacing iodomethane with the following compounds of the formula $R^1$Br or $R^1$I where $R^1$ is lower alkyl (which may be commercially obtained or prepared by methods known to those skilled in the art):

iodoethane or bromoethane, and iodoisopropane or bromoisopropane;

there are obtained the following respective compounds:

methyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; and methyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate.

EXAMPLE 19

Preparation of Compounds of Formula (I)

19A. Formula ID wherein $R^1$ is Methyl, $R^2$ is —C(O)$R^3$, where $R^3$ is —CF3, and $R^7$ is Hydrogen Methyl (E)-6-[1,3-dihydro-4-(trifluoroacetylmethyl)amino-6-methoxy-7-methyl-3-oxoisobenzofuran-5-yl]-4-methyl-4-hexenoate, the amount of oil yielded in Example 18A above, was suspended in 8.2 ml of 4:1 methanol:water and 0.138 g (3.28 mmol) of lithium hydroxide monohydrate was added. The mixture was heated at 50°–60° C. for 4 hours. Upon cooling the reaction was partitioned between aqueous sodium hydrogen sulfate and ethyl acetate. Th organic layer was washed with brine, dried over magnesium sulfate, and concentrated to give (E)-6-[1,3-dihydro-4-(N-(trifluoroacetyl)-N-methyl)amino-6-methoxy-7-methyl-3-oxoisobenzofuran-5-yl]-4-methyl-4-hexenoic acid, mp 159°–160° C.

19B. Formula ID wherein $R^1$ is Lower Alkyl, $R^2$ is —C(O)$R^3$, where $R^3$ is —CF3, and $R^7$ is Hydrogen Similarly, following the procedures of Example 19A above, but replacing methyl (E)-6-[1,3-dihydro-4-(trifluoroacetylmethyl)amino-6-methoxy-7-methyl-3-oxoisobenzofuran-5-yl]-4-methyl-4-hexenoate with:

methyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; and methyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate;

there are obtained the following respective compounds:

(E)-6-[1,3-dihydro-4-(N-(trifluoroacetyl)-N-ethyl)amino-6-methoxy-7-methyl-3-oxoisobenzofuran-5-yl]-4-methyl-4-hexenoic acid; and (E)-6-[1,3-dihydro-4-(N-(trifluoroacetyl)-N-isopropyl)amino-6-methoxy-7-methyl-3-oxoisobenzofuran-5-yl]-4-methyl-4-hexenoic acid.

19C. Formula ID wherein $R^1$ is Lower Alkyl, $R^2$ is —C(O)$R^3$, where $R^3$ is —CF3, and $R^7$ is Methyl Similarly, by following the procedure of Example 8A above, but replacing E-6-(1,3-dihydro-4-amino-6-methoxy-7-methyl-3-oxoisobenzofuran-5-yl)-4-methyl-4-hexenoic acid with:

(E)-6-[1,3-dihydro-4-(N-(trifluoroacetyl)-N-methyl)amino-6-methoxy-7-methyl-3-oxoisobenzofuran-5-yl]-4-methyl-4-hexenoic acid;

(E)-6-[1,3-dihydro-4-(N-(trifluoroacetyl)-N-ethyl)amino-6-methoxy-7-methyl-3-oxoisobenzofuran-5-yl]-4-methyl-4-hexenoic acid; and (E)-6-[1,3-dihydro-4-(N-(trifluoroacetyl)-N-isopropyl)amino-6-methoxy-7-methyl-3-oxoisobenzofuran-5-yl]-4-methyl-4-hexenoic acid;

there are obtained the following compounds:

methyl (E)-6-[1,3-dihydro-4-(N-(trifluoroacetyl)-N-methyl)amino-6-methoxy-7-methyl-3-oxoisobenzofuran-5-yl]-4-methyl-4-hexenoate;

methyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; and methyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate.

19D. Formula ID wherein $R^1$ is Lower Alkyl, $R^2$ is —C(O)$R^3$, where $R^3$ is —CF3, and $R^7$ is varied Similarly, following the procedure of Example 19C above, but replacing methanol with the following lower alkanols and optionally substituted phenols (other compounds of the formula $R^7$OH) (which may be commercially obtained or prepared by methods known to those skilled in the art):

ethanol, n-propanol, isopropanol, t-butanol, isoamyl alcohol, phenol, 2-chlorophenol, 2-trifluoromethylphenol, and 2-chloro-3,4-dimethoxyphenol;

there are obtained the following respective compounds:

ethyl (E)-6-[1,3-dihydro-4-(N-(trifluoroacetyl)-N-methyl)amino-6-methoxy-7-methyl-3-oxoisobenzofuran-5-yl]-4-methyl-4-hexenoate;

n-propyl (E)-6-[1,3-dihydro-4-(N-(trifluoroacetyl)-N-methyl)amino-6-methoxy-7-methyl-3-oxoisobenzofuran-5-yl]-4-methyl-4-hexenoate;

isopropyl (E)-6-[1,3-dihydro-4-(N-(trifluoroacetyl)-N-methyl)amino-6-methoxy-7-methyl-3-oxoisobenzofuran-5-yl]-4-methyl-4-hexenoate;

t-butyl (E)-6-[1,3-dihydro-4-(N-(trifluoroacetyl)-N-methyl)amino-6-methoxy-7-methyl-3-oxoisobenzofuran-5-yl]-4-methyl-4-hexenoate;

isoamyl (E)-6-[1,3-dihydro-4-(N-(trifluoroacetyl)-N-methyl)amino-6-methoxy-7-methyl-3-oxoisobenzofuran-5-yl]-4-methyl-4-hexenoate;

phenyl (E)-6-[1,3-dihydro-4-(N-(trifluoroacetyl)-N-methyl)amino-6-methoxy-7-methyl-3-oxoisobenzofuran-5-yl[-4-methyl-4-hexenoate;

2-chlorophenyl (E)-6-[1,3-dihydro-4-(N-(trifluoroacetyl)-N-methyl)amino-6-methoxy-7-methyl-3-oxoisobenzofuran-5-yl]-4-methyl-4-hexenoate;

2-trifluoromethylphenyl (E)-6-[1,3-dihydro-4-(N-(trifluoroacetyl)-N-methyl)amino-6-methoxy-7-methyl-3-oxoisobenzofuran-5-yl]-4-methyl-4-hexenoate;

2-chloro-3,4-dimethoxyphenyl (E)-6-[1,3-dihydro-4-(N-(trifluoroacetyl)-N-methyl)amino-6-methoxy-7-methyl-3-oxoisobenzofuran-5-yl[-4-methyl-4-hexenoate;

ethyl (E)-6-[1,3-dihydro-4-(N-(trifluoroacetyl)-N-ethyl)amino-6-methoxy-7-methyl-3-oxoisobenzofuran-5-yl[-4-methyl-4-hexenoate;

n-propyl (E)-6-[1,3-dihydro-4-(N-(trifluoroacetyl)-N-ethyl)amino-6-methoxy-7-methyl-3-oxoisobenzofuran-5-yl[-4-methyl-4-hexenoate;

isopropyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate;

t-butyl (E)-6-[1,3-dihydro-4-(N-(trifluoroacetyl)-N-ethyl)amino-6-methoxy-7-methyl-3-oxoisobenzofuran-5-yl[-4-methyl-4-hexenoate;

isoamyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate;

phenyl (E)-6-[1,3-dihydro-4-(N-(trifluoracetyl)-N-ethyl)amino-6-methoxy-7-methyl-3-oxoisobenzofuran-5-yl[-4-methyl-4-hexenoate;

2-chlorophenyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate;

2-trifluoromethylphenyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate;

2-chloro-3,4-dimethoxyphenyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate;

ethyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate;

n-propyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate;

isopropyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate;

t-butyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate;

isoamyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate;

phenyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate;

2-chlorophenyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate;

2-trifluoromethylphenyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; and 2-chloro-3,4-dimethoxyphenyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate.

19E. Formula ID wherein $R^1$ is Lower Alkyl, $R^2$ is —C(O)$R^3$, where $R^3$ is —CF3, and $R^7$ is morpholinoethyl Similarly, by following the procedure of Example 9A above, but replacing E-6-(1,3-dihydro-4-amino-6-methoxy-7-methyl-3-oxoisobenzofuran-5-yl)-4-methyl-4-hexenoic acid with:

(E)-6-[1,3-dihydro-4-(N-(trifluoroacetyl)-N-methyl-)amino-6-methoxy-7-methyl-3-oxoisobenzofuran-5-yl]-4-methyl-4-hexenoic acid;

(E)-6-[1,3-dihydro-4-(N-(trifluoracetyl)-N-ethyl-)amino-6-methoxy-7-methyl-3-oxoisobenzofuran-5-yl]-4-methyl-4-hexenoic acid; and (E)-6-[1,3-dihydro-4-(N-(trifluoroacetyl)-N-isopropyl)amino-6-methoxy-7-methyl-3-oxoisobenzofuran-5-yl]-4-methyl-4-hexenoic acid; there are obtained the following compounds:

2-(morpholin-4-yl)ethyl (E)-6-[1,3-dihydro-4-(N-(trifluracetyl)-N-methyl)amino-6-methoxy-7-methyl-3-oxoisobenzofuran-5-yl]-4-methyl-4-hexenoate;

2-(morpholin-4-yl)ethyl (E)-6-[1,3-dihydro-4-(N-(trifluoracetyl)-N-ethyl)amino-6-methoxy-7-methyl-3-oxoisobenzofuran-5-yl]-4-methyl-4-hexenoate; and 2-(morpholin-4-yl)ethyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate.

19F. Formula ID wherein $R^1$ is Lower Alkyl, $R^2$ is —C(O)$R^3$, where $R^3$ is —CF3, and $R^7$ is varied Similarly, following the procedure of Example 19FE above, but replacing morpholinoethanol with the following heterocyclic aminoalkyl alcohols (other compounds of the formula $R^7OH$) (which may be commercially obtained or prepared by methods known to those skilled in the art):

2-(pyrrolidin-1-yl)ethanol; 2-(piperidin-1-yl)ethanol; 2-(thiazolidin-3-yl)ethanol; 3-(morpholin-4-yl)propanol; 4-(morpholin-4-yl)butanol; 2-(imidazolidin-1-yl)ethanol; and 2-(2-methyl-1,2-pyrazolidin-1-yl)ethanol;

there are obtained the following respective compounds:

2-(pyrrolidin-1-yl)ethyl (E)-6-[1,3-dihydro-4-(N-(trifluoracetyl)-N-methyl)amino-6-methoxy-7-methyl-3-oxoisobenzofuran-5-yl]-4-methyl-4-hexenoate;

2-(piperidin-1-yl)ethyl (E)-6-[1,3-dihydro-4-(N-(trifluoracetyl)-N-methyl)amino-6-methoxy-7-methyl-3-oxoisobenzofuran-5-yl]-4-methyl-4-hexenoate;

2-(thiazolidin-3-yl)ethyl (E)-6-[1,3-dihydro-4-(N-(trifluoracetyl)-N-methyl)amino-6-methoxy-7-methyl-3-oxoisobenzofuran-5-yl]-4-methyl-4-hexenoate;

3-(morpholin-4-yl)propyl (E)-6-[1,3-dihydro-4-(N-(trifluoracetyl)-N-methyl)amino-6-methoxy-7-methyl-3-oxoisobenzofuran-5-yl]-4-methyl-4-hexenoate;

4-(morpholin-4-yl)butyl (E)-6-[1,3-dihydro-4-(N-(trifluoracetyl)-N-methyl)amino-6-methoxy-7-methyl-3-oxoisobenzofuran-5-yl]-4-methyl-4-hexenoate;

2-(imidazolidin-1-yl)ethyl (E)-6-[1,3-dihydro-4-(N-(trifluoroacetyl)-N-methyl)amino-6-methoxy-7-methyl-3-oxoisobenzofuran-5-yl]-4-methyl-4-hexenoate;

2-(2-methyl-1,2-pyrazolidin-1-yl)ethyl (E)-6-[1,3-dihydro-4-(N-(trifluoroacetyl)-N-methyl)amino-6-methoxy-7-methyl-3-oxoisobenzofuran-5-yl]-4-methyl-4-hexenoate;

2-(pyrrolidin-1-yl)ethyl (E)-6-[1,3-dihydro-4-(N-(trifluoracetyl)-N-ethyl)amino-6-methoxy-7-methyl-3-oxoisobenzofuran-5-yl]-4-methyl-4-hexenoate;

2-(piperidin-1-yl)ethyl (E)-6-[1,3-dihydro-4-(N-(trifluoracetyl)-N-ethyl)amino-6-methoxy-7-methyl-3-oxoisobenzofuran-5-yl]-4-methyl-4-hexenoate;

2-(thiazolidin-3-yl)ethyl (E)-6-[1,3-dihydro-4-(N-(trifluoracetyl)-N-ethyl)amino-6-methoxy7-methyl-3-oxoisobenzofuran-5-yl)]-4-methyl-4-hexenoate;

3-(morpholin-4-yl)propyl (E)-6-[1,3-dihydro-4-(N-(trifluoracetyl)-N-ethyl)amino-6-methoxy-7-methyl-3-oxoisobenzofuran-5-yl]-4-methyl-4-hexenoate;

4-(morpholin-4-yl)butyl (E)-6-[1,3-dihydro-4-(N-(trifluoracetyl)-N-ethyl)amino-6-methoxy-7-methyl-3-oxoisobenzofuran-5-yl]-4-methyl-4-hexenoate;

2-(imidazolidin-1-yl)ethyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate;

2-(2-methyl-1,2-pyrazolidin-1-yl)ethyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate;

2-(pyrrolidin-1-yl)ethyl (E)-6-[1,3-dihydro-4-(N-(trifluoracetyl)-N-isopropyl)amino-6-methoxy-7- methyl-3-oxoisobenzofuran-5-yl]-4-methyl-4-hexenoate;

2-(piperidin-1-yl)ethyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate;

2-(thiazolidin-3-yl)ethyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate;

3-(morpholin-4-yl)propyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate;

4-(morpholin-4-yl)butyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate;

2-(imidazolidin-1-yl)ethyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; and 2-(2-methyl-1,2-pyrazolidin-1-yl)ethyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate.

EXAMPLE 20

Preparation of Compounds of Formula (I)

20A. Formula IE wherein $R^1$ is Methyl, and $R^2$ and $R^7$ are Hydrogen

Similarly, by following the procedure of Example 11A above, but substituting (E)-6-[1,3-dihydro-4-(N-(trifluoroacetyl)-N-methyl)amino-6-methoxy-7-methyl-3-oxoisobenzofuran-5-yl]-4-methyl-4-hexenoic acid for methyl (E)-6-[1,3-dihydro-4-(3,3-dimethylureido)-6-methoxy-7-methyl-3-oxoisobenzofuran-5-yl]-4-methyl-4-hexenoate gave (E)-6-(1,3-dihydro-4-methylamino-6-methoxy-7-methyl-3-oxoisobenzofuran-5-yl)-4-methyl-4-hexenoic acid, mp 121°–124° C.

20B. Formula IE where $R^1$ is Lower Alkyl, and $R^2$ and $R^7$ are Hydrogen

Similarly, following the procedure of Example 20A above, but replacing (E)-6-[1,3-dihydro-4-(N-(trifluoroacetyl)-N-methyl)amino-6-methoxy-7-methyl-3-oxoisobenzofuran-5-yl]-4-methyl-4-hexenoic acid with:

(E)-6-[1,3-dihydro-4-(N-(trifluoroacetyl)-N-ethyl)amino-6-methoxy-7-methyl-3-oxoisobenzofuran-5-yl]-4-methyl-4-hexenoic acid; and (E)-6-[1,3-dihydro-4-(N-(trifluoroacetyl)-N-isopropyl)amino-6-methoxy-7-methyl-3-oxoisobenzofuran-5-yl]-4-methyl-4-hexenoic acid; there are obtained the following respective compounds:

(E)-6-(1,3-dihydro-4-ethylamino-6-methoxy-7-methyl-3-oxoisobenzofuran-5-yl)-4-methyl-4-hexenoic acid; and (E)-6-(1,3-dihydro-4-isopropylamino-6-methoxy-7-methyl-3-oxoisobenzofuran-5-yl)-4-methyl-4-hexenoic acid.

EXAMPLE 21

Preparation of Compounds of Formula (I)

21A. Formula IE wherein $R^1$ is Lower Alkyl, $R^2$ is Hydrogen and $R^7$ is Methyl Similarly, by following the procedure of Example 8A above, but replacing E-6-(1,3-dihydro-4-amino-6-methoxy-7-methyl-3-oxoisobenzofuran-5-yl)-4-methyl-4-hexenoic acid with:

(E)-6-(1,3-dihydro-4-methylamino-6-methoxy-7-methyl-3-oxoisobenzofuran-5-yl)-4-methyl-4-hexenoic acid;

(E)-6-(1,3-dihydro-4-ethylamino-6-methoxy-7-methyl-3-oxoisobenzofuran-5-yl)-4-methyl-4-hexenoic acid and (E)-6-(1,3-dihydro-4-isopropylamino-6-methoxy-7-methyl-3-oxoisobenzofuran-5-yl)-4-methyl-4-hexenoic acid;

there are obtained the following respective compounds:

methyl E-6-(1,3-dihydro-4-methylamino-6-methoxy-7-methyl-3-oxoisobenzofuran-5-yl)-4-methyl-4-hexenoate;

methyl (E)-6-(1,3-dihydro-4-ethylamino-6-methoxy-7-methyl-3-oxoisobenzofuran-5-yl)-4-methyl-4-hexenoic acid; and methyl (E)-6-(1,3-dihydro-4-isopropylamino-6-methoxy-7-methyl-3-oxoisobenzofuran-5-yl)-4-methyl-4-hexenoic acid.

21B. Formula IE where $R^2$ is Hydrogen, varying $R^1$ and $R^7$

Similarly, following the procedure of Example 21A, above, but replacing methanol with the following lower alkanols and optionally substituted phenols (other compounds of the formula $R^7OH$) (which may be commercially obtained or prepared by methods known to those skilled in the art):

ethanol, n-propanol, isopropanol, t-butanol, isoamyl alcohol, phenol, 2-chlorophenol, 2-trifluoromethylphenol, and 2-chloro-3,4-dimethoxyphenol;

there are obtained the following respective compounds:

ethyl (E)-6-(1,3-dihydro-4-methylamino-6-methoxy-7-methyl-3-oxoisobenzofuran-5-yl)-4-methyl-4-hexenoate;

n-propyl (E)-6-(1,3-dihydro-4-methylamino-6-methoxy-7-methyl-3-oxoisobenzofuran-5-yl)-4-methyl-4-hexenoate;

isopropyl (E)-6-(1,3-dihydro-4-methylamino-6-methoxy-7-methyl-3-oxoisobenzofuran-5-yl)-4-methyl-4-hexenoate;

t-butyl (E)-6-(1,3-dihydro-4-methylamino-6-methoxy-7-methyl-3-oxoisobenzofuran-5-yl)-4-methyl-4-hexenoate;

isoamyl (E)-6-(1,3-dihydro-4-methylamino-6-methoxy-7-methyl-3-oxoisobenzofuran-5-yl)-4-methyl-4-hexenoate;

phenyl (E)-6-(1,3-dihydro-4-methylamino-6-methoxy-7-methyl-3-oxoisobenzofuran-5-yl)-4-methyl-4-hexenoate;

2-chlorophenyl (E)-6-(1,3-dihydro-4-methylamino-6-methoxy-7-methyl-3-oxoisobenzofuran-5-yl)-4-methyl-4-hexenoate;

2-trifluoromethylphenyl (E)-6-(1,3-dihydro-4-methylamino-6-methoxy-7-methyl-3-oxoisobenzofuran-5-yl)-4-methyl-4-hexenoate;

2-chloro-3,4-dimethoxyphenyl (E)-6-(1,3-dihydro-4-methylamino-6-methoxy-7-methyl-3-oxoisobenzofuran-5-yl)-4-methyl-4-hexenoate;

ethyl (E)-6-(1,3-dihydro-4-ethylamino-6-methoxy-7-methyl-3-oxoisobenzofuran-5-yl)-4-methyl-4-hexenoate;

n-propyl (E)-6-(1,3-dihydro-4-ethylamino-6-methoxy-7-methyl-3-oxoisobenzofuran-5-yl)-4-methyl-4-hexenoate;

isopropyl (E)-6-(1,3-dihydro-4-ethylamino-6-methoxy-7-methyl-3-oxoisobenzofuran-5-yl)-4-methyl-4-hexenoate;
t-butyl (E)-6-(1,3-dihydro-4-ethylamino-6-methoxy-7-methyl-3-oxoisobenzofuran-5-yl)-4-methyl-4-hexenoate;
isoamyl (E)-6-(1,3-dihydro-4-ethylamino-6-methoxy-7-methyl-3-oxoisobenzofuran-5-yl)-4-methyl-4-hexenoate;
phenyl (E)-6-(1,3-dihydro-4-ethylamino-6-methoxy-7-methyl-3-oxoisobenzofuran-5-yl)-4-methyl-4-hexenoate;
2-chlorophenyl (E)-6-(1,3-dihydro-4-ethylamino-6-methoxy-7-methyl-3-oxoisobenzofuran-5-yl)-4-methyl-4-hexenoate;
2-trifluoromethylphenyl (E)-6-(1,3-dihydro-4-ethylamino-6-methoxy-7-methyl-3-oxoisobenzofuran-5-yl)-4-methyl-4-hexenoate;
2-chloro-3,4-dimethoxyphenyl (E)-6-(1,3-dihydro-4-ethylamino-6-methoxy-7-methyl-3-oxoisobenzofuran-5-yl)-4-methyl-4-hexenoate;
ethyl (E)-6-(1,3-dihydro-4-isopropylamino-6-methoxy-7-methyl-3-oxoisobenzofuran-5-yl)-4-methyl-4-hexenoate;
n-propyl (E)-6-(1,3-dihydro-4-isopropylamino-6-methoxy-7-methyl-3-oxoisobenzofuran-5-yl)-4-methyl-4-hexenoate;
isopropyl (E)-6-(1,3-dihydro-4-isopropylamino-6-methoxy-7-methyl-3-oxoisobenzofuran-5-yl)-4-methyl-4-hexenoate;
t-butyl (E)-6-(1,3-dihydro-4-isopropylamino-6-methoxy-7-methyl-3-oxoisobenzofuran-5-yl)-4-methyl-4-hexenoate;
isoamyl (E)-6-(1,3-dihydro-4-isopropylamino-6-methoxy-7-methyl-3-oxoisobenzofuran-5-yl)-4-methyl-4-hexenoate;
phenyl (E)-6-(1,3-dihydro-4-isopropylamino-6-methoxy-7-methyl-3-oxoisobenzofuran-5-yl)-4-methyl-4-hexenoate;
2-chlorophenyl (E)-6-(1,3-dihydro-4-isopropylamino-6-methoxy-7-methyl-3-oxoisobenzofuran-5-yl)-4-methyl-4-hexenoate;
2-trifluoromethylphenyl (E)-6-(1,3-dihydro-4-isopropylamino-6-methoxy-7-methyl-3-oxoisobenzofuran-5-yl)-4-methyl-4-hexenoate and
2-chloro-3,4-dimethoxyphenyl (E)-6-(1,3-dihydro-4-isopropylamino-6-methoxy-7-methyl-3-oxoisobenzofuran-5-yl)-4-methyl-4-hexenoate.

EXAMPLE 22

Preparation of Compounds of Formula (I)

22A. Formula IE wherein $R^1$ is Lower Alkyl, $R^2$ is hydrogen, and $R^7$ is Morpholinoethyl Similarly, by following the procedure of Example 9A, above, but replacing E-6-(1,3-dihydro-4-amino-6-methoxy-7-methyl-3-oxoisobenzofuran-5-yl)-4-methyl-4-hexenoic acid with:
(E)-6-(1,3-dihydro-4-methylamino-6-methoxy-7-methyl-3-oxoisobenzofuran-5-yl)-4-methyl-4-hexenoic acid;
(E)-6-(1,3-dihydro-4-ethylamino-6-methoxy-7-methyl-3-oxoisobenzofuran-5-yl)-4-methyl-4-hexenoic acid and
(E)-6-(1,3-dihydro-4-isopropylamino-6-methoxy-7-methyl-3-oxoisobenzofuran-5-yl)-4-methyl-4-hexenoic acid;
there are obtained the following respective compounds:
2-(morpholin-4-yl)ethyl E-6-(1,3-dihydro-4-methylamino-6-methoxy-7-methyl-3-oxoisobenzofuran-5-yl)-4-methyl-4-hexenoate;
2-(morpholin-4-yl)ethyl (E)-6-(1,3-dihydro-4-ethylamino-6-methoxy-7-methyl-3-oxoisobenzofuran-5-yl)-4-methyl-4-hexenoic acid; and
2-(morpholin-4-yl)ethyl (E)-6-(1,3-dihydro-4-isopropylamino-6-methoxy-7-methyl-3-oxoisobenzofuran-5-yl)-4-methyl-4-hexenoic acid.

22B. Formula IE where $R^2$ is Hydrogen, varying $R^1$ and $R^7$

Similarly, following the procedure of Example 22A above, but replacing morpholinoethanol with the following heterocyclic lower alkanols (other compounds of the formula $R^7OH$) (which may be commercially obtained or prepared by methods known to those skilled in the art):
2-(pyrrolidin-1-yl)ethanol, 2-(piperidin-1-yl)ethanol, 2-(thiazolidin-3-yl)ethanol, 3-(morpholin-4-yl)propanol, 4-(morpholin-4-yl)butanol, 2-(imidazolidin-1-yl)ethanol and 2-(2-methyl-1,2-pyrazolidin-1-yl)ethanol;
there are obtained the following respective compounds:
2-(pyrrolidin-1-yl)ethyl (E)-6-(1,3-dihydro-4-methylamino-6-methoxy-7-methyl-3-oxoisobenzofuran-5-yl)-4-methyl-4-hexenoate;
2-(piperidin-1-yl)ethyl (E)-6-(1,3-dihydro-4-methylamino-6-methoxy-7-methyl-3-oxoisobenzofuran-5-yl)-4-methyl-4-hexenoate;
2-(thiazolidin-3-yl)ethyl (E)-6-(1,3-dihydro-4-methylamino-6-methoxy-7-methyl-3-oxoisobenzofuran-5-yl)-4-methyl-4-hexenoate;
3-(morpholin-4-yl)propyl (E)-6-(1,3-dihydro-4-methylamino-6-methoxy-7-methyl-3-oxoisobenzofuran-5-yl)-4-methyl-4-hexenoate;
4-(morpholin-4-yl)butyl (E)-6-(1,3-dihydro-4-methylamino-6-methoxy-7-methyl-3-oxoisobenzofuran-5-yl)-4-methyl-4-hexenoate;
2-(imidazolidin-1-yl)ethyl (E)-6-(1,3-dihydro-4-methylamino-6-methoxy-7-methyl-3-oxoisobenzofuran-5-yl)-4-methyl-4-hexenoate;
2-(2-methyl-1,2-pyrazolidin-1-yl)ethyl (E)-6-(1,3-dihydro-4-methylamino-6-methoxy-7-methyl-3-oxoisobenzofuran-5-yl)-4-methyl-4-hexenoate;
2-(pyrrolidin-1-yl)ethyl (E)-6-(1,3-dihydro-4-ethylamino-6-methoxy-7-methyl-3-oxoisobenzofuran-5-yl)-4-methyl-4-hexenoate;
2-(piperidin-1-yl)ethyl (E)-6-(1,3-dihydro-4-ethylamino-6-methoxy-7-methyl-3-oxoisobenzofuran-5-yl)-4-methyl-4-hexenoate;
2-(thiazolidin-3-yl)ethyl (E)-6-(1,3-dihydro-4-ethylamino-6-methoxy-7-methyl-3-oxoisobenzofuran-5-yl)-4-methyl-4-hexenoate;
3-(morpholin-4-yl)propyl (E)-6-(1,3-dihydro-4-ethylamino-6-methoxy-7-methyl-3-oxoisobenzofuran-5-yl)-4-methyl-4-hexenoate;
4-(morpholin-4-yl)butyl (E)-6-(1,3-dihydro-4-ethylamino-6-methoxy-7-methyl-3-oxoisobenzofuran-5-yl)-4-methyl-4-hexenoate;
2-(imidazolidin-1-yl)ethyl (E)-6-(1,3-dihydro-4-ethylamino-6-methoxy-7-methyl-3-oxoisobenzofuran-5-yl)-4-methyl-4-hexenoate;
2-(2-methyl-1,2-pyrazolidin-1-yl)ethyl (E)-6-(1,3-dihydro-4-ethylamino-6-methoxy-7-methyl-3-oxoisobenzofuran-5-yl)-4-methyl-4-hexenoate;
2-(pyrrolidin-1-yl)ethyl (E)-6-(1,3-dihydro-4-isopropylamino-6-methoxy-7-methyl-3-oxoisobenzofuran-5-yl)-4-methyl-4-hexenoate;

2-(piperidin-1-yl)ethyl (E)-6-(1,3-dihydro-4-isopropylamino-6-methoxy-7-methyl-3-oxoisobenzofuran-5-yl)-4-methyl-4-hexenoate;

2-(thiazolidin-3-yl)ethyl (E)-6-(1,3-dihydro-4-isopropylamino-6-methoxy-7-methyl-3-oxoisobenzofuran-5-yl)-4-methyl-4-hexenoate;

3-(morpholin-4-yl)propyl (E)-6-(1,3-dihydro-4-isopropylamino-6-methoxy-7-methyl-3-oxoisobenzofuran-5-yl)-4-methyl-4-hexenoate;

4-(morpholin-4-yl)butyl (E)-6-(1,3-dihydro-4-isopropylamino-6-methoxy-7-methyl-3-oxoisobenzofuran-5-yl)-4-methyl-4-hexenoate;

2-(imidazolidin-1-yl)ethyl (E)-6-(1,3-dihydro-4-isopropylamino-6-methoxy-7-methyl-3-oxoisobenzofuran-5-yl)-4-methyl-4-hexenoate; and 2-(2-methyl-1,2-pyrazolidin-1-yl)ethyl (E)-6-(1,3-dihydro-4-isopropylamino-6-methoxy-7-methyl-3-oxoisobenzofuran-5-yl)-4-methyl-4-hexenoate.

EXAMPLE 23

Preparation of Compounds of Formula (I) where $R^2$ is $-CO_2R^6$

23A. Preparation of (E)-6-(1,3-dihydro-4-methoxycarbonylamino-6-methoxy-7-methyl-3-oxoisobenzofuran-5-yl)-4-methyl-4-hexenoic acid A solution of methyl (E)-6-(1,3-dihydro-4-isocyanato-6-methoxy-7-methyl-3-oxoisobenzofuran-5-yl)-4-methyl-4-hexenoate (1.0 g) in 10 ml methanol was heated to reflux for 4 hours and then evaporated to dryness. The residue was recrystallized from acetone/hexane to give 0.41 g of methyl (E)-6-(1,3-dihydro-4-methoxycarbonylamino-6-methoxy-7-methyl-3-oxoisobenzofuran-5-yl)-4-methyl-4-hexenoate. The ester (0.35 g) and 0.05 g of LiOH-H$_2$O in 9 ml 2:1 MeOH-H$_2$O was heated at reflux for 4 hours. The mixture was acidified, extracted with ethyl acetate, and the organic layer was dried over MgSO$_4$. The organic layer was concentrated and the residue was further purified by silica gel chromatography (eluant 60:40:2 hexane:ethyl acetate:acetic acid) to give 0.21 g of (E)-6-(1,3-dihydro-4-methoxycarbonylamino-6-methoxy-7-methyl-3-oxoisobenzofuran-5-yl)-4-methyl-4-hexenoic acid, mp 155°–158° C.

23B. Formula I where $R^2$ is $-CO_2R^6$

Similarly, following the procedure of Example 23A above, but replacing methanol with other alkanols of Formula $R^6OH$, other carbamates of Formula I are prepared.

EXAMPLE 24

Preparation of Compounds of Formula (I) where $R^2$ is $-SO_2R^3$

24A. Preparation of (E)-6-(1,3-dihydro-4-methylsulfonamido-6-methoxy-7-methyl-3-oxoisobenzofuran-5-yl)-4-methyl-4-hexenoic acid To a solution of 0.66 g of methyl (E)-6-(1,3-dihydro-4-amino-6-methoxy-7-methyl-3-oxoisobenzofuran-5-yl)-4-methyl-4-hexenoate in 5 ml dichloromethane was added 0.24 ml of pyridine and 0.5 g of methanesulfonic anhydride. After 1 hour the mixture was partitioned between water and dichloromethane. The organic layer was dried over MgSO$_4$, and concentrated to give crude methyl (E)-6-(1,3-dihydro-4-methylsulfonamido-6-methoxy-7-methyl-3-oxoisobenzofuran-5-yl)-4-methyl-4-hexenoate. This material was purified by silica gel chromatography with 1:1 hexane-ethyl acetate. The purified ester was then treated with 0.1 g LiOH-H$_2$O in 10 ml 1:1 methanol:H$_2$O and the mixture refluxed for 1.5 hours. After cooling, the mixture was partitioned between dilute aqueous HCl and ethyl acetate. The organic layer was dried over MgSO$_4$ and concentrated. The residue was purified on silica gel (eluant 80:80:4 EtOAc:hexane:acetic acid) to give 0.12 g of (E)-6-(1,3-dihydro-4-methylsulfonamido-6-methoxy-7-methyl-3-oxoisobenzofuran-5-yl)-4-methyl-4-hexenoic acid, mp 170°–176° C.

24B. Formula I where $R^2$ is $-SO_2R^3$

Similarly, following the procedure of Example 24A above, but replacing methanesulfonic anhydride with other sulfonating agents, other sulfonamides of Formula I are prepared.

EXAMPLE 25

This example illustrates the preparation of a representative pharmaceutical formulation for oral administration containing an active compound of Formula I, e.g., (E)-6-(1,3-dihydro-4-amino-6-methoxy-7-methyl-3-oxoisobenzofuran-5-yl)-4-methyl-4-hexenoic acid.

| Ingredients | Quantity per tablet, mgs. |
|---|---|
| Active Compound | 200 |
| Lactose, spray-dried | 148 |
| Magnesium stearate | 2 |

The above ingredients are mixed and introduced into a hard-shell gelatin capsule.

Other compounds of Formula I, such as those prepared in accordance with Examples 8–24, can be used as the active compound in the preparation of the orally administrable formulations of this example.

EXAMPLE 26

This example illustrates the preparation of another representative pharmaceutical formulation for oral administration containing an active compound of Formula I, e.g., (E)-6-(1,3-dihydro-4-amino-6-methoxy-7-methyl-3-oxoisobenzofuran-5-yl)-4-methyl-4-hexenoic acid.

| Ingredients | Quantity per tablet, mgs. |
|---|---|
| Active Compound | 400 |
| Cornstarch | 50 |
| Lactose | 145 |
| Magnesium stearate | 5 |

The above ingredients are mixed intimately and pressed into single scored tablets.

Other compounds of Formula I, such as those prepared in accordance with Examples 8–24, can be used as the active compound in the preparation of the orally administrable formulations of this example.

EXAMPLE 27

This example illustrates the preparation of a representative pharmaceutical formulation containing an active compound of Formula I, e.g., (E)-6-(1,3-dihydro-4-amino-6-methoxy-7-methyl-3-oxoisobenzofuran-5-yl)-4-methyl-4-hexenoic acid.

An oral suspension is prepared having the following composition.

| Ingredients | |
|---|---|
| Active Compound | 1.0 g |

| Ingredients | |
|---|---|
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

Other compounds of Formula I, such as those prepared in accordance with Examples 8-24, can be used as the active compound in the preparation of the orally administrable formulations of this example.

EXAMPLE 28

This example illustrates the preparation of a representative pharmaceutical formulation for oral administration containing an active compound of Formula I, e.g., (E)-6-(1,3-dihydro-4-amino-6-methoxy-7-methyl-3-oxoisobenzofuran-5-yl)-4-methyl-4-hexenoic acid.

An injectable preparation buffered to a pH of 4 is prepared having the following composition:

| Ingredients | |
|---|---|
| Active Compound | 0.2 g |
| Sodium Acetate Buffer Solution (0.4 M) | 2.0 ml |
| HCL (1N) | q.s. to pH 4 |
| Water (distilled, sterile) | q.s. to 20 ml |

Other compounds of Formula I, such as those prepared in accordance with Examples 8-24, can be used as the active compound in the preparation of the injectable formulations of this example.

EXAMPLE 29

This example illustrates the preparation of a representative pharmaceutical formulation for topical application containing an active compound of Formula I, e.g., (E)-6-(1,3-dihydro-4-amino-6-methoxy-7-methyl-3-oxoisobenzofuran-5-yl)-4-methyl-4-hexenoic acid.

| Ingredients | grams |
|---|---|
| Active compound | 0.2-10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of Formula I, such as those prepared in accordance with Examples 8-24, can be used as the active compound in the preparation of the topical formulations of this example.

EXAMPLE 30

This example illustrates the preparation of a representative pharmaceutical formulation containing an active compound of Formula I, e.g., (E)-6-(1,3-dihydro-4-amino-6-methoxy-7-methyl-3-oxoisobenzofuran-5-yl)-4-methyl-4-hexenoic acid.

A suppository totalling 2.5 grams is prepared having the following composition:

| Ingredients | |
|---|---|
| Active Compound | 500 mg |
| Witepsol H-15* | balance |

*(triglycerides of saturated vegetable fatty acid; a product of Riches-Nelson, Inc., New York, N.Y.)

Other compounds of Formula I, such as those prepared in accordance with Examples 8-24, can be used as the active compound in the preparation of the suppository formulations of this example.

EXAMPLE 31

In Vitro Determination of Therapeutic Activity (As an Anti-Inflammatory, Anti-Viral, Anti-Tumor, Anti-Psoriatic and/or Immunosuppressive Agent) Utilizing the Inhibition of IMP Dehydrogenase Assay This assay is a modification of the method of Anderson, J. H. and Sartorelli, A. C., *Jour. Biol. Chem*, 243:4762-4768 (1968). It measures the formation of NADH ($\lambda_{max}$=340 nm, $\epsilon 340$=6,220$M^{-1}$ $cm^{-1}$) as Inosine 5'-monophosphate ("IMP") is converted to Xanthosine 5'-monophosphate ("XMP") by the human Type II IMP dehydrogenase ("IMPDH").

Compounds are dissolved and diluted in DMSO, and reaction solutions containing compounds at 0, 0.01, 0.10, 1.0, 10, and 100 $\mu$M are prepared in disposable methacrylic plastic microcuvets ('UV-transparent' plastic, 1 cm pathlength, 1.5 ml capacity). The solutions (0.5-1 ml) contain the following: 0.1M TrisHCL, pH 8.0; 0.1M KCL; 3.0 mM EDTA; 100 $\mu$g/ml BSA; 0.05 mM IMP; 0.10 mM NAD; 10% DMSO; 5-15 nM IMPDH (0.003-0.010 units/ml; one unit of enzyme catalyzes the formation of one $\mu$mol NADH per minute at 40° C. at saturating substrate concentrations—200 $\mu$M IMP and 400$\mu$M NAD). Reactions are performed at 40° C. and initiated by the addition of enzyme. Mycophenolic acid ($IC_{50} \approx 0.02$ $\mu$M) serves as the positive control. The reactions are monitored at 340 nm for 10 minutes in a UV/VIS spectrophotometer, and rate data are collected.

The 50% inhibitory value ("$IC_{50}$") is determined by fitting the fractional activities relative to control to the following equation on a Macintosh computer by the program Systat:

$$\text{Fractional activity} = MAX/((X/IC_{50})^n + 1).$$

X is the concentration of the compound, and the term n accounts for deviations of the data from a simple competitive inhibition model.

The compounds of the present invention inhibit IMPDH when tested by this method, indicating their activity as anti-inflammatory, anti-viral, anti-tumor, anti-psoriatic and/or immunosuppressive agents.

EXAMPLE 32

In Vitro Determination of Immunosuppressive Activity Utilizing Responses of Human Peripheral Blood Lymphocytes to T- and B-cell Mitogens This procedure is a modification of a procedure initially described by Greaves, et al. ["Activation of human T and B lymphocytes by polyclonal mitogens," *Nature*, 248:698–701 (1974)].

Human mononuclear cells ("PBL") are separated from heparinized whole blood by density gradient centrifugation in Ficoll-Plaque (Pharmacia). After washing, $2\times10^5$ cells/well are cultured in microtiter plates with RPMI 1640 supplemented with 5% fetal calf serum, penicillin and streptomycin. PHA (Sigma) at 10 μg/ml is then added. Test materials are tested at concentrations between $10^4$ and $10^8$M, by addition to the culture at time 0. Cultures are set up in quadruplicate and incubated at 37° C. in a humidified atmosphere with 7% $CO_2$ for 72 hours. A pulse of 0.5 μCi/well of $^3$H-thymidine is added for the last 6 hours. Cells are collected on glass fiber filters with an automatic harvester and radioactivity is measured by standard scintillation procedures. The 50% inhibitory concentration ("IC$_{50}$") for mitogenic stimulation is determined graphically.

To evaluate differential effects on T- and B-lymphocytes, different mitogens are used: PWM (Sigma) at 20 μg/ml and Staphylococcus Protein A bound to Sepharose (SPA) (Sigma) 2 mg/ml or 14 μg/ml of Protein A.

The compounds of the present invention show immunosuppressive activity when tested by this method.

EXAMPLE 33

Determination of Immunosuppressive Activity Utilizing the Hemolytic Plaque Forming Cell Assay This procedure is a modification of "The agar plaque technique for recognizing antibody producing cells," a procedure initially described by Jerne et al., [*Cellbound Antibodies*, Amos and Kaprowski editors (Wistar Institute Press, Philadelphia, 1963), p. 109].

Groups of 5–6 adult C578B1/6 male mice were sensitized with $1\times10^8$ sheep red blood cells ("SRBC") and simultaneously treated with an oral dosage form of the test material in an aqueous vehicle. Animals in a control group receive the same volume of vehicle. Four days after SRBC inoculation, spleens are dispersed in loose Ten Broeck homogenizers. The number of nucleated cells ("WBC") is determined and the spleen cell suspension is mixed with SRBC, guinea pig complement and agar solution at 0.5% concentration. Aliquots of the above mixture (0.1 ml) are dropped on four separate quadrants of a Petri dish and are covered with cover slips. After two hours incubation at 37° C., areas of hemolysis around plaque-forming cells ("PFC") are counted with a dissecting microscope. Total WBC/spleen, PFC/spleen and PFC/$10^6$ WBC ("PPM") are calculated for each mouse spleen. Geometric means of each treatment group are then compared with the vehicle-treated control group.

The compounds of the present invention show immunosuppressive activity when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound represented by the formula:

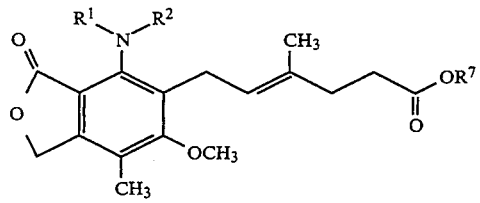

wherein:
  $R^1$ is hydrogen or lower alkyl;
  $R^2$ is hydrogen, lower alkyl, —C(O)$R^3$, or —C(O)N$R^4R^5$, where $R^3$ is halomethyl, and $R^4$ and $R^5$ are independently hydrogen, lower alkyl, or optionally substituted phenyl; and
  $R^7$ is hydrogen, lower alkyl, optionally substituted phenyl, or —(CH$_2$)$_m$—N=Y, wherein:
    m is an integer from two to four; and
    Y is lower alkylene of four to six carbon atoms and or lower alkylene of three to five carbon atoms and one member that is —O—, —S—, or —N(R$^8$)—, where $R^8$ is hydrogen or lower alkyl;
or a pharmaceutically acceptable salt thereof.

2. The compound or salt of claim 1 wherein $R^1$ is hydrogen.

3. The compound or salt of claim 2 wherein $R^2$ is hydrogen or —C(O)$R^3$.

4. The compound or salt of claim 3 wherein $R^2$ is hydrogen.

5. The compound or salt of claim 4 wherein $R^7$ is hydrogen, namely (E)-6-(1,3-dihydro-4-amino-6-methoxy-7-methyl-3-oxoisobenzofuran-5-yl)-4-methyl-4-hexenoic acid.

6. The compound or salt of claim 4 wherein $R^7$ is lower alkyl.

7. The compound or salt of claim 4 wherein $R^7$ is morpholinoethyl, namely 2-(morpholin-4-yl)ethyl (E)-6-(1,3-dihydro-4-amino-6-methoxy-7-methyl-3-oxoisobenzofuran-5-yl)-4-methyl-4-hexenoate.

8. The compound or salt of claim 3 wherein $R^2$ is —C(O)$R^3$.

9. The compound or salt of claim 8 wherein $R^3$ is —CF$_3$.

10. The compound or salt of claim 9 wherein $R^7$ is hydrogen, namely (E)-6-[1,3-dihydro-4-(trifluoroacetyl)amino-6-methoxy-7-methyl-3-oxoisobenzofuran-5-yl]-4-methyl-4-hexenoic acid.

11. The compound or salt of claim 9 wherein $R^7$ is lower alkyl.

12. The compound or salt of claim 9 wherein $R^7$ is morpholinoethyl, namely 2-(morpholin-4-yl)ethyl (E)-6-[1,3-dihydro-4-(trifluoroacetyl)amino-6-methoxy-7-methyl-3-oxoisobenzofuran-5-yl]-4-methyl-4-hexenoate.

13. The compound or salt of claim 2 wherein $R^2$ is lower alkyl.

14. The compound or salt of claim 13 wherein $R^2$ is methyl and $R^7$ is hydrogen, namely (E)-6-(1,3-dihydro-4-methylamino-6-methoxy-7-methyl-3-oxoisobenzofuran-5-yl)-4-methyl-4-hexenoic acid.

15. The compound or salt of claim 2 wherein $R^2$ is —C(O)N$R^4R^5$.

16. The compound or salt of claim 15 wherein $R^7$ is hydrogen.

17. The compound or salt of claim 16 wherein $R^4$ and $R^5$ are both methyl, namely (E)-6-[1,3-dihydro-4-(3,3-dimethylureido)-6-methoxy-7-methyl-3-oxoisobenzofuran-5-yl]-4-methyl-4-hexenoic acid.

18. A pharmaceutical composition comprising a pharmaceutically acceptable non-toxic excipient and a therapeutically effective amount of a compound or salt of claim 1.

* * * * *